(12) United States Patent
Sugiyama et al.

(10) Patent No.: US 8,202,711 B2
(45) Date of Patent: *Jun. 19, 2012

(54) PROCESS FOR PRODUCING GLUTAMATE DERIVATIVES

(75) Inventors: Masakazu Sugiyama, Kawasaki (JP); Kunihiko Watanabe, Kawasaki (JP); Nao Funakoshi, Kawasaki (JP); Yusuke Amino, Kawasaki (JP); Shigeru Kawahara, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/768,360

(22) Filed: Apr. 27, 2010

(65) Prior Publication Data

US 2010/0261234 A1    Oct. 14, 2010

Related U.S. Application Data

(60) Continuation of application No. 12/108,889, filed on Apr. 24, 2008, now abandoned, which is a division of application No. 11/561,665, filed on Nov. 20, 2006, which is a division of application No. 10/876,468, filed on Jun. 28, 2004, now Pat. No. 7,297,800, which is a continuation of application No. PCT/JP02/12852, filed on Dec. 9, 2002.

(30) Foreign Application Priority Data

| Dec. 27, 2001 | (JP) | 2001-396471 |
| Mar. 29, 2002 | (JP) | 2002-095760 |
| Aug. 26, 2002 | (JP) | 2002-245980 |

(51) Int. Cl.
C12P 17/10 (2006.01)
C12P 17/00 (2006.01)

(52) U.S. Cl. ............... 435/121; 435/122; 435/146

(58) Field of Classification Search .................. None
See application file for complete search history.

(56) References Cited

U.S. PATENT DOCUMENTS

| 3,036,958 A | 5/1962 | Asai et al. |
| 3,751,458 A | 8/1973 | Wiley |
| 4,518,692 A | 5/1985 | Rozzell |
| 4,551,471 A | 11/1985 | De Luca et al. |
| 4,605,615 A | 8/1986 | Ishikawa et al. |
| 4,808,728 A | 2/1989 | De Luca et al. |
| 4,935,507 A | 6/1990 | Takaya et al. |
| 4,975,298 A | 12/1990 | Van Wyk et al. |
| 5,128,164 A | 7/1992 | Van Wyk et al. |
| 5,128,482 A | 7/1992 | Olivier et al. |
| 5,707,842 A | 1/1998 | Spencer et al. |
| 5,728,555 A | 3/1998 | Fotheringham et al. |
| 5,948,886 A | 9/1999 | Peet et al. |
| 5,994,559 A | 11/1999 | Abushanab et al. |
| 6,207,427 B1 | 3/2001 | Hashimoto et al. |
| 6,337,190 B1 | 1/2002 | Hwang et al. |
| 6,358,714 B1 | 3/2002 | Fotheringham et al. |
| 6,635,749 B2 | 10/2003 | Frankel |
| 6,649,387 B2 | 11/2003 | Patel et al. |
| 6,777,388 B1 | 8/2004 | Grasso et al. |
| 7,064,219 B2 | 6/2006 | Kawahara et al. |
| 7,241,599 B2 | 7/2007 | Sugiyama et al. |
| 7,244,462 B2 | 7/2007 | Amino et al. |
| 7,297,800 B2 | 11/2007 | Sugiyama et al. |
| 7,329,427 B2 | 2/2008 | Amino et al. |
| 7,351,569 B2 | 4/2008 | Sugiyama et al. |
| 7,354,746 B1 | 4/2008 | Suzuki et al. |
| 7,371,549 B2 | 5/2008 | Sugiyama et al. |
| 7,390,909 B2 | 6/2008 | Kawahara et al. |
| 7,396,941 B2 | 7/2008 | Mori et al. |
| 7,402,412 B2 | 7/2008 | Sugiyama et al. |
| 7,432,100 B2 | 10/2008 | Sugiyama et al. |
| 7,534,590 B2 | 5/2009 | Mori et al. |
| 7,534,898 B2 | 5/2009 | Amino et al. |
| 7,553,974 B2 | 6/2009 | Mori et al. |
| 7,572,607 B2 | 8/2009 | Hicks et al. |
| 7,582,455 B2 | 9/2009 | Brazeau et al. |
| 7,612,214 B2 | 11/2009 | Amino et al. |

(Continued)

FOREIGN PATENT DOCUMENTS

CN    1214366 A    4/1999

(Continued)

OTHER PUBLICATIONS

K. Maruyama, "Purification and Properties of 4-Hydroxy-4-Methyl-2-Oxoglutarate Aldolase From *Pseudomonas ochraceae* Grown on Phthalate", J. Biochem., vol. 108, No. 2, 1990, pp. 327-333.

(Continued)

*Primary Examiner* — Julie Ha

(74) *Attorney, Agent, or Firm* — Oblon, Spivak, McClelland, Maier & Neustadt, L.L.P.

(57) ABSTRACT

The present invention relates to a process for producing efficiently glutamic acid derivatives (including salts thereof) such as monatin by converting a substituted α-keto acid of formula (1) into a glutamic acid derivative of formula (2) in the presence of an enzyme catalyzing conversion of the same.

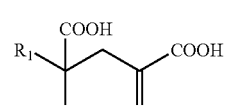

(1)

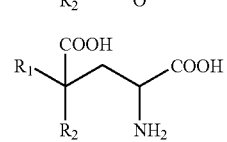

(2)

27 Claims, No Drawings

U.S. PATENT DOCUMENTS

| | | |
|---|---|---|
| 7,662,596 B2 | 2/2010 | Sugiyama et al. |
| 7,674,915 B2 | 3/2010 | Amino |
| 7,678,925 B2 | 3/2010 | Kawahara et al. |
| 7,781,005 B2 | 8/2010 | Mori |
| 7,795,296 B2 | 9/2010 | Amino et al. |
| 7,816,541 B2 | 10/2010 | Kawahara et al. |
| 7,868,187 B2 | 1/2011 | Kawahara et al. |
| 7,888,081 B2 | 2/2011 | Khare et al. |
| 7,935,377 B2 | 5/2011 | Amino et al. |
| 7,951,835 B2 | 5/2011 | Amino et al. |
| 7,973,070 B2 | 7/2011 | Mori et al. |
| 7,981,460 B2 | 7/2011 | Amino et al. |
| 8,003,361 B2 | 8/2011 | Brady et al. |
| 8,043,836 B2 | 10/2011 | Sugiyama et al. |
| 8,043,837 B2 | 10/2011 | Burke et al. |
| 8,048,647 B2 | 11/2011 | Sugiyama et al. |
| 8,058,034 B2 | 11/2011 | Sugiyama et al. |
| 8,058,038 B2 | 11/2011 | Sugiyama et al. |
| 8,076,107 B2 | 12/2011 | Buddoo et al. |
| 8,076,108 B2 | 12/2011 | Brazeau et al. |
| 2003/0228403 A1 | 12/2003 | Amino et al. |
| 2004/0063175 A1 | 4/2004 | Abraham et al. |
| 2005/0004394 A1 | 1/2005 | Kawahara et al. |
| 2005/0009153 A1 | 1/2005 | Sugiyama et al. |
| 2005/0020508 A1 | 1/2005 | Amino et al. |
| 2005/0106305 A1 | 5/2005 | Abraham et al. |
| 2005/0112260 A1 | 5/2005 | Abraham et al. |
| 2005/0118317 A1 | 6/2005 | Amino et al. |
| 2005/0137246 A1 | 6/2005 | Amino et al. |
| 2005/0153405 A1 | 7/2005 | Sugiyama et al. |
| 2005/0170041 A1 | 8/2005 | Abraham et al. |
| 2005/0221455 A1 | 10/2005 | McFarlan et al. |
| 2005/0244937 A1 | 11/2005 | Abraham et al. |
| 2005/0244939 A1 | 11/2005 | Sugiyama et al. |
| 2005/0272939 A1 | 12/2005 | Amino et al. |
| 2005/0282260 A1 | 12/2005 | Hicks et al. |
| 2006/0003411 A1 | 1/2006 | Sugiyama et al. |
| 2006/0003426 A1 | 1/2006 | Sugiyama et al. |
| 2006/0009394 A1 | 1/2006 | Amino |
| 2006/0014819 A1 | 1/2006 | Mori et al. |
| 2006/0074249 A1 | 4/2006 | Kawahara et al. |
| 2006/0083695 A1 | 4/2006 | Mori |
| 2006/0154343 A1 | 7/2006 | Mori et al. |
| 2006/0172396 A1 | 8/2006 | Sugiyama et al. |
| 2006/0252135 A1 | 11/2006 | Brazeau et al. |
| 2006/0257550 A1 | 11/2006 | Mori |
| 2007/0066832 A1 | 3/2007 | Mori et al. |
| 2007/0072277 A1 | 3/2007 | Sugiyama et al. |
| 2007/0099277 A1 | 5/2007 | Anderson et al. |
| 2007/0105938 A1 | 5/2007 | Anderson et al. |
| 2007/0122535 A1 | 5/2007 | Stouffs et al. |
| 2007/0191464 A1 | 8/2007 | Amino et al. |
| 2008/0015361 A1 | 1/2008 | Khare et al. |
| 2008/0020435 A1 | 1/2008 | Burke et al. |
| 2008/0091032 A1 | 4/2008 | Kawahara et al. |
| 2008/0193975 A1 | 8/2008 | Sugiyama et al. |
| 2008/0193984 A1 | 8/2008 | Sugiyama et al. |
| 2008/0199921 A1 | 8/2008 | Sugiyama et al. |
| 2008/0207920 A1 | 8/2008 | Kawahara et al. |
| 2008/0274518 A1 | 11/2008 | Hicks et al. |
| 2008/0318290 A1 | 12/2008 | Sugiyama et al. |
| 2009/0117625 A1 | 5/2009 | Abraham et al. |
| 2009/0170942 A1 | 7/2009 | Amino et al. |
| 2009/0198072 A1 | 8/2009 | Khare et al. |
| 2009/0202697 A1 | 8/2009 | Erickson et al. |
| 2009/0203774 A1 | 8/2009 | Amino et al. |
| 2009/0238940 A1 | 9/2009 | Horky et al. |
| 2009/0258403 A1 | 10/2009 | Sugiyama et al. |
| 2009/0259052 A1 | 10/2009 | Kawahara et al. |
| 2009/0318528 A1 | 12/2009 | Mori et al. |
| 2010/0010234 A1 | 1/2010 | Amino |
| 2010/0105924 A1 | 4/2010 | Kawahara et al. |
| 2010/0112174 A1 | 5/2010 | Christensen et al. |
| 2010/0184165 A1 | 7/2010 | Sugiyama et al. |
| 2010/0221795 A1 | 9/2010 | Takakura et al. |
| 2010/0255548 A1 | 10/2010 | Sugiyama et al. |
| 2010/0261234 A1 | 10/2010 | Sugiyama et al. |
| 2010/0279365 A1 | 11/2010 | Sugiyama et al. |
| 2010/0323411 A1 | 12/2010 | Sugiyama et al. |
| 2010/0330245 A1 | 12/2010 | Amino et al. |
| 2011/0059218 A1 | 3/2011 | Corliss et al. |
| 2011/0189368 A1 | 8/2011 | Amino et al. |
| 2011/0189738 A1 | 8/2011 | Sugiyama et al. |
| 2011/0218227 A1 | 9/2011 | Mori et al. |
| 2011/0293781 A1 | 12/2011 | Guthrie et al. |
| 2011/0293813 A1 | 12/2011 | Cavallini et al. |
| 2011/0293814 A1 | 12/2011 | Alexandre et al. |
| 2011/0300282 A1 | 12/2011 | Brady et al. |

FOREIGN PATENT DOCUMENTS

| | | |
|---|---|---|
| CN | 1656068 | 8/2005 |
| CN | 1749402 A | 3/2006 |
| EP | 0 186 035 A2 | 7/1986 |
| EP | 0 438 314 | 7/1991 |
| EP | 0 692 539 A2 | 1/1996 |
| EP | 0 736 604 A2 | 10/1996 |
| EP | 1 045 029 A2 | 10/2000 |
| EP | 1 045 029 A3 | 10/2000 |
| EP | 1 445 323 A1 | 8/2004 |
| EP | 2 050 821 A2 | 4/2009 |
| JP | 64-025757 | 1/1989 |
| JP | 64-25757 | 1/1989 |
| JP | 04-217654 | 8/1992 |
| JP | 04-218386 | 8/1992 |
| JP | 4-218386 | 8/1992 |
| JP | 2002-60382 | 2/2002 |
| JP | 2004-331650 | 11/2004 |
| WO | WO 03/056026 A1 | 7/2003 |
| WO | WO 03/059865 | 7/2003 |
| WO | WO 03/091396 | 11/2003 |
| WO | WO 03/091396 A2 | 11/2003 |
| WO | WO 2004/067494 A1 | 8/2004 |

OTHER PUBLICATIONS

R. Bode, et al., "Enzymatic Production of Indolepyruvate and Some of Its Methyl and Fluoro-derivatives", Acta Biotechnologies, 11, 4, (1991), pp. 387-393.

E.G. Ivanova, et al., "Aerobic Methylobacteria Are Capable of Synthesizing Auxins", Microbiology, vol. 70, No. 4, 2001, pp. 392-397.

Y. Furuya, et al., "A Novel Enzyme, L-Tryptophan Oxidase, From a Basidiomycete, *Coprinus* sp. SF-1: Purification and Characterization", Biosci. Biotechnol. Biochem., 64 (7), 2000, pp. 1486-1493.

D. D. J. Oliveira, et al., Tetrahedron Letters, vol. 42, No. 39, pp. 6793-6796, "Diastereoselective Formation of Quaternary Center in a Pyroglutamate Derivative. Formal Synthesis of Monatin", 2001.

K. Nakamura, et al., Organic Letters, vol. 2, No. 19, pp. 2967-2970, "Total Synthesis of Monatin," 2000.

C. W. Holzapfel, et al.,. Synthetic Communication, vol. 24, No. 22, pp. 3197-3211, "A Simple Cycloaddition Approach to a Racemate of the Natural Sweetener Monatin", 1994.

C. W. Holzapfel, et al., Synthetic Communications, vol. 23, No. 18, pp. 2511-2526, "The Synthesis of a γ-Keto-α-Amino Acid, a Key Intermediate in the Sunthesis of Monatin, a New Natural Sweetener", 1993.

R. Vleggaar, et al., J. Chem. Soc. Perkin Trans., 1, pp. 3095-3098, "Structure Elucidation of Monatin, a High-Intensity Sweetner Isolated From the Plant *Schlerochiton ilicifolius*", 1992.

R. V. Patil, et al., Jourlan of Bacteriology, vo. 174, No. 1, pp. 102-107, "Cloning, Nucleotide Sequence, Overexpression, and Inactivation of the *Escherichia coli* 2-Keto-4-Hydroxyglutarate Aldolase Gene," Jan. 1992.

A. Galkin, et al.,. Applied and Environmental Microbiology, vol. 63, No. 12, pp. 4651-4656, "Synthesis of Optically Active Amino Acids From α-Keto Acids With *Escherichia coli* Cells Expressing Heterologous Genes," Dec. 1997.

A. DeLuna, et al., The Journal of Biological Chemistry, vol. 276, No. 47, pp. 43775-43783, "NADP-Glutamate Dehydrogenase Isoenzymes of *Saccharomyces*," Nov. 23, 2001.

Kuramitsu, S., et al., "Aspartate Aminotransferase of *Escherichia coli*: Nucleotide Sequence of the aspC Gene[1]," J. Biochem., 97, 1985, pp. 1259-1262.

Watson, R. J., et al., "Cloning and Nucleotide Sequencing of *Rhizobium meliloti* Aminotransferase Genes: an Aspartate Aminotransferase Required for Symbiotic Nitrogen Fixation Is Atypical," Journal of Bacteriology, vol. 175, No. 7, Apr. 1993, pp. 1919-1928.

H.C. Winter, et al., "Specificity of Aspartate Aminotransferases From Leguminous Plants for 4-Substituted Glutamic Acids", Plant Physiol., 89, (1989), pp. 1122-1128.

K. Maruyama, et al., "Cloning, Sequencing, and Expression of the Gene Encoding 4-Hydroxy-4-Methyl-2-Oxoglutarate Aldolase From *Pseudomonas ochraceae* NGJ1", Biosci. Biotechnol. Biochem., 65 (12), 2001, pp. 2701-2709.

V. Helaine, et al., "Synthesis of 4,4-Disubstituted L-Glutamic Acids by Enzymatic Transamination", Adv. Synth. Catal., 343, No. 6-7, 2001, pp. 692-697.

V. Helaine, et al., "A New Access to Alkyl-α-Ketoglutaric Acids, Precursors of Glutamic Acid Analogues by Enzymatic Transamination. Application to the Synthesis of (2S,4R)-4-Propyl-glutamic Acid", Tetrahedron Letters, 40, 1999, pp. 6577-6580.

Voet D, Voet JG, Biochemistry, Second Edition, John Wiley & Sons, Inc., 1995, pp. 235-241.

Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.

Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.

Rudinger J. "Characteristics of the amino acids as components of a peptide hormone sequence," Peptide Hormones, JA Parsons Edition, University Park Press, Jun. 1976, pp. 1-7.

Schinzel R., Drueckes P, "The phosphate recognition site of *Escherichia coli* maltodextrin phosphorylase," FEBS, Jul. 1991, 286(1,2): 125-128.

Novogrodsky, A., et al., "Control of Aspartate β-Decarboxylase Activity by Transamination," The Journal of Biological Chemistry, vol. 239, No. 3, Mar. 1964, pp. 879-888.

Michael J. Pucci, et al., "*Staphylococcus haemolyticus* Contains Two D-Glutamic Acid Biosynthetic Activities, a Glutamate Racemase and a D-Amino Acid Transaminase", Journal of Bacteriology, vol. 177, No. 2, Jan. 1995, pp. 336-342.

Berendsen HJC, "A Glimpse of the Holy Grail?" Science, 1998, 282: 642-643.

U.S. Appl. No. 12/613,839, filed Nov. 6, 2009, Sugiyama, et al.
U.S. Appl. No. 12/613,713, filed Nov. 6, 2009, Kawahara, et al.
U.S. Appl. No. 12/758,433, filed Apr. 12, 2010, Sugiyama, et al.
U.S. Appl. No. 12/825,886, filed Jun. 29, 2010, Amino, et al.
U.S. Appl. No. 12/853,844, filed Aug. 10, 2010, Sugiyama, et al.
U.S. Appl. No. 07/178,323, filed Apr. 6, 1988, Amino, et al.
U.S. Appl. No. 13/081,024, filed Apr. 6, 2011, Amino, et al.
U.S. Appl. No. 13/044,618, filed Mar. 10, 2011, Sugiyama, et al.

Fotheringham, et al, "Characterization of the Genes Encoding D-Amino Acid Transaminase and Glutamate Racemase, Two D-Glutamate Biosynthetic Enzymes of *Bacillus sphaericus* ATCC 10208," Journal of Bacteriology, vol. 180, No. 16, pp. 4319-4323, Aug. 1998.

Sugio, et al. "Crystal Structure of a D-Amino Acid Aminotransferase: How the Protein Controls Stereoselectivity," Biochemistry, vol. 34, No. 30, pp. 9661-9669, 1995.

Ro, et al. "Site-Directed Mutagenesis of the Amino Acid Residues in Beta-Strand III [VAL30-VAL36] of D-Amino Acid Aminotransferase of *Bacillus* sp. YM-1," FEBS Letters, vol. 398, No. 2-3, pp. 141-145, Dec. 2, 1996.

Kishimoto, et al. "Role of Leucine 201 of Thermostable D-Amino Acid Aminotransferase From a Thermophile, *Bacillus* sp. YM-1," J. Biochem., vol. 117, No. 4, pp. 691-696, Apr. 1995.

U.S. Office Action dated Oct. 27, 2009 in co-pending U.S. Appl. No. 12/108,889.

D. Voet, et al., Biochemistry, Second Edition, John Wiley & Sons, Inc., 1995, pp. 235-241.

J. Ngo, et al., "Computational Complexity, Protein Structure Prediction, and the Levinthal Paradox," The Protein Folding Problem and Tertiary Structure Prediction, K. Merc Jr. and S. Le Grand Edition, 1994, pp. 491-495.

C. Bradley, et al., "Limits of Cooperativity in a Structurally Modular Protein: Response of the Notch Ankyrin Domain to Analogous Alanine Substitutions in Each Repeat," J. Mol. Biol., 2002, 324: 373-386.

Galkin, et al. Applied and Environmental Microbiology, vol. 63, No. 12, pp. 4651-4656. "Synthesis of Optically Active Amino Acids from α-Keto Acids with *Escherichia coli* Cells Expressing Heterologous Genes," Dec. 1997.

De Luna, et al. The Journal of Biological Chemistry, vol. 276, No. 47, pp. 43775-43783. "NADP-Glutamate Dehydrogenase Isoenzymes of *Saccharomyces*," Nov. 23, 2001.

Helaine, et al. "A New Access to Alkyl-α-Ketoglutaric Acids, Precursors of Glutamic Acid Analogues by Enzymatic Transamination. Application to the Synthesis of (2S,4R)-4-Propyl-Glutamic Acid," Tetrahedron Letters, 40, 1999, pp. 6577-6580.

Helaine, et al. "Synthesis of 4,4-Disubstituted L-Glutamic Acids by Enzymatic Transamination," Adv. Synth. Catal., 343, No. 6-7, 2001, pp. 692-697.

HC Winter, et al, "Specificity of Asparate Aminotransferases from Leguminous Plants for 4-Substituted Glutamic Acids," Plant Physiol., 89 (1989) pp. 1122-1128.

Bode, et al. "Enzymatic Production of Indolepyruvate and Some of its Methyl and Fluoro-Derivatives," Acta Biotechnologies, 11, 4, (1991), pp. 387-393.

Ivanova, et al. "Aerobic Methylobacteria are Capable of Synthesizing Auxins," Microbiology, vol. 70, No. 4, 2001, pp. 392-397.

Furuya, et al. "A Novel Enzyme, L-Tryptophan Oxidase, From a Basidiomycete, *Coprinus* sp. SF-1: Purification and Characterization," Biosci. Biotechnol. Biochem., 64 (7), 2000, pp. 1486-1493.

XP-002355975, "Probable Transferase Protein (EC 2.-.-.-)", retrieved from EBI accession No. UNIPROT: Q8XRB4 (Mar. 1, 2002).

K. Maruyama, et al., "Cloning, Sequencing, and Expression of the Gene Encoding 4-Hydroxy-4-Methyl-2-Oxoglutarate Aldolase From *Pseudomonas ochraceae* NGJ1," Biosei. Biotechnol. Biochem., 65 (12), pp. 2701-2709, 2001.

XP002391850, "*Acinetobacter baumannii* protein #3236," retrieved from EBI accession No. GSP: ADA36075 (Nov. 20, 2003).

XP002391851, Demethylmenaquinone methyltransferase (AGR_pAT_472p), retrieved from EBI accession No. UNIPROT:Q8UJZ5 (Jun. 1, 2002).

Interference No. 105,696 Kawahara Preliminary Motion 4 (37 C.F.R. § 41.121(a)(1)(ii) Motion to Deny Abraham Benefit of U.S. Appl. No. 60/374,831 for Lack of Enablement and Written Description) and the exhibits cited therein.

Interference No. 105,696 Abraham Opposition 4 (Opposing Kawahara's Attack on Abraham's Accorded Benefit) and the exhibits cited therein.

Interference No. 105,696 Kawahara Reply No. 4 (In Support of Kawahara's Motion to Deny Abraham Benefit of U.S. Appl. No. 60/374,831 for Lack of Enablement and Written Description) and the exhibits cited therein.

Interference No. 105,696 Abraham Motion 1 (Seeking Judgment That Kawahara's Involved Claims Lack Written Description) and the exhibits cited therein.

Interference No. 105,696 Kawahara Opposition to Abraham Motion 1 and the exhibits cited therein.

Interference No. 105,696 Abraham Reply 1 (Seeking Judgment That Kawahara's Involved Claims Lack Written Description) and the exhibits cited therein.

Interference No. 105,696 Abraham Motion 2 (Seeking Judgment That Kawahara's Involved Claims Are Not Enabled) and the exhibits cited therein.

Interference No. 105,696 Kawahara Opposition No. 2 (opposing judgment that Kawahara's involved claims are not enabled) and the exhibits cited therein.

Interference No. 105,696 Abraham Reply 2 (Seeking Judgment That Kawahara's Involved Claims Are Not Enabled) and the exhibits cited therein.

U.S. Appl. No. 10/979,821 filed Nov. 3, 2004 (The Abraham '821 application) (Abraham Exhibit No. 1001 filed in Patent Interference No. 105,696).

U.S. Patent No. 7,064,219 B2 issued Jun. 20, 2006 (the Kawahara '219 patent)(Abraham Exhibit No. 1002 filed in Patent Interference No. 105,696).
Certified English Translation of JP 2001-396300 (Abraham Exhibit No. 1004 filed in Patent Interference No. 105,696).
Certified English Translation of JP 2002-149069 (Abraham Exhibit No. 1005 filed in Patent Interference No. 105,696).
Certified English Translation of JP 2002-149078 (Abraham Exhibit No. 1006 filed in Patent Interference No. 105,696).
Certified English Translation of JP 2002-182032 (Abraham Exhibit No. 1007 filed in Patent Interference No. 105,696).
Abraham Exhibit No. 1008 filed in Patent Interference No. 105,696: "Declaration of Alexander M. Klibanov, Ph.D."
Abraham Exhibit No. 1009 filed in Patent Interference No. 105,696: "Curriculum Vitae of Alexander M. Klibanov, Ph.D."
Abraham Exhibit No. 1010 filed in Patent Interference No. 105,696: "Declaration of Timothy F. Jamison, Ph.D."
Abraham Exhibit No. 1011 filed in Patent Interference No. 105,696: "Curriculum Vitae of Timothy F. Jamison, Ph.D."
The Condensed Chemical Dictionary 989 (10th ed. 1981) (Abraham Exhibit No. 1012 filed in Patent Interference No. 105,696).
Hideaki Yamada and Sakayu Shimizu, Angew. Chem. Int. Ed. Engl. ,27:622-642 (1988) (Abraham Exhibit No. 1013 filed in Patent Interference No. 105,696).
Alexander M. Klibanov, Nature, 409:241-246 (2001) (Abraham Exhibit No. 1014 filed in Patent Interference No. 105,696).
U.S. Patent No. 5,994,559 issued Nov. 30, 1999 (Abraham Exhibit No. 1015 filed in Patent Interference No. 105,696).
Robert Thornton Morrison and Robert Neilson Boyd, Organic Chemistry 729 (6th ed., Prentice-Hall, Inc. 1992) (Abraham Exhibit No. 1017 filed in Patent Interference No. 105,696).
Robert Thornton Morrison and Robert Neilson Boyd, Organic Chemistry 809-810 (6th ed., Prentice-Hall, Inc. 1992) (Abraham Exhibit No. 1018 filed in Patent Interference No. 105,696).
Robert Thornton Morrison and Robert Neilson Boyd, Organic Chemistry 831 (6th ed., Prentice-Hall, Inc. 1992) (Abraham Exhibit No. 1019 filed in Patent Interference No. 105,696).
http://www.uspto.gov/web/offices/dcom/bpai/bpaifaq.htm#4 downloaded Oct. 19, 2009 (Abraham Exhibit No. 1020 filed in Patent Interference No. 105,696).
C. H. Wong and G. M. Whitesides, General Aspects in Enzymes in Synthetic Organic Chemistry 1-40 (Elsevier Science Ltd. 1994) (Abraham Exhibit No. 1023 filed in Patent Interference No. 105,696).
Lewis B. Lockwood, *Production of Organic Acids by Fermentation in* Microbioal Technology 355-387 (H. J. Peppler and D. Perlman eds., Academic Press 1979) (Abraham Exhibit No. 1024 filed in Patent Interference No. 105,696).
John C. Kotz et al., *Chemistry of Life in* The Chemical World—Concepts and Applications 905-954 (Harcourt Brace & Company 1994) (Abraham Exhibit No. 1025 filed in Patent Interference No. 105,696).
Donald Voet and Judith G. Voet, *Introduction to Enzymes in* Biochemistry 332-344 (2nd ed., John Wiley & Sons, Inc. 1995) (Abraham Exhibit No. 1026 filed in Patent Interference No. 105,696).
Donald Voet and Judith G. Voet, *Citric Acid Cycle in* Biochemistry 538-562 (2nd ed., John Wiley & Sons, Inc. 1995) (Abraham Exhibit No. 1027 filed in Patent Interference No. 105,696).
John R. Whitaker, Enzyme Purification in Principles of Enzymology for the Food Sciences 65-121 (Marcel Dekker, Inc. 1972) (Abraham Exhibit No. 1028 filed in Patent Interference No. 105,696).
Bo Ersson et al., *Introduction to Protein Purification in* Protein Purification—Principles, High Resolution Methods, and Applications 3-32, (Jan-Christer Janson and Lars Rydén eds., VCH Publishers, Inc. 1989) (Abraham Exhibit No. 1029 filed in Patent Interference No. 105,696).
Roger L. Lundblad, Ph.D. and Claudia M. Noyes, Ph.D., The Chemical Modification of Proteins in Chemical Reagents for Protein Modification vol. 1, at 1-23 (CRC Press, Inc. 1984) (Abraham Exhibit No. 1030 filed in Patent Interference No. 105,696).
John Rossi and Mark Zoller, *Site-Specific and Regionally Directed Mutagenesis of Protein-Encoding Sequences in* Protein Engineering 51-63 (Dale L. Oxender and C. Fred Fox eds., Alan R. Liss, Inc. 1987) (Abraham Exhibit No. 1031 filed in Patent Interference No. 105,696).

B. Nidetzky et al., *Stability and stabilization of glucose-fructose oxidoreductase from Zymomonas mobilis against irreversible inactivation during substrate turnover in biochemical reactors in* Stability and Stabilization of Biocatalysts 19-26 (A. Ballesteros et al. eds., Elsevier Science B.V. 1998) (Abraham Exhibit No. 1032 filed in Patent Interference No. 105,696).
Michael D. Trevan, *Techniques of Immobilization in* Immobilized Enzymes—An Introduction and Applications in Biotechnology 1-10 (John Wiley & Sons Ltd.1980) (Abraham Exhibit No. 1033 filed in Patent Interference No. 105,696).
P. F. Stanbury, *Culturing Micro-organisms for Production in* Biotechnology: The Biological Principles, Section III, at 63-107 (M. D. Trevan, et al. 1987) (Abraham Exhibit No. 1034 filed in Patent Interference No. 105,696).
Douglas C. Neckers and Michael P. Doyle, *Amino acids and proteins in* Organic Chemistry 972-1016 (John Wiley & Sons, Inc. 1977) (Abraham Exhibit No. 1035 filed in Patent Interference No. 105,696).
Francis A. Carey and Richard J. Sundberg, Advanced Organic Chemistry Contents of Part B (4th ed., Kluwer Academic/Plenum Publishers 2001) (Abraham Exhibit No. 1036 filed in Patent Interference No. 105,696).
Robert Thornton Morrison and Robert Neilson Boyd, Organic Chemistry 805-807 (6th ed., Prentice-Hall, Inc. 1992) (Abraham Exhibit No. 1037 filed in Patent Interference No. 105,696).
J. W. Cornforth et al., Biochem J., 68(1):57-61 (1957) (Abraham Exhibit No. 1038 filed in Patent Interference No. 105,696).
U.S. Patent No. 4,935,507 issued Jun. 19, 1990 (Abraham Exhibit No. 1039 filed in Patent Interference No. 105,696).
Abraham Exhibit No. 1040 filed in Patent Interference No. 105,696 "Annotated Figure 1".
http://www.webchem.net/notes/how_far/kinetics/rate_factors.htm downloaded Oct. 15, 2009 (Abraham Exhibit No. 1041 filed in Patent Interference No. 105,696).
Encyclopedia of Chemical Technology 3, at 245 (Raymond E. Kirk and Donald F. Othmer eds. 1949) (Abraham Exhibit No. 1042 filed in Patent Interference No. 105,696).
Encyclopedia of Chemical Technology 3, at 251 (Raymond E. Kirk and Donald F. Othmer eds. 1949) (Abraham Exhibit No. 1043 filed in Patent Interference No. 105,696).
Kai Julius Pedersen, *The Uncatalysed and the Metal-Ion Catalysed Decarboxylation of Oxaloacetic Acid in* Acta Chemica Scandinavica, 6:285-303 (1952) (Abraham Exhibit No. 1044 filed in Patent Interference No. 105,696).
Rudolph Steinberger and F. H. Westheimer, *Metal Ion-catalyzed Decarboxylation: A Model for an Enzyme System*, J. Am. Chem. Soc, 73:429-435 (1951) (Abraham Exhibit No. 1045 filed in Patent Interference No. 105,696).
Abraham Exhibit No. 1046 filed in Patent Interference No. 105,696: "Examiner Interview Summary, dated Feb. 11, 2009 in U.S. Appl. No. 10/979,821".
Abraham Exhibit No. 1047 filed in Patent Interference No. 105,696: "Request for Interference with Appendices A-K, filed Apr. 3, 2009 in U.S. Appl. No. 10/979,821".
U.S. Appl. No. 60/374,831, filed Apr. 23, 2002 (Abraham Exhibit No. 1048 filed in Patent Interference No. 105,696).
Abraham Exhibit No. 1051 filed in Patent Interference No. 105,696: "Deposition Transcript of Erik J. Sorensen, Ph.D., Nov. 24, 2009".
John C. Kotz et al., Principles of Reactivity: Kinetics and Equilibrium in The Chemical World—Concepts and Applications 295-349 (Harcourt Brace & Company 1994) (Abraham Exhibit No. 1052 filed in Patent Interference No. 105,696).
Richard H. Wiley and Ki-Soo Kim, J. Org. Chem., 38(20):3582-3585 (1973) (Abraham Exhibit No. 1055 filed in Patent Interference No. 105,696).
Abraham Exhibit No. 1063 filed in Patent Interference No. 105,696: "Deposition Transcript of Dwight E. Matthews, Dec. 11, 2009".
*Barany* v. *McGall*, Interference No. 105,351, Paper No. 59 (Bd. Pat. App. & Int. Feb. 6, 2009) (Abraham Exhibit No. 1069 filed in Patent Interference No. 105,696).
Abraham Exhibit No. 1070 filed in Patent Interference No. 105,696: "Second Declaration of Alexander M. Klibanov, Ph.D."
Abraham Exhibit No. 1071 filed in Patent Interference No. 105,696: "Second Declaration of Timothy F. Jamison, Ph.D."

Abraham Exhibit No. 1072 filed in Patent Interference No. 105,696: "Deposition Transcript of Jon D. Stewart, Ph.D., Jan. 19, 2010".
Abraham Exhibit No. 1073 filed in Patent Interference No. 105,696: "Deposition Transcript of Erik J. Sorensen, Ph.D., Jan. 22, 2010J".
Abraham Exhibit No. 1076 filed in Patent Interference No. 105,696: "Third Declaration of Alexander M. Klibanov, Ph.D."
Abraham Exhibit No. 1077 filed in Patent Interference No. 105,696: "Third Declaration of Timothy F. Jamison, Ph.D."
Manual of Patent Examining Procedure, 8th ed., Rev. 2, May 2004, § 608.01(p) (Abraham Exhibit No. 1078 filed in Patent Interference No. 105,696).
Manual of Patent Examining Procedure, 8th ed., Rev. 3, Aug. 2005, § 608.01(p) (Abraham Exhibit No. 1081 filed in Patent Interference No. 105,696).
Manual of Patent Examining Procedure, 8th ed., Rev. 4, Oct. 2005, § 608.01(p) (Abraham Exhibit No. 1082 filed in Patent Interference No. 105,696).
U.S. Patent No. 7,064,219 B2 (Kawahara Exhibit No. 2001 filed in Patent Interference No. 105,696).
Kawahara Exhibit No. 2003 filed in Patent Interference No. 105,696: "Declaration of Interference, filed Jun. 25, 2009 (Paper 1)".
Kawahara Exhibit No. 2006 filed in Patent Interference No. 105,696: "Abraham's Clean Copy of Claims (Paper 12)".
Kai Julius Pedersen, "The Uncatalyzed and the Metal-Ion Catalyzed Decarboxylation of Oxaloacetic Acid," *Acta Chem. Scandinavica*, vol. 6, pp. 235-303 (1952) (Kawahara Exhibit No. 2010 filed in Patent Interference No. 105,696).
Richard H. Wiley, et al., "The Biomolecular Decarboxylative Self-Condensation of Oxaloacetic Acid to Citroylformic Acid and Its Conversion by Oxidative Decarboxylation to Citric Acid," *J. Org Chem*. vol. 38, pp. 3582-3585 (1973) (Kawahara Exhibit No. 2014 filed in Patent Interference No. 105,696).
The original and a certified translation of Kawahara's Japanese priority application JP 2001-396300 ("JP '300"), filed Dec. 27, 2001 (Kawahara Exhibit No. 2022 filed in Patent Interference No. 105,696).
The original and a certified translation of Kawahara's Japanese priority application JP 2002-149069 ("JP '069"), filed May 23, 2002 (Kawahara Exhibit No. 2023 filed in Patent Interference No. 105,696).
The original and a certified translation of Kawahara's Japanese priority application JP 2002-149078 ("JP '078"), filed May 23, 2002 (Kawahara Exhibit No. 2024 filed in Patent Interference No. 105,696).
The original and a certified translation of Kawahara's PCT application No. PCT/JP02/12473 ("PCT '473"), published as WO 2003-059865 and filed Nov. 29, 2002 (Kawahara Exhibit No. 2026 filed in Patent Interference No. 105,696).
Kawahara Exhibit No. 2039 filed in Patent Interference No. 105,696: "Specification, U.S. Appl. No. 60/374,831".
Kawahara Exhibit No. 2040 filed in Patent Interference No. 105,696: "Declaration of Dwight E. Matthews".
Kawahara Exhibit No. 2044 filed in Patent Interference No. 105,696: "Declaration of Profession Erik J. Sorensen for Motion" No. 4.
Kawahara Exhibit No. 2045 filed in Patent Interference No. 105,696: "Declaration of Kenichi Mori-IHOG".
Kawahara Exhibit No. 2046 filed in Patent Interference No. 105,696: "Declaration of Toshimi Mizukoshi".
Kawahara Exhibit No. 2047 filed in Patent Interference No. 105,696: "LC/MS/MS Fragments Analysis of Standard IHOG and IHOG-b by Triple Q Type Mass Spectrometer, Toshimi Mizukoshi, Oct. 5, 2009".
Kawahara Exhibit No. 2048 filed in Patent Interference No. 105,696: "LC/MS/MS Analysis of Standard IHOG, and Comparison of its Fragments Data With Those Reported in Cargill's Provisional Application, Toshimi Mizukoshi, Sep. 2, 2009".
Kawahara Exhibit No. 2049 filed in Patent Interference No. 105,696: "IHOG-b Mass Spectrum, Aug. 27, 2009".
Kawahara Exhibit No. 2050 filed in Patent Interference No. 105,696: "Structures of IHOG and IHOG-b".
Kawahara Exhibit No. 2055 filed in Patent Interference No. 105,696: "Material Safety Data Sheet n-Butyllithium Isopar C".
Kawahara Exhibit No. 2056 filed in Patent Interference No. 105,696: "Material Safety Data Sheet Lithium Diisopropylamide in THF/Heptane".
Kawahara Exhibit No. 2057 filed in Patent Interference No. 105,696: "Material Safety Data Sheet LHS in THF/2-Methylbutene".
Kawahara Exhibit No. 2058 filed in Patent Interference No. 105,696: "Declaration of Professor Jon D. Stewart".
Kawahara Exhibit No. 2059 filed in Patent Interference No. 105,696: "CV of Professor Jon D. Stewart".
Kawahara Exhibit No. 2060 filed in Patent Interference No. 105,696: "List of Materials Reviewed by Professor Jon D. Stewart".
Kawahara Exhibit No. 2063 filed in Patent Interference No. 105,696: "Deposition Transcript of Alexander Klibanov, Ph.D. taken Nov. 21, 2009".
D.C. Demirjian, et al., "Screening for Novel Enzymes," Fessner Ed., Biocatalysis From Discovery to Application, pp. 1-29 (2000) (Kawahara Exhibit No. 2065 filed in Patent Interference No. 105,696).
C.L. Buchanan, et al., "An extremely thermostable aldolase from *Sulfolobus solfataricus* with specificity for non-phosphorylated substrates," Biochem. J. vol. 343, pp. 563-570 (1999) (Kawahara Exhibit No. 2066 filed in Patent Interference No. 105,696).
Carey and Sundberg Eds., Advanced Organic Chemistry, Second Edition, Part A: Structure and Mechanisms, pp. 421-426 (1984) (Kawahara Exhibit No. 2067 filed in Patent Interference No. 105,696).
D.C. Demirjian, et al, "Enzymes from extremophiles," Curr. Opin. Chem. Biol., Viol. 5, pp. 144-151 (2001) (Kawahara Exhibit No. 2068 filed in Patent Interference No. 105,696).
Baldwin and Magnus Eds., Tetrahedron Organic Chemistry Series vol. 12 Wong and Whitesides Eds., Enzymes in Synthetic Organic Chemistry, pp. 195-251 (Kawahara Exhibit No. 2070 filed in Patent Interference No. 105,696), 1995.
K. Faber Ed., Biotransformations in Organic Chemistry $2^{nd}$ Ed., pp. 52-105; 219-232 (1995) (Kawahara Exhibit No. 2071 filed in Patent Interference No. 105,696).
W.D. Fessner and V. Helaine, "Biocatalytic synthesis of hydroxylated natural products using aldolases and related enzymes," Curr. Opin. Biotechnol., vol. 12, pp. 574-586 (2001) (Kawahara Exhibit No. 2072 filed in Patent Interference No. 105,696).
W.D. Fessner and C. Walter, "Enzymatic C-C Bond Formation in Asymmetric Synthesis," Topics in Curr. Chem., vol. 184, pp. 97-194 (1996) (Kawahara Exhibit No. 2073 filed in Patent Interference No. 105,696).
N.C. Floyd, et al., "A Simple Strategy for obtaining both Enantiomers from an Aldolase Reaction: Preparation of L- and D-4-Hydroxy-2-ketoglutarate," J. Chem. Soc. Perkin Trans., vol. 1, pp. 1085-1086 (1992) (Kawahara Exhibit No. 2074 filed in Patent Interference No. 105,696).
Z.G. Hajos and D.R. Parrish, "Asymmetric Synthesis of Bicyclic Intermediates of Natural Product Chemistry," J. Org. Chem., vol. 39, No. 2, pp. 1615-1621 (1974) (Kawahara Exhibit No. 2075 filed in Patent Interference No. 105,696).
E. Kimura, et al., "Dynamic Enolate Recognition in Aqueous Solution by Zinc (II) in a Phenacyle-Pendant Cyclen Complex: Implications for the Role of Zinc(II) in Class II Aldolases," J. Am. Chem. Soc., vol. 121, pp. 1267-1274 (1999) (Kawahara Exhibit No. 2078 filed in Patent Interference No. 105,696).
Kawahara Exhibit No. 2079 filed in Patent Interference No. 105,696 "Diversa Flow Chart".
Kawahara Exhibit No. 2081 filed in Patent Interference No. 105,696: "Complete Specification, U.S. Appl. No. 60/374,831".
A.M. Klibanov, "Improving enzymes by using them in organic solvents," Nature, vol. 409, pp. 241-246 (2001) (Kawahara Exhibit No. 2089 filed in Patent Interference No. 105,696).
N. Kumagai, et al. "Direct Catalytic Enantio- and Diastereoselective Aldol Reaction Using a Zn-Zn-Linked-BINOL Complex: A Practical Synthesis of syn-1,2-Diols," Organic Letters, vol. 3, No. 10, pp. 1539-1542 (2001) (Kawahara Exhibit No. 2090 filed in Patent Interference No. 105,696).

Y. Li, et al., "Dipeptide Serryl-Histidine and Related Oligopeptides Cleave DNA, Protein, and a Carboxyl Ester," Bioorg. Med. Chem., vol. 8, pp. 2675-2680 (2000) (Kawahara Exhibit No. 2091 filed in Patent Interference No. 105,696).

B. List, "Asymmetric Aminocatalysis," Synlett, No. 11, pp. 1675-1686 (2001) (Kawahara Exhibit No. 2092 filed in Patent interference No. 105,696).

J.Q. Liu et al., A new route to L-threo-3-[4-(methylthio) phenylserine], a key intermediate for the synthesis of antibiotics Kawahara Exhibit No. 2093 filed in Patent Interference No. 105,696, Appl Microbiol Biotechnol, 1999, 51: 586-591.

T.D. Machajewksi and C.H. Wong, "The Catalytic Asymmetric Aldol Reaction," Agnew. Chem. Int. Ed., vol. 39, pp. 1352-1374 (2000) (Kawahara Exhibit No. 2094 filed in Patent Interference No. 105,696).

K. Maruyama, "Purification and Properties of 4-Hydroxy-4-Methyl-2-Oxoglutarate Aldolase from *Pseudomonas ochraceae* Grown on Phthalate," J. Biochem, vol. 108, pp. 327-333 (1990) (Kawahara Exhibit No. 2095 filed in Patent Interference No. 105,696).

M. Nakagawa, et al., "Steric Effects of Chiral Ligands in a New Type of Aldol Condensations Catalyzed by Zinc(II) Complexes of a-Amino Acid Esters," Chemistry Letters, pp. 391-394 (1985) (Kawahara Exhibit No. 2097 filed in Patent Interference No. 105,696).

R. Pollero, et al., "Lipolytic Activity in Free and Immobilized Cells of *Phoma glomerata*," JAOCS, vol. 74, pp. 451-454 (1997) (Kawahara Exhibit No. 2099 filed in Patent Interference No. 105,696).

J.D. Stewart and S.J. Benkovic, "Catalytic Antibodies: Mechanistic and Practical Considerations," Che. Soc. Rev., pp. 213-219 (1993) (Kawahara Exhibit No. 2101 filed in Patent Interference No. 105,696).

J.D. Stewart and S. Rodriguez, "Cloning, Structure, and Activity of Ketone Reductases from Baker's Yeast," H.A. Kirst et al. Eds., Enzyme Technologies for Pharmaceutical and Biotechnological Applications, pp. 175-207 (2001) (Kawahara Exhibit No. 2102 filed in Patent Interference No. 105,696).

T. Sugai, et al., "Improved Enzymatic Procedure for a Preparative-Scale Synthesis of Sialic Acid and KDN," Bull. Chem. Soc. Jpn., vol. 68, pp. 3581-3589 (1995) (Kawahara Exhibit No. 2103 filed in Patent Interference No. 105,696).

J. Suh, "Model Studies of Metalloenzymes Involving Metal Ions as Lewis Acid Catalysts," Acc. Chem. Res., vol. 25, No. 7, pp. 273-279 (Kawahara Exhibit No. 2104 filed in Patent Interference No. 105,696), 1992.

S. Takayama, et al., "Microbal Aldolases and Transketolases: New Biocatalytic Approaches to Simple and Complex Sugars," Annu. Rev. Microbiol., vol. 51, pp. 285-310 (1997) (Kawahara Exhibit No. 2105 filed in Patent Interference No. 105,696).

B.M. Trost and H. Ito, "A Direct Catalytic Enantioselective Aldol Reaction via a Novel Catalyst Design," J. Am. Chem. Soc., vol. 122, pp. 12003-12004 (2000) (Kawahara Exhibit No. 2106 filed in Patent Interference No. 105,696).

B.M. Trost, et al., "Communications to the Editor, Asymmetric Aldol Reaction via a Dinuclear Zinc Catalyst a-Hydroxyketones as Donors," J. Am. Chem. Soc., vol. 123, pp. 3367-3368 (2001) (Kawahara Exhibit No. 2107 filed in Patent Interference No. 105,696).

R. Vleggaar, et al., "Structure Elucidation of Monatin, a High-intensity Sweetener Isolated from the Plant *Schlerochiton ilicifolius*," J. Chem. Soc. Perkin Trans., pp. 3095-3098 (1992) (Kawahara Exhibit No. 2108 filed in Patent Interference No. 105,696).

Walsh Ed., Enzymatic Reaction Mechanisms, pp. 745-759 (1979) (Kawahara Exhibit No. 2109 filed in Patent Interference No. 105,696).

J.G.J. Weijnen and Arie Koudijs, "Synthesis of Chiral 1,10-Phenanthroline Ligands and the Activity of Metal-Ion Complexes in the Enantioselective Hydrolysis of N-Protected Amino Acid Esters," J. Org. Chem., vol. 57, pp. 7258-7265 (1992) (Kawahara Exhibit No. 2110 filed in Patent Interference No. 105,696).

N. Yoshikawa, et al., "Direct Catalytic Asymmetric Aldol Reaction," J. Am. Chem. Soc., vol. 121, pp. 4168-4178 (1999) (Kawahara Exhibit No. 2112 filed in Patent Interference No. 105,696).

A. Zaks and A.M. Klibanov, "Enzymatic Catalysis in Organic Media at 100° C.," Science, vol. 224, pp. 1249-1251 (1984) (Kawahara Exhibit No. 2113 filed in Patent Interference No. 105,696).

Kawahara Exhibit No. 2114 filed in Patent Interference No. 105,696: "Declaration of Professor Erik J. Sorensen".

C. Schopf and K. Thierfelder, "The aldol condensation between aldehydene and B-keto acids and its importance for the biogenesis of some natural materials," Justus Liebig's Annalen der Chemie, vol. 518, Issue 1, pp. 127-155 (1935) (Kawahara Exhibit No. 2116 filed in Patent Interference No. 105,696).

G. Buldain et al., "Carbon-13 Nuclear Magnetic Resonance Spectra of the Hydrate, Keto and Enol Forms of Oxalacetic Acid," Mag. Reson. Chem., vol. 23, pp. 478-481 (1985) (Kawahara Exhibit No. 2124 filed in Patent Interference No. 105,696).

C.S. Tsai, "Spontaneous Decarboxylation of oxalacetic acid," Can. J. Chem., vol. 45, pp. 873-880 (1967) (Kawahara Exhibit No. 2126 filed in Patent Interference No. 105,696).

Kawahara Exhibit No. 2130 filed in Patent Interference No. 105,696: "Deposition Transcript of Timothy Jamison Deposition, Ph.D. taken Nov. 20, 2009".

S.A. Margolis, "Identification and Quantitatior of the Impurities in Sodium Pyruvate," Anal. Chem., vol. 58, pp. 2504-2510 (1986) (Kawahara Exhibit No. 2131 filed in Patent Interference No. 105,696).

U.S. Appl. No. 10/872,573 (Kawahara Exhibit No. 2133 filed in Patent Interference No. 105,696).

J.Q. Liu et al., "Diversity of microbial threonine aldolases and their application," J. Mol. Catalysis B: Enzymatic, vol. 10, pp. 107-115 (2000) (Kawahara Exhibit No. 2134 filed in Patent Interference No. 105,696).

K. Juhl, et al., "Catalytic asymmetric homo-aldol reaction of pyruvate—a chiral Lewis acid catalyst that mimics aldolase enzymes," Chem. Comm., 2000, pp. 2211-2212 (Kawahara Exhibit No. 2135 filed in Patent Interference No. 105,696).

N. Passerat and J. Bolte, "Large-Scale Enzymatic Synthesis of Diastereoisomeric y-Hydroxy L-Glutamic Acids," Tetrahedron Letters, vol. 28, No. 12, pp. 1277-1280 (1987) (Kawahara Exhibit No. 2136 filed in Patent Interference No. 105,696).

*Understanding Recent Case Law on Enablement*, IP360.com (Dec. 21, 2009), at http://ip.law360.com/articles/138249 (Kawahara Exhibit No. 2137 filed in Patent Interference No. 105,696).

Kawahara Exhibit No. 2139 filed in Patent Interference No. 105,696: "Erik J. Sorensen deposition transcript of Nov. 24, 2009 and Errata sheet".

Kawahara Exhibit No. 2143 filed in Patent Interference No. 105,696: "Diagram drawn by Timothy F. Jamison during his Jan. 29, 2010 deposition".

Kawahara Exhibit No. 2147 filed in Patent Interference No. 105,696: "Jan. 27, 2010, deposition transcript of Alexander Klibanov".

Kawahara Exhibit No. 2148 filed in Patent Interference No. 105,696: "Jan. 29, 2010, deposition transcript of Timothy Jamison".

Kawahara Exhibit No. 2041 filed in Patent Interference No. 105,696: "Dwight E. Matthews' CV".

Kawahara Exhibit No. 2042 filed in Patent Interference No. 105,696: "List of Materials Reviewed by Dwight E. Matthews".

Kawahara Exhibit No. 2043 filed in Patent Interference No. 105,696: "HPLC for IHOG-B Original and Certified Translation".

Kawahara Exhibit No. 2051 filed in Patent Interference No. 105,696: "IHOG-b H-NMR Original and Certified Translation".

Tack, B.F., et al. "Purification and Properties of 4-Hydroxy-4-methyl-2-oxoglutarate Aldolase," Journal of Biological Chemistry, vol. 247, No. 20, 1972. pp. 6444-6449, XP002389488.

Maruyama, K. "Purification and Properties of 4-Hydroxy-4-Methyl-2-Oxoglutarate Aldolase from *Pseudomonas ochraceae* Grown on Phthalate," Journal of Biochemistry, vol. 108, No. 2, 1990, pp. 327-333, XP 002048447.

Patil, R.V., et al. "Cloning, Nucleotide Sequence, Overexpression, and Inactivation of the *Excherichia coli* 2-Keto-4-Hydroxyglutarate Aldolase Gene," Journal of Bacteriology, vol. 174, No. 1, Jan. 1992, pp. 102-107, XP008020729.

Liu, J.Q., et al., "Gene Cloning, Biochemical Characterization and Physiological Role of a Thermostable Low-Specificity L-Threonine Aldolase from *Escherichia coli*," European Journal of Biochemistry, vol. 255, No. 1, Jul. 1998, pp. 220-226, XP002389489.

Liu, J.Q., et al. "Low-Specificity L-Threonine Aldolase of *Pseudomonas* sp. NCIMB 10558: Purification, Characterization and its Application of β-hydroxy-α-amino Acid Synthesis," Applied Microbiology and Biotechnology, vol. 49, No. 6, Jun. 1998, pp. 702-708, XP002389490.

Leung, P.T., et al. Purification and Properties of 4-Hydroxy-2-Ketopimelate Aldolase from Acinetobacter, Journal of Bacteriology, vol. 120, No. 1, 1974, pp. 168-172, XP002389491.

Fessner, W.D., et al. "Biocatalytic Synthesis of Hydroxylated Natural Products Using Aldolases and Related Enzymes," Current Opinion in Biotechnology, vol. 12, No. 6, Dec. 2001, pp. 574-586, XP002389492.

European Search Report issued Dec. 2, 2010, in Application No. 10177313.3-2405.

G. Buldain, et al., "Carbon-13 Nuclear Magnetic Resonance Spectra of the Hydrate, Eto and Enol Forms of Oxalacetic Acid", Magnetic Resonance in Chemistry, 1985, vol. 23, No. 6, pp. 478-481.

D. Oliveira, et al., "Diastereoselective Formation of a Quaternary Center in a Pyroglutamate Derivative. Formal Synthesis of Monatain", Tetrahedron Letters, vol. 42, 2001, pp. 6793-6796.

K. Nakamura, et al., "Total Synthesis of Monatin", Organic Letters, vol. 2, No. 19, 2000, pp. 2967-2970.

C. Holzapfel, "A Simple Cycloaddition Approach to a Racemate of the Natural Sweetener Monatin", Synthetic Communications, vol. 24, No. 22, 1994, pp. 3197-3211.

C. Holzapfel, "The Synthesis of a γ-Keto-α-Amino Acid, A Key Intermediate in the Synthesis of Monatin, A New Natural Sweetener", Synthetic Communications, vol. 23, No. 18, 1993, pp. 2511-2526.

R. Wiley, et al., "The Bimolecular Decarboxylative Self-Condensation of Oxaloacetic Acid to Citroylformic Acid and Its Conversion by Oxidative Decarboxylation to Citric Acid", J. Org. Chem., vol. 38, No. 20, 1973, pp. 3582-3585.

D. Leussing, et al., "A Nuclear Magnetic Resonance Study of Aqueous Pyruvate-Glycinate-Zinc(II) and Related Systems", Journal of American Chemical Society, vol. 86, Jul. 20, 1964, pp. 2805-2810.

S. Margolis, et al., "Identification and Quantitatior of the Impurities in Sodium Pyruvate", Analytical Chemistry, vol. 58, No. 12, 1986, pp. 2504-2510.

N. Passerate, et al., "Large Scale Enzymatic Synthesis of Diastereoisomeric -Hydroxy L-Glutamic Acids", Tetrahedron Letters, vol. 28, No. 12, 1987, pp. 1277-1280.

Dambruoso, et al "Efficiency in Isotetronic Acid Synthesis via a Diamine—Acid Couple Catalyzed Ethyl Pyruvate Homoaldol Reaction," Organic Letters, vol. 7, No. 21, 2005, pp. 4657-4660.

Van Ophem, et al. "Catalytic Ability and Stability of Two Recombinant Mutants of D-Amino Acid Transaminase Involved in Coenzyme Binding," Protein Science, 4, 1995, pp. 2578-2586, XP-002383317.

Abraham et al., 2003, CAS: 139:36397.

Interference No. 105,696: Kawahara's Reply No. 1 (In support of Kawahara's Request to Designate Claim 5 As Corresponding to the Court) and the exhibits cited therein.

Interference No. 105,696: Abraham Opposition 1 (Opposing Kawahara's Request to Designate Claim 5 As Corresponding to the Count) and the exhibits cited therein.

Interference No. 105,696: Kawahara's Preliminary Motion No. 1 (37 C.F.R. 41.208(a)(2) Motion to Designate Claim 5 of Patent 7,064,219 B2 as Corresponding to the Count and the exhibits cited therein.

Interference No. 105,696: Kawahara Preliminary Motion 2 (37 C.F.R. §41.121(a)(1)(ii) and §41.208(a)(3) Motion for Benefit of JP 2001-396300 filed Dec. 27, 2001; JP2002-149069, filed May 23, 2002, JP 2002-149078, filed May 23, 2002; JP-2002-182032, filed Jun. 21, 2002, and PCT/JP02/12473) and the exhibits cited therein.

Interference No. 105,696: Abraham Opposition 2 (Opposing Kawahara's Request for Benefit to Four Earlier Applications) and the exhibits cited therein.

Interference No. 105,696: Kawahara Reply No. 2 (Motion for Benefit of JP 2001-396300 Filed Dec. 27, 2001; JP2002-149069, filed May 23, 2002; JP 2002-149078, filed May 23, 2002; JP-2002-182032, filed Jun. 21, 2002, and PCT/JP02/12473) and the exhibits cited therein.

Interference No. 105,696: Kawahara's Preliminary Motion 3 (Pursuant to 37 C.F.R. § 41.121(a)(2) and 37 C.F.R. §1.324 to Correct the Inventorship of United States Patent No. 7,064,219) and the exhibits cited therein.

Interference No. 105,696: Abraham Opposition 3 (Opposing Kawahara's Request to Correct Inventorship for U.S. Patent No. 7,064,219) and the exhibits cited therein.

Interference No. 105,696 Kawahara Reply No. 3. and the exhibits cited therein.

Interference No. 105,696 Decision on Motions from the Board of Patent Appeals and Interferences, filed Sep. 30, 2011.

Interference No. 105.696 Abraham Reply 3 (to Substitute Count 1 with Proposed Count 2) and the exhibits cited therein.

Interference No. 105,696 Abraham Motion 3 (to Substitute Count 1 with Proposed Count 2) and the exhibits cited therein.

Interference No. 105,696 Kawahara's Opposition No. 3 (Corrected) (Opposing Abraham's Motion 3 to Substitute Count 1 with Proposed Count 2) and the exhibits cited therein.

Berendsen HJC, "A Glimpse of the Holy Grail?" Science, Oct. 23, 1998, 282: 642-643.

M.J. Pucci, et al. "*Staphylococcus haemolyticus* Contains Two D-Glutamic Acid Biosynthetic Activities, A Glutamate Racemase and a D-amino Acid Transaminase," Journal of Bacteriology, vol. 177, No. 2, Jan. 1995, pp. 336-342.

Kuramitsu, et al. "Aspartate Aminotransferase of *Escherichia coli*: Nucleotide Sequence of the aspC Gene," J. Biochem., 97, 1985, pp. 1259-1262.

Watson, et al. "Cloning and Nucleotide Sequencing of *Rhizobium meliloti* Aminotransferase Genes: an Aspartate Aminotransferase Required for Symbiotic Nitrogen Fixation is Atypical," Journal of Bacteriology, vol. 175, No. 7, Apr. 1993, pp. 1919-1928.

Novogrodsky, et al., "Control of Aspartate β-Decarboxylase Activity by Transamination," The Journal of Biological Chemistry, vol. 239, No. 3, Mar. 1964, pp. 879-888.

"Designing Custom Peptides," from SIGMA Genosys, pp. 1-2. Accessed Dec. 16, 2004.

Database UniProt [Online] "D-Alanine Aminotransferase (EC 2.6.1.21) (D-Aspartate Aminotransferase) (D-Amino Acid Aminotransferase) (D-Amino Acid Transaminase) (DAAT)," XP-002383319, Database accession No. DAAA_BACSH, Oct. 1, 1996.

Schinzel R, Druecks P, "The phosphate recognition site of *Escherichia coli* maltodexlrin phosphorylase," FEBS, Jul. 1991, 286(1,2): 125-128.

Branden et al., Introduction to Protein Structure, Garland Publishing Inc, New York pp. 247, 1991.

Witkowski et al., "Conversion of a β-Ketoacyl Synthase to a Malonyl Decarboxylase by Replacement of the Active-Site Cysteine with Glutamine" Biochemistry 38:11643-11650, 1999.

Seffernick et al., "Melamine Deaminase and Atrazine Chlorohydrolase: 98 Percent Identical but Functionally Different." J. Bacteriol. 183(8):2405-2410, 2001.

Extended Search Report issued Dec. 2, 2010, in EP Application No. 10177313.3.

Nakamura, et al., "Total Synthesis of Monatin," Organic Letters, XP002964364, vol. 2, No. 19, Jan. 1, 2000. pp. 2967-2970 (with Additions and Corrections page).

Gathergood, et al., "Direct catalytic asymmetric aldol reactions of pyruvates: scope and mechanism," Org. Biomol. Chem., vol. 2, 2004. pp. 1077-1085.

J. Rudinger, "Characteristics of the amino acids as components of a peptide hormone sequence," Peptide Hormones, JA Parsons Edition, University Park Press, Jun. 1976, pp. 1-7.

Communication of a Notice of Opposition in European Patent No. EP1445323, dated Oct. 31, 2011.

U.S. Appl. No. 13/250,359, filed Sep. 30, 2011, Sugiyama, et al.

U.S. Appl. No. 13/273,290, filed Oct. 14, 2011, Kawahara, et al.

Greene, T.W., et al. "Protection Groups in Organic Synthesis Third Edition," John Wiley, & Sons. Inc. 1999. pp. 127-132 383-387, 642-643.

Olesen, P., et al, "2(S), 4(R)-4-β-D-Galactopyranosyloxy)-4-Isobutyl-Glutsmic Acid: A New Amino Acid in Reseda Odorata." Phytochemistry, 1973, vol. 12, pp. 1713-1719.

Ezquerra, J., et al. "Stereoselective Double Alkylation of Ethyl N-Boc-pyroglutamate," J. Org. Chem., 1994, vol. 59, pp. 4327-4331.

International Search Report issued Apr. 13, 2004, in PCT/JP03/17016.

International Search Report issued Apr. 8, 2003, in PCT/JP02/12852.

Chinese Office Action issued Oct. 26, 2011, in Patent Application No. 200910163551.9 (with English translation).

Bentley, et al. "Some Chemical and Physiological Properties of 3-Indolylpyruvic Acid" Biochem, vol. 64. Dec. 31, 1956. pp. 44-49.

US 8,202,711 B2

SEQUENCE LISTING

```
<160> NUMBER OF SEQ ID NOS: 18

<210> SEQ ID NO 1
<211> LENGTH: 1296
<212> TYPE: DNA
<213> ORGANISM: Pseudomonas taetrolens
<220> FEATURE:
<221> NAME/KEY: CDS
<222> LOCATION: (444)..(1118)
<223> OTHER INFORMATION:
<220> FEATURE:
<221> NAME/KEY: CDS
<222> LOCATION: (456)..(1118)
<223> OTHER INFORMATION:

<400> SEQUENCE: 1
gtacaccgtc ctgactcagg gcgcgctcgg cacgggttga tctatgagcg ctgtttgccc      60
agaatgacgt cggggtcacg tacgatcaaa gcaactacct gatcgcccag tgggcctgac     120
ctgtccggtg tcggcatcag ctacctgcct cgccaagtgt ctctcgccat tggtggacca     180
gggtcgggct actagtcatc gaaaccgagc ctgcgctgcc tcccatccaa tacatcgccg     240
tacaccgcgc cgatcgtctt cagggcctca gcgtcgaggt tgcacgtctg gcagctcgtt     300
gctgtgattt cagccgcatg gtgtgtaac acaggcgctg gatacgagaa aaaaagcgat     360
```

```
gtatttttcat agataaatat cgctaatagt gccaagcgac ctttcttact atgaacgcat      420
agcccacaag ggttcagtca ttc atg gag gtc gct atg tca ttg ccc ggt tca      473
                          Met Glu Val Ala Met Ser Leu Pro Gly Ser
                           1               5                  10 cgc atc tac cct tct ccg ccc cag gca cca cgc tca ctg ctg gac gcg        521
Arg Ile Tyr Pro Ser Pro Pro Gln Ala Pro Arg Ser Leu Leu Asp Ala
                15                  20                  25 ttt cag aac gta gtg acg ccg cat atc agt gat aac ctc ggg cgt cac        569
Phe Gln Asn Val Val Thr Pro His Ile Ser Asp Asn Leu Gly Arg His
        30                  35                  40 atc ggt gcc cgg ggg ctg acg cgc tat aac cac acc ggc aaa ctg gtg        617
Ile Gly Ala Arg Gly Leu Thr Arg Tyr Asn His Thr Gly Lys Leu Val
    45                  50                  55 ggc acc gcc ctg acg gtg aag act cgc ccc ggc gac aac ctc tac atc        665
Gly Thr Ala Leu Thr Val Lys Thr Arg Pro Gly Asp Asn Leu Tyr Ile
60                  65                  70 tac aaa gca ctg acg ctg atc gaa ccc gga cac gtg ctg gtg atc gac        713
Tyr Lys Ala Leu Thr Leu Ile Glu Pro Gly His Val Leu Val Ile Asp
75                  80                  85                  90 gct cag ggt gac gcg acc aac gcg gtc att ggt gag ctg atc aag ctc        761
Ala Gln Gly Asp Ala Thr Asn Ala Val Ile Gly Glu Leu Ile Lys Leu
                95                 100                 105 tac gcg cag caa cgt ggc tgt gtc ggc ttc gtc gtc gac ggc gcc atc        809
Tyr Ala Gln Gln Arg Gly Cys Val Gly Phe Val Val Asp Gly Ala Ile
            110                 115                 120 cgc gat gtc gcc agt ttt gaa gat acg cct tgc tat gcc cgt agc gtg        857
Arg Asp Val Ala Ser Phe Glu Asp Thr Pro Cys Tyr Ala Arg Ser Val
        125                 130                 135 gtg cat tgc ggt ccc tac aaa agc ggc cca ggg gaa atc aat gtc ccg        905
Val His Cys Gly Pro Tyr Lys Ser Gly Pro Gly Glu Ile Asn Val Pro
    140                 145                 150 gtg tca atc ggc ggg atg atc atc aat ccg ggc gac atc att gtc ggt        953
Val Ser Ile Gly Gly Met Ile Ile Asn Pro Gly Asp Ile Ile Val Gly
155                 160                 165                 170 gac gag gat ggg ctg gtt gcc ttc tcg ccc gac cat gcc gag cag gtg       1001
Asp Glu Asp Gly Leu Val Ala Phe Ser Pro Asp His Ala Glu Gln Val
                175                 180                 185 ttg gtc aag gcg cga gag cat gac gcg cat gaa cag cag gtc aaa gcc       1049
Leu Val Lys Ala Arg Glu His Asp Ala His Glu Gln Gln Val Lys Ala
            190                 195                 200 gaa atc gcc act ggc gcc atc gat cag tca tgg ctg gac aaa gtg ctg       1097
Glu Ile Ala Thr Gly Ala Ile Asp Gln Ser Trp Leu Asp Lys Val Leu
        205                 210                 215 gaa aag gct ggc ctg gcg aac tgaaaaacac tgtgtaatcg ccttgctgca          1148
Glu Lys Ala Gly Leu Ala Asn
    220                 225 gcgacattgc tgtcggacag gatgatctga cgcttcagtt acgcgttctt gggtgcaccg     1208
cgccacgtca ggaagtggct gctgccgcat gcaggtgaca tgtcatgtac catggcagca     1268
gcacgtgaca tgcacgatgt gctcacgc                                        1296

<210> SEQ ID NO 2
<211> LENGTH: 225
<212> TYPE: PRT
<213> ORGANISM: Pseudomonas taetrolens

<400> SEQUENCE: 2

Met Glu Val Ala Met Ser Leu Pro Gly Ser Arg Ile Tyr Pro Ser Pro
1               5                  10                  15
```

```
Pro Gln Ala Pro Arg Ser Leu Leu Asp Ala Phe Gln Asn Val Val Thr
            20                  25                  30

Pro His Ile Ser Asp Asn Leu Gly Arg His Ile Gly Ala Arg Gly Leu
        35                  40                  45

Thr Arg Tyr Asn His Thr Gly Lys Leu Val Gly Thr Ala Leu Thr Val
50                  55                  60

Lys Thr Arg Pro Gly Asp Asn Leu Tyr Ile Tyr Lys Ala Leu Thr Leu
65                  70                  75                  80

Ile Glu Pro Gly His Val Leu Val Ile Asp Ala Gln Gly Asp Ala Thr
                85                  90                  95

Asn Ala Val Ile Gly Glu Leu Ile Lys Leu Tyr Ala Gln Gln Arg Gly
            100                 105                 110

Cys Val Gly Phe Val Val Asp Gly Ala Ile Arg Asp Val Ala Ser Phe
        115                 120                 125

Glu Asp Thr Pro Cys Tyr Ala Arg Ser Val Val His Cys Gly Pro Tyr
130                 135                 140

Lys Ser Gly Pro Gly Glu Ile Asn Val Pro Val Ser Ile Gly Gly Met
145                 150                 155                 160

Ile Ile Asn Pro Gly Asp Ile Ile Val Gly Asp Glu Asp Gly Leu Val
                165                 170                 175

Ala Phe Ser Pro Asp His Ala Glu Gln Val Leu Val Lys Ala Arg Glu
            180                 185                 190

His Asp Ala His Glu Gln Gln Val Lys Ala Glu Ile Ala Thr Gly Ala
        195                 200                 205

Ile Asp Gln Ser Trp Leu Asp Lys Val Leu Glu Lys Ala Gly Leu Ala
210                 215                 220

Asn
225

<210> SEQ ID NO 3
<211> LENGTH: 221
<212> TYPE: PRT
<213> ORGANISM: Pseudomonas taetrolens

<400> SEQUENCE: 3

Met Ser Leu Pro Gly Ser Arg Ile Tyr Pro Ser Pro Gln Ala Pro
1               5                   10                  15

Arg Ser Leu Leu Asp Ala Phe Gln Asn Val Val Thr Pro His Ile Ser
            20                  25                  30

Asp Asn Leu Gly Arg His Ile Gly Ala Arg Gly Leu Thr Arg Tyr Asn
        35                  40                  45

His Thr Gly Lys Leu Val Gly Thr Ala Leu Thr Val Lys Thr Arg Pro
50                  55                  60

Gly Asp Asn Leu Tyr Ile Tyr Lys Ala Leu Thr Leu Ile Glu Pro Gly
65                  70                  75                  80

His Val Leu Val Ile Asp Ala Gln Gly Asp Ala Thr Asn Ala Val Ile
                85                  90                  95

Gly Glu Leu Ile Lys Leu Tyr Ala Gln Gln Arg Gly Cys Val Gly Phe
            100                 105                 110

Val Val Asp Gly Ala Ile Arg Asp Val Ala Ser Phe Glu Asp Thr Pro
        115                 120                 125

Cys Tyr Ala Arg Ser Val Val His Cys Gly Pro Tyr Lys Ser Gly Pro
130                 135                 140

Gly Glu Ile Asn Val Pro Val Ser Ile Gly Gly Met Ile Ile Asn Pro
145                 150                 155                 160
```

```
Gly Asp Ile Ile Val Gly Asp Glu Asp Gly Leu Val Ala Phe Ser Pro
                165                 170                 175

Asp His Ala Glu Gln Val Leu Val Lys Ala Arg Glu His Asp Ala His
            180                 185                 190

Glu Gln Gln Val Lys Ala Glu Ile Ala Thr Gly Ala Ile Asp Gln Ser
        195                 200                 205

Trp Leu Asp Lys Val Leu Glu Lys Ala Gly Leu Ala Asn
    210                 215                 220
```

<210> SEQ ID NO 4
<211> LENGTH: 20
<212> TYPE: PRT
<213> ORGANISM: Pseudomonas taetrolens

<400> SEQUENCE: 4

```
Ser Leu Leu Asp Ala Phe Gln Asn Val Val Thr Pro His Ile Ser Asp
1               5                   10                  15

Asn Leu Gly Arg
            20
```

<210> SEQ ID NO 5
<211> LENGTH: 12
<212> TYPE: PRT
<213> ORGANISM: Pseudomonas taetrolens

<400> SEQUENCE: 5

```
Ala Glu Ile Ala Thr Gly Ala Leu Asp Gln Ser Trp
1               5                   10
```

<210> SEQ ID NO 6
<211> LENGTH: 22
<212> TYPE: DNA
<213> ORGANISM: Artificial Sequence
<220> FEATURE:
<223> OTHER INFORMATION: Synthetic DNA

<400> SEQUENCE: 6
ttycaraayg tsgtsacscc sc                                          22

<210> SEQ ID NO 7
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = any nucleotide
<220> FEATURE:
<221> NAME/KEY: misc_feature
<222> LOCATION: (12)..(12)
<223> OTHER INFORMATION: n = any nucleotide
<220> FEATURE:
<221> NAME/KEY: misc_feature
<222> LOCATION: (18)..(18)
<223> OTHER INFORMATION: n = any nucleotide
<220> FEATURE:
<221> NAME/KEY: misc_feature
<222> LOCATION: (27)..(27)
<223> OTHER INFORMATION: n = any nucleotide

<400> SEQUENCE: 7
tgrtcratng cnccsgtngc ratytcngc                                   29

<210> SEQ ID NO 8
<211> LENGTH: 31

```
<212> TYPE: DNA
<213> ORGANISM: Artificial Sequence
<220> FEATURE:
<223> OTHER INFORMATION: Synthetic DNA

<400> SEQUENCE: 8
gccggatcca caagggttca gtcattcatg g                                      31

<210> SEQ ID NO 9
<211> LENGTH: 28
<212> TYPE: DNA
<213> ORGANISM: Artificial Sequence
<220> FEATURE:
<223> OTHER INFORMATION: Synthetic DNA

<400> SEQUENCE: 9
ccgaagcttt cagttcgcca ggccagcc                                          28

<210> SEQ ID NO 10
<211> LENGTH: 40
<212> TYPE: DNA
<213> ORGANISM: Artificial Sequence
<220> FEATURE:
<223> OTHER INFORMATION: Synthetic DNA

<400> SEQUENCE: 10
gtatcacgag gccctagctg tggtgtcatg gtcggtgatc                              40

<210> SEQ ID NO 11
<211> LENGTH: 40
<212> TYPE: DNA
<213> ORGANISM: Artificial Sequence
<220> FEATURE:
<223> OTHER INFORMATION: Synthetic DNA

<400> SEQUENCE: 11
ttcggggatt ccatatgata ccctttttac gtgaacttgc                              40

<210> SEQ ID NO 12
<211> LENGTH: 38
<212> TYPE: DNA
<213> ORGANISM: Artificial Sequence
<220> FEATURE:
<223> OTHER INFORMATION: Synthetic DNA

<400> SEQUENCE: 12
ggggggggca tatgcgacct ccttattacg tgaacttg                                38

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA

<400> SEQUENCE: 13
ggttcagtca catatggagg tcgctatgtc                                        30

<210> SEQ ID NO 14
<211> LENGTH: 33
<212> TYPE: DNA
<213> ORGANISM: Artificial Sequence
<220> FEATURE:
<223> OTHER INFORMATION: Synthetic DNA

<400> SEQUENCE: 14
atggaggtcc attagtcatt gcccggttca cgc                                    33
```

<210> SEQ ID NO 15
<211> LENGTH: 29
<212> TYPE: DNA
<213> ORGANISM: Artificial Sequence
<220> FEATURE:
<223> OTHER INFORMATION: Synthetic DNA

<400> SEQUENCE: 15
ccgggattcg ttaatccaaa cgttagctg                              29

<210> SEQ ID NO 16
<211> LENGTH: 30
<212> TYPE: DNA
<213> ORGANISM: Artificial Sequence
<220> FEATURE:
<223> OTHER INFORMATION: Synthetic DNA

<400> SEQUENCE: 16
ggcctgcagt taggcattaa ttgaaattgg                             30

<210> SEQ ID NO 17
<211> LENGTH: 1709
<212> TYPE: DNA
<213> ORGANISM: Bacillus macerans
<220> FEATURE:
<221> NAME/KEY: CDS
<222> LOCATION: (630)..(1481)
<223> OTHER INFORMATION:

<400> SEQUENCE: 17
tacatcaggt agcgccatgc atgacagaaa gggatcatga gcgttatctg ctgcgtttac    60
aacagagtga cgactgagtc agagcaattg tcgactttat cgcagaggtt tttatcagga   120
tcattatgcc atcagcttga gttgcaattc gaggatgcca tgtctggtca gacaacatta   180
aatccaggca ttgttagcta tgatgtcagt aaaggtggca gtttagtgat tagtatgcgc   240
tattctgtgt cctatccatt cgatgaaaaa ttacggaggc tcaacgttta gttgtaaaaa   300
gaggattttc attagatatt caagacgact ccaagcccca ttatgtcagt gaagatgatc   360
catttatcca acattagcg gctatttata gacgtcaatc aggagataca gaaacaccgt    420
tattatctac aggtggtgga acgtatgcac gtgtgctgaa aaaaggcgtg gcctttggca   480
tgctattccc tggggagcag gatgtggcgc atcggcgga tgagtttgta gtgattgaaa    540
atcttgtaaa agcagcggct atttatgcgg aagcaattgt tgagcttgcg ggaaaaaaat   600
aacataaaga cgaaaaggat gaacggaaa atg gca tat tca tta tgg aat gat    653
                                 Met Ala Tyr Ser Leu Trp Asn Asp
                                  1               5 caa att gtt gaa gaa gga tct att gca atc tca cca gaa gac aga ggt    701
Gln Ile Val Glu Glu Gly Ser Ile Ala Ile Ser Pro Glu Asp Arg Gly
        10                  15                  20 tat cag ttt ggt gac ggt att tat gaa gta att aaa gtt tat aac gga    749
Tyr Gln Phe Gly Asp Gly Ile Tyr Glu Val Ile Lys Val Tyr Asn Gly
 25                  30                  35                  40 aat atg ttt aca gca caa gag cac att gat cgt ttc tat gcg agc gcc    797
Asn Met Phe Thr Ala Gln Glu His Ile Asp Arg Phe Tyr Ala Ser Ala
                 45                  50                  55 gaa aaa att cgc ctt gtt atc cct tat aca aaa gat gtt tta cac aag    845
Glu Lys Ile Arg Leu Val Ile Pro Tyr Thr Lys Asp Val Leu His Lys
             60                  65                  70 tta cta cat gag cta att gaa aag aat aat cta gaa aca gga cat gtt    893
Leu Leu His Glu Leu Ile Glu Lys Asn Asn Leu Glu Thr Gly His Val
         75                  80                  85

```
tat ttt caa atc act cgt ggg gct aat tca cgt aat cac gtt ttc ccg      941
Tyr Phe Gln Ile Thr Arg Gly Ala Asn Ser Arg Asn His Val Phe Pro
        90                  95                 100 gat gca agt att cct gct gta tta act gga aat gta aaa gcg ggt gaa      989
Asp Ala Ser Ile Pro Ala Val Leu Thr Gly Asn Val Lys Ala Gly Glu
105                 110                 115                 120 cgt gca tat gaa aac ttt gaa aaa ggt gtt aaa gcc act ttt gtt gag     1037
Arg Ala Tyr Glu Asn Phe Glu Lys Gly Val Lys Ala Thr Phe Val Glu
                125                 130                 135 gat att cgt tgg ttg cgt tgt gac att aaa tct tta aac ttg ctt ggt     1085
Asp Ile Arg Trp Leu Arg Cys Asp Ile Lys Ser Leu Asn Leu Leu Gly
            140                 145                 150 gca gta tta gca aaa caa gaa gct gcg gag aaa ggt tgt tat gaa gcg     1133
Ala Val Leu Ala Lys Gln Glu Ala Ala Glu Lys Gly Cys Tyr Glu Ala
        155                 160                 165 atc tta cat cgc gga gat atc gtg aca gaa tgc tct tca gct aat gtt     1181
Ile Leu His Arg Gly Asp Ile Val Thr Glu Cys Ser Ser Ala Asn Val
170                 175                 180 tac gga att aaa gat gga aaa ctt tat aca cat cca gct aat aat ttc     1229
Tyr Gly Ile Lys Asp Gly Lys Leu Tyr Thr His Pro Ala Asn Asn Phe
185                 190                 195                 200 atc tta aat ggt att aca cgt caa gtc att tta aaa tgt gcg gaa gaa     1277
Ile Leu Asn Gly Ile Thr Arg Gln Val Ile Leu Lys Cys Ala Glu Glu
                205                 210                 215 att aat tta cca gta atc gaa gag cca atg acg aaa gct gat tta cta     1325
Ile Asn Leu Pro Val Ile Glu Glu Pro Met Thr Lys Ala Asp Leu Leu
            220                 225                 230 aca atg gat gaa atc att gtg tcg tct gta tct tct gag gtt acg cca     1373
Thr Met Asp Glu Ile Ile Val Ser Ser Val Ser Ser Glu Val Thr Pro
        235                 240                 245 gtc att gat gtg gac ggc aac caa att ggg gct gga gtt ccc ggt gaa     1421
Val Ile Asp Val Asp Gly Asn Gln Ile Gly Ala Gly Val Pro Gly Glu
250                 255                 260 tgg act cgt caa tta cag caa tca ttt gaa gcg aaa tta cca ctt tca     1469
Trp Thr Arg Gln Leu Gln Gln Ser Phe Glu Ala Lys Leu Pro Leu Ser
265                 270                 275                 280 atg aat acc aaa taaagaacc ttgtagagaa ctatctgtat ggatagttct          1521
Met Asn Thr Lys ctttatttat gggtgtaatg ttgggtctcg tcatgtaaaa taaaaggat agtagaataa    1581 tcttacagat tgaaatttgt agagcaatgt cgatgtaatg aatacataag aatgcataga  1641 ctcttttac aaagggatc gagaaaaaag agaactaaag agatggtaag taagaatgga    1701
gtgacctt                                                           1709

<210> SEQ ID NO 18
<211> LENGTH: 284
<212> TYPE: PRT
<213> ORGANISM: Bacillus macerans

<400> SEQUENCE: 18

Met Ala Tyr Ser Leu Trp Asn Asp Gln Ile Val Glu Glu Gly Ser Ile
1               5                   10                  15

Ala Ile Ser Pro Glu Asp Arg Gly Tyr Gln Phe Gly Asp Gly Ile Tyr
                20                  25                  30

Glu Val Ile Lys Val Tyr Asn Gly Asn Met Phe Thr Ala Gln Glu His
            35                  40                  45

Ile Asp Arg Phe Tyr Ala Ser Ala Glu Lys Ile Arg Leu Val Ile Pro
        50                  55                  60
```

```
Tyr Thr Lys Asp Val Leu His Lys Leu Leu His Glu Leu Ile Glu Lys
 65              70                  75                  80

Asn Asn Leu Glu Thr Gly His Val Tyr Phe Gln Ile Thr Arg Gly Ala
                 85                  90                  95

Asn Ser Arg Asn His Val Phe Pro Asp Ala Ser Ile Pro Ala Val Leu
            100                 105                 110

Thr Gly Asn Val Lys Ala Gly Glu Arg Ala Tyr Glu Asn Phe Glu Lys
            115                 120                 125

Gly Val Lys Ala Thr Phe Val Glu Asp Ile Arg Trp Leu Arg Cys Asp
            130             135                 140

Ile Lys Ser Leu Asn Leu Leu Gly Ala Val Leu Ala Lys Gln Glu Ala
145             150                 155                 160

Ala Glu Lys Gly Cys Tyr Glu Ala Ile Leu His Arg Gly Asp Ile Val
                165                 170                 175

Thr Glu Cys Ser Ser Ala Asn Val Tyr Gly Ile Lys Asp Gly Lys Leu
                180                 185                 190

Tyr Thr His Pro Ala Asn Asn Phe Ile Leu Asn Gly Ile Thr Arg Gln
            195                 200                 205

Val Ile Leu Lys Cys Ala Glu Glu Ile Asn Leu Pro Val Ile Glu Glu
210                 215                 220

Pro Met Thr Lys Ala Asp Leu Leu Thr Met Asp Glu Ile Ile Val Ser
225                 230                 235                 240

Ser Val Ser Ser Glu Val Thr Pro Val Ile Asp Val Asp Gly Asn Gln
                245                 250                 255

Ile Gly Ala Gly Val Pro Gly Glu Trp Thr Arg Gln Leu Gln Gln Ser
            260                 265                 270

Phe Glu Ala Lys Leu Pro Leu Ser Met Asn Thr Lys
            275                 280
```

PROCESS FOR PRODUCING GLUTAMATE DERIVATIVES

CROSS-REFERENCE TO RELATED APPLICATIONS

The present application is a continuation of U.S. Ser. No. 12/108,889, filed on Apr. 24, 2008 now abandoned, which is a divisional of U.S. Ser. No. 11/561,665, filed on Nov. 20, 2006, which is a divisional of U.S. Ser. No. 10/876,468 (now U.S. Pat. No. 7,297,800), filed on Jun. 28, 2004, which is a continuation of PCT/JP02/12852, filed on Dec. 9, 2002, which claims priority to JP 2002-245980, filed on Aug. 26, 2002, JP 2002-095760, filed on Mar. 29, 2002, and JP 2001-396471, filed on Dec. 27, 2001. The entire contents of these applications are incorporated herein by reference.

BACKGROUND OF THE INVENTION

1. Field of the Invention

The present invention relates to a process of producing glutamate derivatives using enzyme reactions. Further, the invention relates to a process of producing monatin using tryptophan as a starting material.

2. Discussion of the Background 4-(Indol-3-ylmethyl)-4-hydroxy-glutamic acid (3-(1-amino-1,3-dicarboxy-3-hydroxy-butan-4-yl)-indole) (hereinafter referred to as "monatin") represented by the following structural formula (6) is an amino acid contained in the root of a shrub tree (e.g., *Schlerochitom ilicifolius*) in South Africa. Monatin has a level of sweetness that is several hundreds-fold greater than that of sucrose. Therefore, monatin is a particularly promising low-calorie sweetener (see JP-A-64-25757).

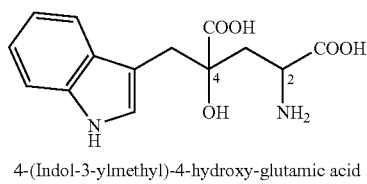

4-(Indol-3-ylmethyl)-4-hydroxy-glutamic acid (6)

Monatin has asymmetric carbons at positions 2 and 4. Naturally occurring monatin has a (2S,4S) steric configuration. In addition to the (2S,4S) steric configuration, the non-naturally occurring stereoisomers may be synthetically produced. It has been determined that all of the other stereoisomers of monatin have a highly enriched sweetness level compared to sucrose. Therefore, it is expected that any single monatin stereoisomer or mixture of monatin stereoisomers may be utilized as a sweetening agent or as a component for a sweetening agent (e.g., a sweetener).

Five examples of monatin production processes have been reported. The details of these processes are as described in the following references of the related art.

(1) Specification of U.S. Pat. No. 5,994,559
(2) Tetrahedron Letters, 2001, Vol. 42, No. 39, pp. 6793-6796
(3) Organic Letters, 2000, Vol. 2, No. 19, pp. 2967-2970
(4) Synthetic Communication, 1994, Vol. 24, No. 22, pp. 3197-3211
(5) Synthetic Communication, 1993, Vol. 23, No. 18, pp. 2511-2526

However, each of these processes requires multiple steps. Moreover, an industrial-scale production process is yet to be established. Thus, a demand exists for the development of a simple, high-yield industrial process for producing glutamate derivatives, including monatin and analogs thereof.

Thus, it is an object of the invention to provide an efficient process of producing glutamate derivatives and salt forms thereof including monatin. These compounds are promising as a component for a sweetener.

SUMMARY OF THE INVENTION

To achieve the aforementioned object, the present inventors have successfully developed a production method for a glutamate derivative (including salt forms thereof) of formula (2)

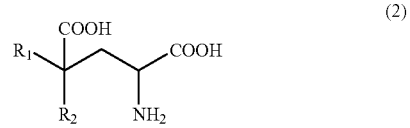
(2)

($R^1$ and $R^2$ in formula (2) have the same meanings as $R^1$ and $R^2$ in the general formula (1)). In this process, the glutamate derivative of the general formula (2) is produced from a substituted α-keto acid of formula (1) in the presence of a catalytic enzyme

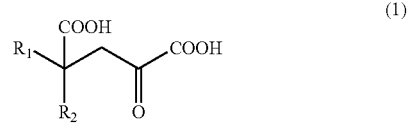
(1)

(in formula (1), $R^1$ and $R^2$ independently represent a substituent selected from the group consisting of a hydrogen atom, an alkyl group having one to 8 carbon atoms (C1 to C8), a C1 to C8 alkoxyl group, a C2 to C9 carboxyalkyl group, an aryl group having up to 20 carbon atoms, an aralkyl group having up to 20 carbon atoms, a heterocyclic ring-containing hydrocarbon group, and a hydroxyl group; when one of $R^1$ and $R^2$ represents a hydrogen atom, however, the other is not a hydrogen atom, a methyl group or an ethyl group; when one of $R^1$ and $R^2$ represents a hydroxyl group, the other is not a hydrogen atom or a methyl group; when $R^1$ contains an aromatic ring or a heterocyclic ring, the aromatic ring or the heterocyclic ring may be additionally substituted with a halogen atom, a hydroxyl group, alkyl groups with up to 3 carbon atoms, alkoxyl groups with up to 3 carbon atoms and an amino group), under conditions and for a time suitable to progress the reaction. Based on the finding, the invention has been achieved.

The process for producing glutamate derivatives in accordance with the present invention enables efficient production of monatin represented by formula (6) from 4-(indol-3-ylmethyl)-4-hydroxy-2-oxoglutaric acid (hereinafter referred to as "IHOG") represented by formula (7), using an enzymatic reaction.

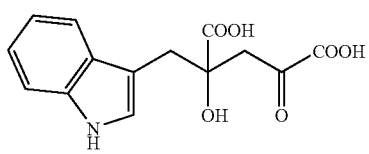

IHOG                                      (7)

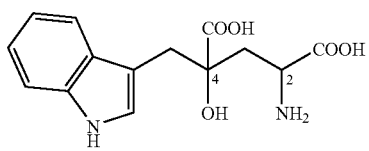

4-(Indol-3-ylmethyl)-4-hydroxy-glutamic acid    (6)

The present inventors have also developed new methods of producing monatin from tryptophan as a starting material, including the following reactions 1 to 3. The process of producing the glutamate derivatives of the present invention corresponds to reaction 3 in the monatin production process resulting from the following reactions 1 to 3. The production route of monatin, including reactions 1 to 3, is shown in reaction scheme (8).

Reaction 1: preparing indole-3-pyruvic acid from tryptophan in the presence of an enzyme catalyst.

Reaction 2: preparing the precursor keto acid (IHOG) via aldol condensation between indole-3-pyruvic acid and pyruvic acid (or oxaloacetic acid).

Reaction 3: synthetically preparing monatin by aminating IHOG at the position 2 in the presence of an enzyme catalyst.

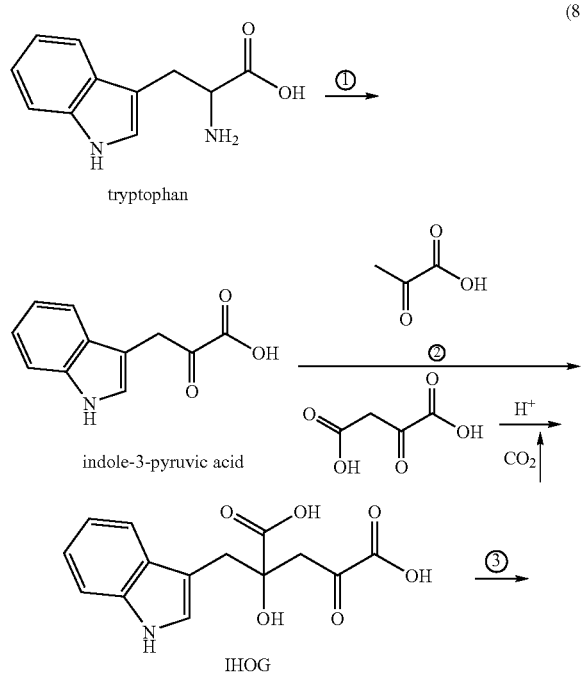

(8)

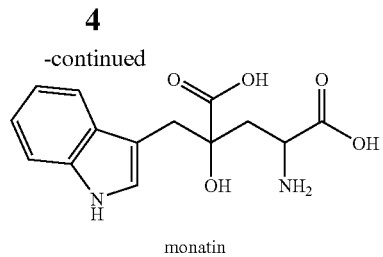

monatin

The present invention is described in more detail below.

[1] A process for producing a glutamate derivative, or salt forms thereof, of formula (2)

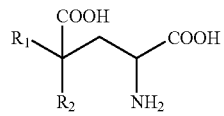

(2)

($R^1$ and $R^2$ in formula (2) have the same meanings as $R^1$ and $R^2$ in formula (1)). In this process, the glutamate derivative of the general formula (2) is produced from a substituted α-keto acid of formula (1) in the presence of a catalytic enzyme

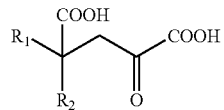

(1)

(in formula (1), $R^1$ and $R^2$ independently represent a substituent selected from the group consisting of a hydrogen atom, an alkyl group having one to 8 carbon atoms (C1 to C8), a C1 to C8 alkoxyl group, a C2 to C9 carboxyalkyl group, an aryl group having up to 20 carbon atoms, an aralkyl group having up to 20 carbon atoms, a heterocyclic ring-containing hydrocarbon group, and a hydroxyl group; when one of $R^1$ and $R^2$ represents a hydrogen atom, however, the other is not a hydrogen atom, a methyl group or an ethyl group; when one of $R^1$ and $R^2$ represents a hydroxyl group, the other is not a hydrogen atom or a methyl group; when $R^1$ contains an aromatic ring or a heterocyclic ring, the aromatic ring or the heterocyclic ring may be additionally substituted with a halogen atom, a hydroxyl group, alkyl groups with up to 3 carbon atoms, alkoxyl groups with up to 3 carbon atoms and amino group), under conditions and for a time suitable to progress the reaction.

[2] A process for producing a glutamate derivative as described in [1], wherein $R^1$ represents a phenylmethyl group or a 3-indolylmethyl group, and $R^2$ represents a hydroxyl group.

[3] A process for producing a glutamate derivative as described in [1] or [2], wherein the enzyme is a dehydrogenase or a transaminase.

[4] A process for producing a glutamate derivative as described in [3], wherein the enzyme is a transaminase and the reaction system therefor contains one or more types of amino acids as amino group donors.

[5] A process for producing a glutamate derivative as described in [4], wherein the amino acids are selected from the group consisting of glutamic acid, aspartic acid, alanine, tryptophan, phenylalanine, isoleucine, leucine, tyrosine, valine, arginine, asparagine, glutamine, methionine, ornithine, serine, cysteine, histidine and lysine.

[6] A process for producing a glutamate derivative as described in [3] through [5], wherein the enzyme is a L-amino acid transaminase.

[7] A process for producing a glutamate derivative as described in [3] through [5], wherein the enzyme is a D-amino acid transaminase.

[8] A process for producing a glutamate derivative as described in [7], wherein the reaction system therefor contains an enzyme that catalyzes the conversion of a L-amino acid to a D-amino acid.

[9] A process for producing a glutamate derivative as described in [6], wherein the L-amino acid transaminase is derived from a microorganism belonging to a genus selected from the group consisting of *Aeromonas*, *Agrobacterium*, *Alcaligenes*, *Beijerinckia*, *Escherichia*, *Proteus* and *Morganella*.

[10] A process for producing a glutamate derivative as described in [9], wherein the microorganism is selected from the group consisting of *Aeromonas hydrophila*, *Agrobacterium tumefaciens*, *Alcaligenes faecalis*, *Beijerinckia indica*, *Escherichia coli*, *Proteus rettgeri* and *Morganella morganii*.

[11] A process for producing a glutamate derivative as described in [7] or [8], wherein the D-amino acid transaminase is derived from a microorganism of the genus *Bacillus* or *Paenibacillus*.

[12] A process for producing a glutamate derivative as described in [11], wherein the microorganism is selected from the group consisting of *Bacillus sphaericus*, *Bacillus pulvifaciens*, *Bacillus macerans*, *Bacillus lentus*, *Paenibacillus larvae* subsp. *pulvifaciens* and *Paenibacillus macerans*.

[13] A process for producing a glutamate derivative as described in [1], wherein the enzyme is generated by a microorganism transformed with a gene encoding a D-amino acid transaminase.

[14] A process for producing a glutamate derivative as described in [13], wherein the microorganism is *Escherichia coli*.

[15] A process for producing a glutamate derivative as described in [13] or [14], wherein the gene encoding a D-amino acid transaminase is from *Bacillus sphaericus* or *Bacillus macerans*.

[16] A process for producing a glutamate derivative comprising:
    [I] producing a substituted α-keto acid of formula (4)

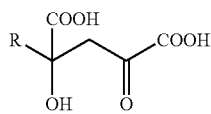

(4)

(R in formula (4) has the same meaning as R in formula (3)) in the presence of an enzyme catalyzing the production of substituted α-keto acid of formula (4) from a substituted α-keto acid represented by formula (3)

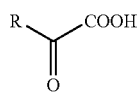

(3)

(in formula (3), R represents a substituent selected from the group consisting of a C2 to C8 alkyl group, a C1 to C8 alkoxyl group, a C2 to C9 carboxyalkyl group, an aryl group having up to 20 carbon atoms, an aralkyl group having up to 20 carbon atoms, a heterocyclic ring-containing hydrocarbon group, and a hydroxyl group; when R contains an aromatic ring or a heterocyclic ring, the aromatic ring or the heterocyclic ring may be additionally substituted with a halogen atom, a hydroxyl group, an alkyl group having up to 3 carbon atoms, an alkoxyl group having up to 3 carbon atoms and an amino group), and oxaloacetic acid or pyruvic acid, under conditions and for a time suitable to progress the reaction; and

[II] producing a glutamate derivative, or salt forms thereof, represented by formula (5) in the presence of an enzyme catalyzing the reaction production of glutamate derivative of formula (5)

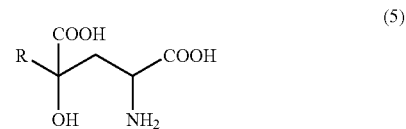

(5)

(R in formula (5) has the same meaning as R in formula (3)) from the substituted α-keto acid of formula (4), under conditions and for a time suitable to progress the reaction.

[17] A process for producing a glutamate derivative as described in [16], wherein R represents a phenylmethyl group or a 3-indolylmethyl group.

[18] A process for producing a glutamate derivative as described in [16] or [17], wherein the enzyme catalyzing the reaction in [I] is derived from a microorganism belonging to a genus selected from the group consisting of *Pseudomonas*, *Erwinia*, *Flavobacterium* and *Xanthomonas*.

[19] A process for producing a glutamate derivative as described in [18], wherein the microorganism is *Pseudomonas taetrolens*, *Pseudomonas coronafaciens*, *Pseudomonas desmolytica*, *Erwinia* sp., *Flavobacterium rhenanum* or *Xanthomonas citri*.

[20] A process for producing a glutamate derivative as described in [19], wherein the microorganism is *Pseudomonas taetrolens* ATCC4683 or *Pseudomonas coronafaciens* AJ2791.

[21] A process for producing a glutamate derivative as described in [16] or [17], wherein the enzyme catalyzing the reaction in [I] is any of the following proteins:
    (a) a protein comprising the amino acid sequence of SEQ ID NO.2;
    (b) a protein comprising an amino acid sequence prepared by substitution, deletion, insertion, addition and/or inversion of one or several amino acid residues in the amino acid sequence of SEQ ID NO.2 where the protein has aldolase activity;
    (c) a protein comprising the amino acid sequence of SEQ ID NO.3;
    (d) a protein comprising an amino acid sequence prepared by substitution, deletion, insertion, addition and/or inversion of one or several amino acid residues in the amino acid sequence of SEQ ID NO.3 where the protein has aldolase activity.

[22] A process for producing a glutamate derivative described in [16] or [17], wherein the enzyme catalyzing the reaction in [I] is an enzyme obtained from a recombinant where the gene encoding any of the following proteins is amplified and expressed:

(a) a protein comprising the amino acid sequence of SEQ ID NO.2;

(b) a protein comprising an amino acid sequence prepared by substitution, deletion, insertion, addition and/or inversion of one or several amino acid residues in the amino acid sequence of SEQ ID NO.2 having aldolase activity;

(c) a protein comprising the amino acid sequence of SEQ ID NO.3;

(d) a protein comprising an amino acid sequence prepared by substitution, deletion, insertion, addition and/or inversion of one or several amino acid residues in the amino acid sequence of SEQ ID NO.3 having the aldolase activity.

[23] A process for producing monatin comprising:

[A] producing indole-3-pyruvic acid in the presence of an enzyme catalyzing the conversion of tryptophan to indole-3-pyruvic acid;

[B] producing 4-(indol-3-ylmethyl)-4-hydroxy-2-oxoglutaric acid from indole-3-pyruvic acid, and oxaloacetic acid or pyruvic acid;

[C] producing monatin in the presence of an enzyme catalyzing the production of monatin from 4-(indol-3-ylmethyl)-4-hydroxy-2-oxoglutaric acid, by allowing 4-(indol-3-ylmethyl)-4-hydroxy-2-oxoglutaric acid.

[24] A process for producing monatin as described in [23], wherein [A] includes reacting tryptophan in the presence of an enzyme catalyzing the conversion of tryptophan to indole-3-pyruvic acid, and treating the resulting reaction solution with any of deaeration treatment, deoxygen treatment and pH adjustment up to pH 2 at maximum to collect indole-3-pyruvic acid.

[25] A process for producing monatin as described in [24], wherein the deaeration treatment or the deoxygen treatment is a process of substituting the whole or a part of the gas contained in the reaction solution with an inactive gas.

[26] A process for producing monatin as described in [25], wherein the inactive gas is selected from the group consisting of nitrogen, argon and helium.

[27] A process for producing monatin as described in [24] through [26], wherein the pH is adjusted by adding an acid to the reaction solution, and the process further comprises crystallizing indole-3-pyruvic acid produced as a consequence of the pH adjustment and collecting the resulting indole-3-pyruvic acid.

[28] A process for producing monatin as described in [27], wherein the acid is any of sulfuric acid, hydrochloric acid, nitric acid and phosphoric acid.

[29] A process of producing monatin as described in [23] through [28], wherein the enzyme catalyzing the reaction at [A] is derived from a microorganism having amino acid oxidase activity and catalase activity.

[30] A process of producing monatin as described in [23] through [29], wherein the enzyme catalyzing the reaction at [A] is a microorganism belonging to a genus selected from the group consisting of *Achromobacter*, *Proteus* and *Morganella*.

[31] A process for producing monatin as described in [30], wherein the enzyme is from a microorganism selected from the group consisting of *Achromobacter* sp. AJ2425, *Proteus rettgeri* IFO13501 and *Morganella morganii* IFO3168.

[32] A process for producing monatin as described in [23], wherein [A] comprises interacting a culture of a microorganism with tryptophan, wherein said microorganism possesses an ability to convert tryptophan to indole-3-pyruvic acid and is a member of a genus selected from the group consisting of *Achromobacter*, *Proteus*, *Morganella*, *Pseudomonas* and *Neurospora*, and further comprises producing indole-3-pyruvic acid and then collecting indole-3-pyruvic acid.

[33] A process of producing monatin as described in [23] through [32], wherein [B] is performed in the presence of an enzyme catalyst.

[34] A process of producing monatin as described in [23] through [32], wherein [B] is a chemical synthetic method.

The above objects highlight certain aspects of the invention. Additional objects, aspects and embodiments of the invention are found in the following detailed description of the invention.

DETAILED DESCRIPTION OF THE INVENTION

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein may be used in the practice or testing of the present invention, with suitable methods and materials being described herein. Further, the materials, methods, and examples are illustrative only and are not intended to be limiting, unless otherwise specified.

The process of producing glutamate derivatives developed by the inventors is for producing glutamate derivatives of formula (2) from a substituted α-keto acid of formula (1). More particularly, the process of the present invention relates to the production of glutamate derivatives in which an enzyme-catalyzed transamination is performed using an isolated enzyme or a microorganism generating the enzyme.

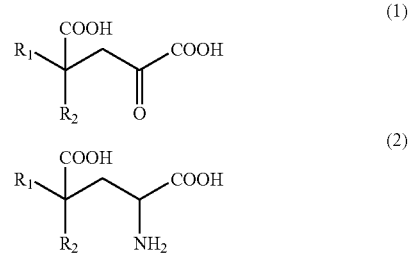

Additionally, the process for producing monatin from a starting material tryptophan developed by the inventors includes the following reactions 1 to 3. It should be noted that the process of producing monatin including the following reactions 1 to 3 utilizes the process of producing glutamate derivatives in accordance with the invention as reaction 3.

Reaction 1: synthesis of indole-3-pyruvic acid from tryptophan in the presence of an enzyme catalyst.

Reaction 2: synthesis of the precursor keto acid (IHOG) by aldol condensation between indole-3-pyruvic acid and pyruvic acid (or oxaloacetic acid).

Reaction 3: synthesis of monatin by aminating IHOG at the position 2 in the presence of an enzyme catalyst.

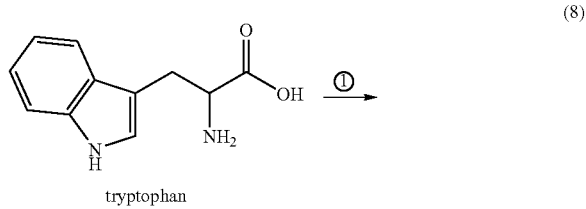

-continued

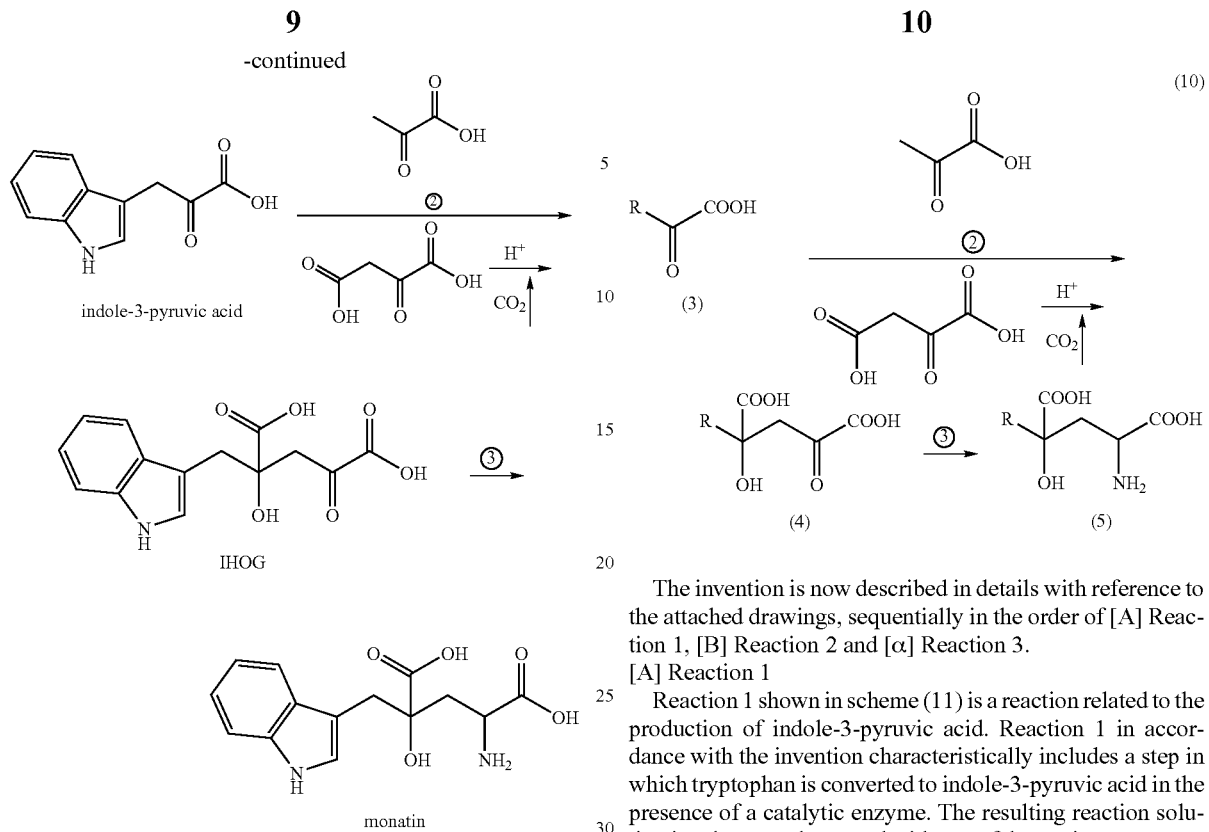

IHOG monatin

Among the reactions 1 to 3, the reactions 1 and 3 are enzymatic reactions. However, the reaction 2 may be carried out by either chemical synthesis or enzymatic synthesis, with no specific limitation.

The process for producing monatin in accordance with the invention is not limited to the process of producing monatin using tryptophan as the starting material but preferably includes the reaction 3 as an essential step among the reactions 1 to 3. In the other words, the invention also includes a process for producing monatin using commercially available indole-3-pyruvic acid as the starting material via the reactions 2 and 3, and a process of producing monatin from the precursor keto acid (IHOG) as the starting material for reaction 3. Thus, the process of producing monatin in accordance with the invention includes all of the following processes (a) through (c).

(a) Reactions 1+2+3

(b) Reactions 2+3

(c) Reaction 3 alone

Also in the present invention reaction 2 may be used for the production of the substituted α-keto acid that may be used as the substrate in the process of producing glutamate derivatives in accordance with the invention in addition to being used for the synthesis of the precursor keto acid (IHOG) of monatin.

As shown in scheme (10), the process of producing a glutamate derivative of formula (5) via reaction 3, using the substituted α-keto acid of formula (4) as obtained via reaction 2 (Reaction 2+Reaction 3), is also included in the process of producing glutamate derivatives in accordance with the invention.

The invention is now described in details with reference to the attached drawings, sequentially in the order of [A] Reaction 1, [B] Reaction 2 and [α] Reaction 3.

[A] Reaction 1

Reaction 1 shown in scheme (11) is a reaction related to the production of indole-3-pyruvic acid. Reaction 1 in accordance with the invention characteristically includes a step in which tryptophan is converted to indole-3-pyruvic acid in the presence of a catalytic enzyme. The resulting reaction solution is subsequently treated with any of deaeration treatment, deoxygen treatment or pH adjustment up to no more than pH 2 to collect indole-3-pyruvic acid.

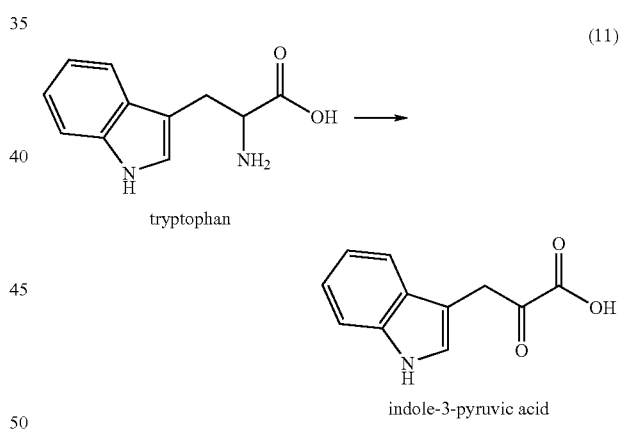

In the related art, a chemical process of producing indole-3-pyruvic acid was proposed by Giovanna De Luca, et al. and has been disclosed. This process includes a step of reacting tryptophan with pyridine aldehyde in the presence of a base for dehydrating proton acceptors to obtain indole-3-pyruvic acid at a yield of 50 to 62% (see the publication of Patent Publication (TOKUHYO) No. Sho 62-501912, the pamphlet of International Publication WO 87/00169). According to the process of DeLuca et al, the base and pyridine aldehyde are essential, but are very expensive and the resulting the yield is low. Therefore, the production cost is very high, which is problematic.

Additionally, a process for producing indole-3-pyruvic acid at a recovery of 64% was proposed by Politi Vincenzo, et al. The Vincenzo process uses a condensation reaction between indole and ethyl-3-bromopyruvate ester oxime followed by acid hydrolysis (EP 421 946). According to this process, a purification step using silica gel is needed and the resulting yield is low. Moreover, the raw materials are expensive. Thus, the process is disadvantageous in terms of its high cost for application to industrial production.

An enzymatic process for producing indole-3-pyruvic acid using a transaminase is also known (see scheme (12) below).

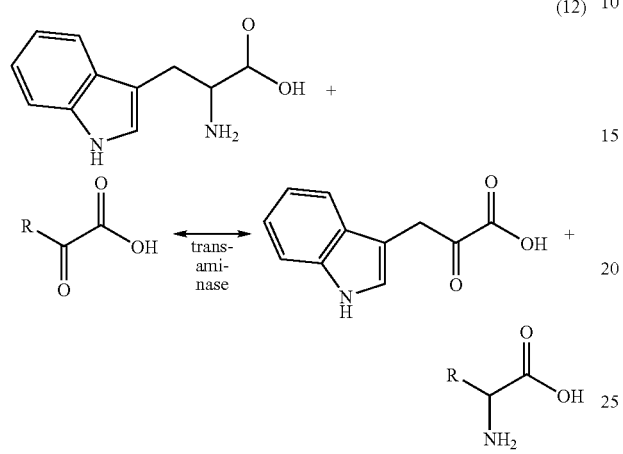

Moreover, reports exist of a process of producing indole-3-pyruvic acid by reacting L-tryptophan (L-Trp) with L-tryptophan transaminase from *Candida maltose* to generate indole-3-pyruvic acid from 40 mM L-Trp and 80 mM 2-ketoglutaric acid. The product is then purified with an ion exchange resin and the resulting indole-3-pyruvic acid is obtained at a yield of 72% (see East Germany Patent DD 297190 to Bobe Ruediger, et al.).

Another process for producing indole-3-pyruvic acid has been proffered in which L-Trp and 2-ketoglutaric acid react with an aspartate transaminase to generate indole-3-pyruvic acid. Subsequently the reaction solution is extracted in petroleum ether, and indole-3-pyruvic acid is purified by column chromatographic separation to collect the purified indole-3-pyruvic acid (see JP-A-59-95894 to Mario Matterazzi, et al.).

However, these processes using transaminase provide a low yield and require keto acid such as 2-ketoglutaric acid to serve as an amino group acceptor in addition to L-Trp. In addition, these processes involve the secondary production of an amino acid corresponding to the amino group acceptor at a molar amount equivalent to the molar amount of the produced indole-3-pyruvic acid. Further, more keto acid is required than L-Trp in the reaction system to improve the overall yield. As such, residual keto acid still remains even after the completion of reaction. Based on these factors, the collection of intended indole-3-pyruvic acid from the reaction solution requires a purification step using ion exchange resins or the like, which involve complicated procedures and high cost.

As a process for producing indole-3-pyruvic acid from L-Trp, further, a process using L-amino acid oxidase has also been known. Because indole-3-pyruvic acid is decomposed to indoleacetic acid (see scheme (14)) with hydrogen peroxide secondarily produced during the tryptophan oxidation by L-amino acid oxidase (see scheme (13)), herein, a process is proposed, including adding catalase to the reaction system to decompose the hydrogen peroxide (see scheme 15) (see the specification of U.S. Pat. No. 5,002,963; Tetrahedron Letters, 1987, Vol. 28, No. 12, pp. 1277-1280).

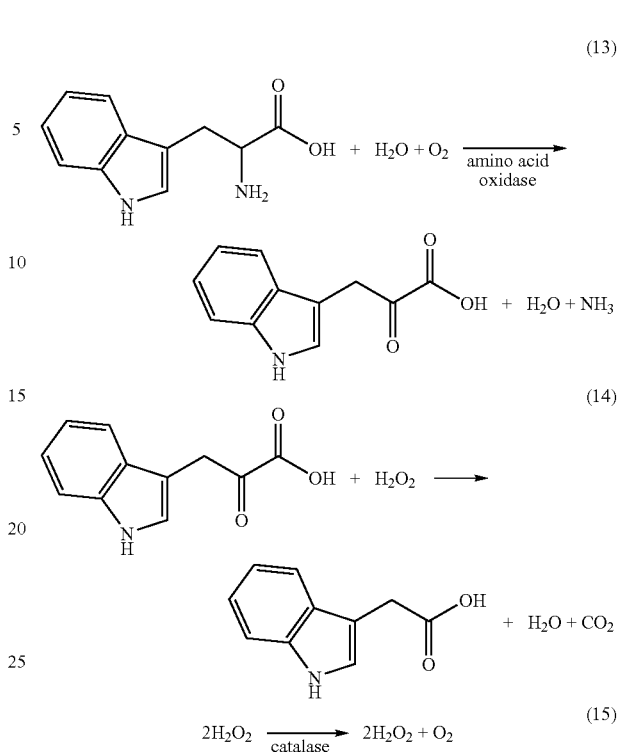

Specifically, the process entails employing an enzyme-immobilized column prepared by immobilizing L-amino acid oxidase from snake venom- and bovine liver-derived catalase on a carrier (e.g., a resin). The solution containing L-Trp is then passed through the column to permit the reaction, the indole-3-pyruvic acid produced on an ion exchange column is subsequently absorbed, the product is then eluted with methanol and dried to collect the product. According to the process, however, 0.5 g of the starting L-Trp results in only 0.2 g of indole-3-pyruvic acid, at a yield as low as 40%. The enzyme immobilization procedure and the purification procedure using ion exchange resin are laborious and require a step for recovering and recycling the residual L-Trp. Thus, the process is disadvantageously very costly.

Concerning L-amino acid oxidase derived from microorganisms, alternatively, John A. Duerre, et al. detect the oxidation activity of L-Trp by measuring the activity, including a step of approximately purifying the L-amino acid oxidase (deaminase) from *Proteus rettgeri* and a step of detecting oxygen consumption (see Journal of Bacteriology, 1975, Vol. 121, No. 2, pp. 656-663). Additionally, Furuyama, et al. confirm that the L-phenylalanine oxidase derived from *Pseudomonas* sp. P-501 interacts with L-Trp by measuring the oxidase activity, including a step of detecting oxygen consumption (see Noda Institute for Scientific Research, Kiyofumi Maruyama, Journal of Biochemistry, 1990, 108, pp. 327-333).

In these reports, however, oxidase activity is detected by means of measuring the L-tryptophan consumption, oxygen consumption and the amount of hydrogen peroxide generated during the enzyme reactions, but indole-3-pyruvic acid is never directly assayed. This may be due to the fact that indole-3-pyruvic acid is decomposed to indoleacetic acid by hydrogen peroxide produced via the reaction with amino acid oxidase. Meanwhile, no example of indole-3-pyruvic acid production using a microbial cell or a treated product from microbial cells exists to date. Therefore, it has been unknown how microorganisms decompose tryptophan or what decomposition products are produced thereby.

Additionally, the process described above using transaminase and the process using snake venom-derived L-amino acid oxidase for the production of indole-3-pyruvic acid are at low reaction yields and require chromatographic separation steps for the recovery of indole-3-pyruvic acid, due to the presence of by-product keto acid and residual L-tryptophan in the reaction solution. Thus, the processes require very laborious procedures and involve high production costs.

Accordingly, the present inventors have investigated how to provide a process of producing indole-3-pyruvic acid in a simple manner and at low cost. The inventors have discovered that the interaction of a microorganism having amino acid oxidase and catalase activities with tryptophan may produce indole-3-pyruvic acid. The resulting indole-3-pyruvic acid may then be collected. Particularly, the present inventors have found that the interaction of the aforementioned microorganism with tryptophan may produce indole-3-pyruvic acid, preferably with suppression of the decomposition of the intended product by inactive gas substitution or pH adjustment for the resulting reaction solution, which may be collected.

In addition to the decomposition of indole-3-pyruvic acid to indoleacetic acid with hydrogen peroxide, the inventors have discovered that indole-3-pyruvic acid is attacked with oxygen and the like in the solution resulting in decomposition products with unknown structures. Accordingly, the solution containing indole-3-pyruvic acid eventually becomes colored. Therefore, the present invention provides a method for solving the problem.

In accordance with the invention, tryptophan is reacted in the presence of an enzyme catalyzing the conversion of tryptophan to indole-3-pyruvic acid and the resulting solution is treated with any of the following methods to facilitate collection of indole-3-pyruvic acid: deaeration treatment, deoxygen treatment, or pH adjustment up to pH 2 at maximum.

The decomposition or coloring of indole-3-pyruvic acid may progress at its solution state. By the acid addition process, however, indole-3-pyruvic acid crystallizes during the early stage of the step of collecting the resulting indole-3-pyruvic acid. Therefore, compared with other purification and treatment steps, the acid addition process may advantageously suppress the decomposition and coloring.

Indoleacetic acid as a decomposition product of indole-3-pyruvic acid is not always readily removed under acidic conditions by direct crystallization. However, the secondary production of indoleacetic acid may be effectively suppressed via inactive gas substitution. A combination of crystallization under acidic conditions and inactive gas substitution may be more highly effective for the high-purity collection of indole-3-pyruvic acid.

Additionally, an alternate mode for performing reaction 1 in accordance with the present invention includes interacting a culture of a microorganism with tryptophan, wherein said microorganism possesses an ability to catalyze the conversion of tryptophan to indole-3-pyruvic acid, to produce and collect indole-3-pyruvic acid.

Heretofore, no report has existed about the interaction of a culture of a microorganism with tryptophan, wherein said microorganism possesses an ability to catalyze the conversion of tryptophan to indole-3-pyruvic acid, to produce and collect indole-3-pyruvic acid. Thus, the process provides a novel and useful process for producing indole-3-pyruvic acid by an enzymatic method.

The mode for performing reaction 1 in accordance with the present invention is now sequentially described in reference to (A-1) the enzyme for use in reaction 1 and (A-2) reaction conditions for reaction 1.

(A-1) Enzyme for Use in Reaction 1

The enzyme for use in reaction 1 includes any enzyme having an ability to convert tryptophan to indole-3-pyruvic acid, with no specific limitation. As the enzyme for use in reaction 1, enzymes having amino acid oxidase activity, and enzymes having catalase activity are preferable.

The "amino acid oxidase activity" for reaction 1 means an activity catalyzing the reaction shown in scheme (13). Generally, L-amino acid oxidase generates keto acid from the corresponding L-amino acid, while D-amino acid oxidase generates keto acid from the corresponding D-amino acid. Specifically, in accordance with the present invention, individually, a microorganism having L-amino acid oxidase activity may be used when L-tryptophan is used as the raw material, while a microorganism having D-amino acid oxidase activity may used when D-tryptophan is used as the raw material. Additionally, the preparation from DL-tryptophan is also applicable. When D- and L-amino acid oxidase is allowed to interact with DL-tryptophan, the intended indole-3-pyruvic acid may be quantitatively produced. When D- or L-amino acid oxidase interacts with DL-tryptophan, otherwise, the intended indole-3-pyruvic acid may be produced at a yield of 50%.

Additionally, the "catalase activity" means an activity catalyzing the reaction shown in scheme (15).

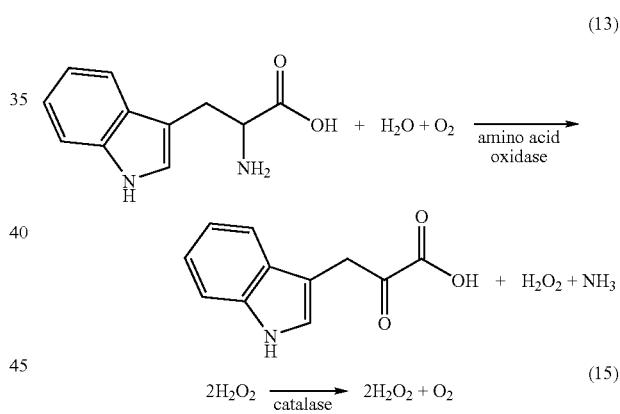

The enzyme with amino acid oxidase activity for reaction 1 may be selected by using any of various known methods, such as an assay detecting oxygen consumption due to the oxidation activity of amino acid (see for one example, Journal of Bacteriology, 1975, Vol. 121, No. 2, pp. 656-663) and a method of measuring hydrogen peroxide generated via the reaction (see for one example M. Gabler, et al., Enzyme and Microbial Technology, 2000, 27, pp. 605-611) as well as the method of direct measuring indole-3-pyruvic acid produced from tryptophan as described below in accordance with the present invention.

The enzyme having catalase activity for reaction 1 may be selected by using any of various known methods, including a method of measuring the hydrogen peroxide decrease via the catalase reaction based on the change of the absorbance at 230 nm to 250 nm, a method of measuring the residual hydrogen peroxide in the reaction solution with $KMnO_4$, and a method of measuring oxygen produced during the reaction with a manometer. As one example, a spectroscopic method of measuring the residual hydrogen peroxide is listed, which includes a step of oxidizing electron donors such as o-dianisidine via the peroxidase reaction, as described in M. Gabler, et al., Enzyme and Microbial Technology, 2000, 27, pp. 605-611. Using any of these methods, an enzyme having catalase activity may be selected.

Furthermore, the enzyme for use in reaction 1 may be selected by detecting the activity for producing indole-3-pyruvic acid from tryptophan, according to the method described below in Example 1.

The microorganism generating the enzyme for use in reaction 1 may be selected for example from a genus represented by *Achromobacter, Proteus, Morganella, Pseudomonas* and *Neurospora*. The microorganism is preferably a microorganism having amino acid oxidase activity and catalase activity. Specifically, the microorganism is, for example, selected from genus represented by *Achromobacter, Proteus,* and *Morganella*. Particularly, *Achromobacter* sp. AJ2425, *Proteus rettgeri* IFO13501 and *Morganella morganii* IFO3168 are preferable as such microorganisms.

Herein, *Achromobacter* sp. AJ2425 has been deposited as follows.

*Achromobacter* sp. Strain AJ2425

(a) Accession No. FERM BP-8244 (transferred from FERM P-18786 to the International Patent Organism Depositary, Nov. 22, 2002).
(b) Deposition date: Mar. 20, 2002
(c) Depositary Organization: International Patent Organism Depositary, The Institute of Advanced Industrial Science and Technology (No. 6, Chuo, 1-1-1, Higashi, Tsukuba, Ibaraki, Japan (zip code: 305-8566))

Additionally, microorganisms deposited at the Institute for Fermentation, Osaka (IFO) may be supplied and available from the Institute for Fermentation, (2-17-85, Tomimoto-cho, Yodogawa-ku, Osaka, Japan (zip code: 532-8686)).

These microorganisms may be microbial strains newly separated from the natural resources, such as in soil or from plants or may be microbial stains artificially grown by treatment with mutagenic chemicals or recombinant DNA technology.

The method for culturing the microorganism that produces the enzyme for use in reaction 1 may be performed using general culture media for use in the field, culture media containing carbon sources, nitrogen sources, inorganic salts, trace metal salts, vitamins and the like.

As the carbon sources, for example, any carbon source that is compatible with the microorganism may be used. Exemplary carbon sources include sugars such as glucose, sucrose and dextrin, alcohols such as sorbitol, ethanol and glycerol, organic acids such as fumaric acid, citric acid, acetic acid and propionic acid and salts thereof, hydrocarbons such as paraffin or mixtures thereof described above.

As the nitrogen sources, for example, ammonium sulfate, ammonium chloride, urea, yeast extract, meat extract, corn steep liquor and casein-hydrolyzed products or mixtures thereof may be used.

As a specific culture medium composition, for example, a culture medium containing 1.0% glucose, 0.3% ammonium sulfate, 1.0% powder yeast extract, 1.0% peptone, 0.1% $KH_2PO_4$, 0.3% $K_2HPO_4$, 0.05% $MgSO_4 \cdot 7H_2O$, 0.001% $FeSO_4 \cdot 7H_2O$, and 0.001% $MnSO_4 \cdot 4H_2O$ (pH 7.0) may be used.

Additionally, microbial cells having a high ability to convert tryptophan to indole-3-pyruvic acid may sometimes be obtained by adding L-amino acid or D-amino acid as an enzyme-inducing agent to the culture medium.

Detergents such as Triton X and Tween and organic solvents such as toluene and xylene may be used to enhance the permeability of microbial cells for incorporation of the substrate.

As to the culture temperature, generally, the reaction is performed within a range where a microorganism may grow. In view thereof, the temperature is generally in the range of about 20 to 45° C., preferably 25 to 37° C.

As to the pH of the culture medium, the pH is preferably adjusted to about 3 to 10, more preferably about 4 to 8.

As to the aeration condition, the condition should be set to a condition suitable for the growth of a microorganism to be used. Preferably, microorganism growth (and reaction) occurs under aerobic conditions.

As to the culture period, the reaction is generally conducted for about 12 to 120 hours, preferably about 16 to 96 hours.

(A-2) Reaction Conditions for Reaction 1

Reaction 1 includes producing indole-3-pyruvic acid from tryptophan in the presence of an enzyme catalyst and treating the resulting reaction solution with any one method selected from deaeration treatment, deoxygen treatment and pH adjustment up to pH 2 at maximum to collect indole-3-pyruvic acid.

In reaction 1, the term "in the presence of an enzyme" means allowing the enzyme to exist in the reaction system while the enzyme in an active state to enable the conversion of tryptophan to indole-3-pyruvic acid. In other words, the enzyme may exist in the reaction system as long as the enzyme is at any active state to enable converting tryptophan to indole-3-pyruvic acid. For example, the enzyme may be added solely to the reaction system (i.e., an isolated or purified enzyme), or a microorganism possessing the enzyme activity (e.g., microorganism generating the enzyme, cells transformed with recombinant DNA, etc.), a culture of the microorganism (e.g., liquid culture, solid culture, etc.), a culture medium (e.g. prepared by preliminarily eliminating microbial cells from the culture) or a treated product of the culture may be added to the reaction system. When a culture of a microorganism is used, reaction 1 may be progressed concurrently with culturing the microorganism. Otherwise, reaction 1 may be performed using a culture for obtaining the enzyme.

Herein, the "treatment" means a treatment for the purpose of recovering enzymes in microbial cells. The treatment includes, for example, treatments with ultrasonication, glass beads, French press, and freeze-drying and treatments with lytic enzymes, organic solvents, detergents or the like. Additionally, treated products after these treatments are further treated by routine methods (e.g., liquid chromatography, ammonium sulfate fractionation, etc.) to prepare a crude enzyme fraction or a purified enzyme, which may be used satisfactorily, when the fraction or the enzyme has an ability to be required.

When using the culture or the treated product thereof, the culture or the treated product may be included in carrageenan or polyacrylamide or may be immobilized on a film of polyether sulfone or regenerated cellulose, prior to use.

The microbial cell or a treated product of the microbial cell may be used at an amount (effective amount) sufficient to exert the intended effect in case of a given reaction. As to the effective amount, a person skilled in the art may readily determine the amount by a simple preliminary experiment. For rinsed wet microbial cells, for example, the amount preferably ranges 1 to 40 g per 100 ml of reaction solution.

As the substrate tryptophan, any of the L form, the D form and the DL form may be used. From the ready availability and price, the L form is preferred. Tryptophan is integrally, intermittently or continuously added within a concentration range without suppression of the intended reaction. As to the addition method, tryptophan may be directly added to the microbial cells during culturing. Otherwise, the microbial cells after the culture are once separated, with which tryptophan is mixed. Tryptophan may be mixed with a treated product thereof. For addition, the substrate is added as an aqueous solution or slurry. For the purpose of increasing the solubility or promoting the dispersion, organic solvents or detergents with no influence on the reaction may be mixed in tryptophan prior to or concurrent with addition.

The reaction for use in accordance with the invention is performed within a pH range of preferably about pH 3 to 10, more preferably about pH 5 to 9 and within a temperature range of preferably 10 to 60° C., more preferably about 20 to 40° C. for a reaction time of preferably about 0.5 to 120 hours, more preferably about 0.5 to 24 hours, while stirring or while the reaction mixture is left to stand alone. The substrate may be used at any concentration with no specific limitation, but may be preferably used at a concentration ranging from 0.1% to 10%.

As to the quantitative determination of tryptophan remaining in the liquid culture or in the reaction solution, the produced indole-3-pyruvic acid therein or the by-product indoleacetic acid therein, these may be readily measured immediately using well-known methods by high-performance liquid chromatography.

The liquid culture accumulating the indole-3-pyruvic acid (reaction solution) therein is treated by deaeration or deoxygen treatment to suppress decomposition of indole-3-pyruvic acid. As a method for deaeration treatment and deoxygen treatment, a process of substituting the gas (the whole or a part) contained in the reaction solution with inactive gases for example nitrogen and argon is listed.

Herein, the "deaeration treatment" means a procedure for eliminating components reactive with indole-3-pyruvic acid. These procedures include removing oxygen and hydrogen peroxide existing in the reaction solution or lowering the concentrations thereof, a process for substituting the reaction solution with inactive gases or a process for putting the reaction solution to conditions under reduced pressure (i.e, using aspirator and vacuum pump). Additionally, the "deoxygen treatment" means a procedure for eliminating the dissolved oxygen in the reaction solution or lowering the concentration thereof. Specifically, the method of eliminating oxygen in the solution includes for example a process of eliminating oxygen with inactive gas or a process of adding a deoxygen agent to the solution.

By substituting the reaction solution with inactive gas, the oxygen remaining in the reaction solution may be eliminated to terminate the reaction and additionally prevent the decomposition of the produced indole-3-pyruvic acid and the residual tryptophan. Herein, the "inactive gas" means a gas that does not directly or indirectly react with indole-3-pyruvic acid but effectively lowers the concentration and/or activity of the components reactive with indole-3-pyruvic acid and tryptophan, such as oxygen or a trace amount of residual hydrogen peroxide. Examples of the inactive gas suitable for use in accordance with the invention include nitrogen, argon and helium. The substitution with inactive gas may be performed immediately after the completion of the reaction. In case of the reaction using rinsed microbial cells, the substitution may be performed after the microbial cells are separated.

The method for charging inactive gas includes, for example, a process of substituting the gaseous phase with inactive gas to lower the oxygen concentration in the gaseous phase and a process of introducing inactive gas in the solution to eliminate the dissolved oxygen. The charging method is not particularly limited. In regard to the oxygen concentration in the gaseous phase, 5% or less, preferably 3% or less, more preferably 1% or less is adopted. Desirably, the oxygen concentration in the solution is 1 ppm or less, preferably 0.1 ppm or less, more preferably 0.01 ppm or less.

Further, the reaction may be terminated and the decomposition of indole-3-pyruvic acid may be suppressed by appropriately adding known substances such as sodium sulfite having been known to have an effect on the decrease of the dissolved oxygen concentration to the reaction solution.

As the deoxygen agent in accordance with the present invention, sulfite ions may be used. As the source for sulfite ion, there may be used salts such as sodium sulfite, potassium sulfite, ammonium sulfite and sulfurous acid or hydrosulfite. These are preferably used at a sulfite ion or hydrosulfite concentration of preferably 20 ppm or more to 1% or less, more preferably 100 ppm or more to 0.5% or less.

The inactive gas substitution treatment and the method for adding deoxygen agents to the solution may be performed in combination or either one thereof may be done.

The indole-3-pyruvic acid produced by the reaction is collected from the liquid culture or the reaction solution by general methods, prior to use. For the collection thereof from the liquid culture or the reaction solution, well-known procedures for general use in the field in such case, including filtration, centrifugation, vacuum concentration, ion exchange or adsorption chromatography or crystallization, may be used in appropriate combination, if necessary.

In one preferable embodiment of the invention, the pH of the reaction solution is lowered, to thereby crystallize or precipitate indole-3-pyruvic acid. The resulting crystals may be directly separated and collected from the mixture after the completion of the reaction. Concerning pH adjustment of the reaction solution, the pH is preferably adjusted to 2 or less, more preferably adjusted to 1 or less.

In accordance with the invention, indole-3-pyruvic acid may be produced at a high production yield while the concentrations of the by-product keto acid and residual L-tryptophan are reduced in the solution. By directly crystallizing indole-3-pyruvic acid under acidic conditions, therefore, the purification step may be simplified. In a more preferable embodiment of the invention, indole-3-pyruvic acid may be directly crystallized by appropriately adding acids such as sulfuric acid and hydrochloric acid to the reaction solution. In accordance with the process of the present invention, indole-3-pyruvic acid may be produced at a high production yield while the concentrations of the keto acid by-product and residual tryptophan are reduced in the solution. Thus, the purification procedure may be simplified by directly crystallizing indole-3-pyruvic acid under acidic conditions.

For the adjustment to acidic conditions, the acid type to be used is not specifically limited as long as the acid type serves to reduce the pH of the reaction solution to acidity. Examples of the acid to be used include for example hydrochloric acid, sulfuric acid, nitric acid and phosphoric acid. A person skilled in the art may appropriately select the crystallization temperature, the amount of the acid to be used, the crystallization period of time, and the method for adding the acid, within a range with no deterioration of the practice of the invention.

The crystallization temperature preferably ranges from −20° C. to 100° C., more preferably from 0° C. to 60° C. may. As the amount of the acid to be used, an amount thereof to adjust the reaction solution to preferably pH 2 or less, more preferably pH 1 or less may be selected. The acid may be added and used so that the hydrogen ion concentration in the solution after the acid addition is preferably about 0.01 to 10 mol/L, more preferably about 0.1 to 1 mol/L.

As the crystallization period of time, preferably about 1 to 100 hours, more preferably about 1 to 24 hours may be selected.

[B] Reaction 2

Reaction 2 in accordance with the invention is a reaction for synthesizing the precursor keto acid (IHOG) of monatin from indole-3-pyruvic acid and pyruvic acid (or oxaloacetic acid). However, reaction 2 may also be used not only for the IHOG synthesis but also for the synthesis of the substituted α-keto acid for use as the substrate in reaction 3 described below.

Specifically, reaction 2 may also be used widely as a reaction for producing the substituted α-keto acid represented by formula (4)

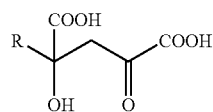

(4)

from the substituted α-keto acid represented by formula (3)

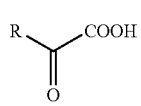

(3)

and oxaloacetic acid or pyruvic acid.

The substituted α-keto acid of formula (4) as obtained via reaction 2 may be used as the substrate for reaction 3 described below.

In formulae (3) and (4), R represents a substituent selected from the group consisting of an C2 to C8 alkyl group, a C1 to C8 alkoxyl group, a C2 to C9 carboxyalkyl group, an aryl group having up to 20 carbon atoms, an aralkyl group having up to 20 carbon atoms, a heterocyclic ring-containing hydrocarbon group, and a hydroxyl group. When R includes an aromatic ring or a heterocyclic ring, the aromatic ring or the heterocyclic ring may be further substituted with halogen atoms (iodine atom, bromine atom, chlorine atom, fluorine atom, etc.), a hydroxyl group, an alkyl group having up to 3 carbon atoms, an alkoxyl group having up to 3 carbon atoms and an amino group.

R is preferably a phenylmethyl group or a 3-indolylmethyl group, particularly preferably a 3-indolylmethyl group. Specifically, the substituted α-keto acid of the general formula (3) is preferably phenylpyruvic acid or indole-3-pyruvic acid, particularly preferably indole-3-pyruvic acid. As the indole-3-pyruvic acid, the indole-3-pyruvic acid prepared by the process described in item [A] of Reaction 1 is preferable. However, reasonably, the process of preparing indole-3-pyruvic acid is not limited to this process.

In case that indole-3-pyruvic acid is used as the substituted α-keto acid of the general formula (3), IHOG as the important intermediate for monatin production may be produced (reaction scheme (16)).

In case that phenylpyruvic acid is used as the substituted α-keto acid of the general formula (3), PHOG (4-phenylmethyl-4-hydroxy-2-oxoglutaric acid) as an intermediate keto acid for a monatin analog 4-phenylmethyl-4-hydroxyglutamic acid (PHG) may be produced (scheme (17)).

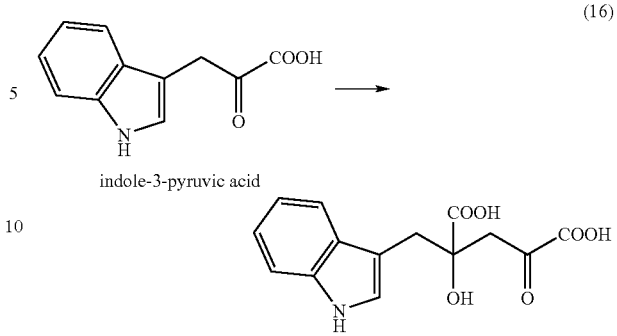

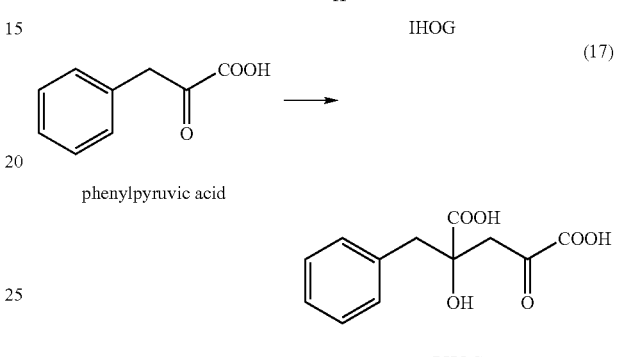

The mode for carrying out reaction 2 is not specifically limited. This reaction may be either a chemical reaction system or an enzymatic system. The mode for carrying out reaction 2 is divided into chemical reaction systems and enzymatic system, which are described in the following order:

[B-1] chemical reaction system;
[B-2] enzymatic reaction system;
[I] enzymes for use in reaction 2;
 (1) DNA encoding aldolase;
 (2) properties of aldolase;
 (3) Process of producing aldolase;
[II] reaction conditions for reaction 2.

(B-1) Chemical Reaction System

Reaction 2 using a chemical reaction system may be readily performed, using the method described below and the following Example 2, with no limitation to the method.

For example, the substituted α-keto acid represented by formula (4) may be produced by subjecting the substituted α-keto acid of formula (3) and oxaloacetic acid to a cross-aldol reaction and a decarboxylation reaction. The compound obtained by the aldol reaction is preliminarily formed in the reaction system, which is an important intermediate. Without isolation of the compound, the following decarboxylation step may be progressed.

The conditions for the aldol reaction are readily determined with no difficulty. The reaction may readily be progressed only when a substituted pyruvic acid and oxaloacetic acid are allowed to interact with each other in an appropriate solvent in the presence of an inorganic base or an organic base.

The type of the solvent to be used is not specifically limited, as long as the solvent is inactive to the reaction.

A person skilled in the art may appropriately select the reaction temperature, the amount of base to be used, the reaction period of time, and the method for adding starting materials, within a range with no deterioration of the practice of the invention.

The solvent preferably includes for example polar solvents such as water, methanol, acetonitrile, and dimethylformamide.

If used, the base preferably includes hydroxides or carbonates of inorganic bases (e.g., alkali metals or alkali earth metals, including lithium hydroxide, sodium hydroxide, potassium hydroxide, sodium carbonate, potassium carbonate and calcium carbonate), and organic bases (e.g., triethylamine).

The reaction temperature preferably ranges from −20 to 100° C., more preferably from 0 to 60° C.

For the reaction for decarboxylating the condensate from the aldol reaction, the reaction may be completed by spontaneous decarboxylation, but decarboxylation may be effectively performed by adding acid or metal ion (or both) to the reaction solution. The acid for use in that case includes, for example, hydrochloric acid, sulfuric acid, phosphoric acid, acetic acid, p-toluenesulfonic acid, and solid acids such as ion exchange resins, while the metal ion includes, for example, transition metal ions such as nickel ion, copper ion, and iron ion. The reaction temperature preferably ranges from −10 to 100° C., more preferably from 0 to 60° C.

(B-2) Enzymatic Reaction System
(I) Enzyme for Use in Reaction 2;

As the enzyme for use in reaction 2, any enzyme catalyzing the reaction for synthesizing the substituted α-keto acid represented by formula (4) via the aldol condensation between the substituted α-keto acid represented by formula (3) and oxaloacetic acid or pyruvic acid may be used, with no specific limitation. In other words, any enzyme derived from microorganisms or obtained by genetic recombination technology may be satisfactory as long as the enzyme catalyzes the reaction.

The investigations of the inventors have verified that microbial strains generating aldolase with the 4-phenylmethyl-4-hydroxy-2-oxoglutaric acid (PHOG)-decomposing activity exist in microorganisms belonging to the genera *Pseudomonas, Erwinia, Flavobacterium*, and *Xanthomonas*.

The aldolase generated by these microorganisms catalyzes the reaction for decomposing one PHOG molecule to generate one molecule of phenylpyruvic acid and one molecule of pyruvic acid. The inventors thought that the aldolase might possibly catalyze the reaction for synthesizing 4-(indol-3-ylmethyl)-4-hydroxy-2-oxoglutaric acid (IHOG) from indole-3-pyruvic acid and pyruvic acid (or oxaloacetic acid). Based on this concept, the inventors isolated and purified aldolase from cultured microbial cells of the microbial strains so as to identify the presence of a novel aldolase. Additionally, the inventors found that owing to the enzyme, IHOG was synthesized via the aldol condensation between indole-3-pyruvic acid and pyruvic acid (or oxaloacetic acid).

As microbial enzymes catalyzing the aldol condensation from two molecules of α-keto acid (and substituted α-keto acid) as the substrate, two examples were reported in the related art. These reports used 4-hydroxy-4-methyl-2-oxoglutarate aldolase from a bacterium of the genus *Pseudomonas* and 4-hydroxy-2-oxoglutarate aldolase in *E. coli, B. subtilis* or the like. A report discloses that the former 4-hydroxy-4-methyl-2-oxoglutarate aldolase catalyzes the reaction for generating 4-hydroxy-4-methyl-2-oxoglutarate (4-HMG) from two molecules of pyruvic acid and the reaction for generating one molecule of oxaloacetic acid and one molecule of pyruvic acid from 4-oxalocitramalate (see Kiyofumi Maruyama, Journal of Biochemistry, 1990, 108, pp. 327-333). Additionally, it is also known that the latter 4-hydroxy-2-oxoglutarate aldolase catalyses the reaction for generating 4-hydroxy-2-oxoglutarate (4HG) from one molecule of glyoxylic acid and one molecule of pyruvic acid.

However, heretofore, no report or no finding exists in regard to the 4-phenylmethyl-4-hydroxy-2-oxoglutaric acid (referred to as PHOG hereinafter)-decomposing activity or about the synthetic activity of the monatin precursor keto acid (IHOG) from indole-3-pyruvic acid and pyruvic acid (or oxaloacetic acid) in any of these microbial strains. It was totally unknown whether or not the aldolase generated by these microbial strains could be used for the synthetic route described above.

Prior to the findings of the inventors, in other words, no report exists regarding an example of synthetically preparing the precursor keto acid (IHOG) from indole-3-pyruvic acid and pyruvic acid (or oxaloacetic acid), using a microbial enzymatic system.

Additionally, the inventors purified the aldolase derived from *Pseudomonas taetrolens* ATCC4683 and determined the amino acid sequence of the aldolase. Further, the inventors successfully achieved the synthesis of a DNA molecule of about 30 bp as speculated from the amino acid sequence of the aldolase, the isolation and recovery of a part of the DNA encoding the aldolase by PCR, and the isolation of the full-length DNA encoding the aldolase derived from *Pseudomonas taetrolens* in the *Pseudomonas taetrolens* chromosomal gene libraries, using the resulting DNA fragment as probe.

SEQ ID No.1 in the sequence listing shows the DNA encoding the aldolase of the invention, as identified by the method described above. Additionally, SEQ ID Nos.2 and 3 show the amino acid sequences of the aldolase encoded by the nucleotide sequence SEQ ID No.1 in the sequence listing. SEQ ID No.2 in the sequence listing shows the amino acid sequence of the aldolase, which is encoded by the nucleotide sequence at the 456-th to the 1118-th position in the nucleotide sequence SEQ ID No.1 in the sequence listing. Additionally, SEQ ID No.3 in the sequence listing shows the amino acid sequence of the aldolase, which is encoded by the nucleotide sequence at the 444-th to the 1118-th position in the nucleotide sequence SEQ ID No. 1. Any aldolase described as SEQ ID Nos.2 and 3 has the aldolase activity and catalyzes the reaction for synthesizing 4-(indol-3-ylmethyl)-4-hydroxy-2-oxoglutaric acid (IHOG) from one molecule of indole-3-pyruvic acid and one molecule of pyruvic acid (or oxaloacetic acid).

(1) DNA Encoding Aldolase

As described above, the aldolase gene of the nucleotide sequence SEQ ID No.1 in the sequence listing was isolated from the chromosomal DNA of the *Pseudomonas taetrolens* strain ATCC4683. The nucleotide sequence SEQ ID No.1 in the sequence listing has 29% homology to the known 4-hydroxy-4-methyl-2-oxoglutarate aldolase (name of the gene: proA) derived from the bacterium *Pseudomonas ochraceae* (see Maruyama K., et al., Biosci. Biotechnol. Biochem., 2001, 65 (12), pp. 2701-2709) in terms of amino acid sequence. Herein, the homology is calculated, using a gene analysis software "genetyx ver. 6" while various parameters were employed as they were initially set in the software package.

The method for obtaining the DNA encoding aldolase from an aldolase-generating bacterium is now described.

First, the amino acid sequence of the purified aldolase is determined. Using the Edman method (Edman, P., Acta Chem. Scand., 1950, 4, p. 227), herein, the amino acid sequence may be determined. Alternatively, by using a sequencer manufactured by Applied Biosystems Inc., the amino acid sequence may also be determined. The aldolase derived from *Pseudomonas taetrolens* strain ATCC4683 of the invention was subjected to limited proteolysis with protease. The resulting peptide fragments were separated and recovered by reverse-phase HPLC. The internal amino acid sequences of two of those fragments were determined, to consequently identify the sequences SEQ ID Nos. 4 and 5.

Based on the amino acid sequences identified, the nucleotide sequence of DNA encoding the sequences may be deduced. For determining the nucleotide sequence of DNA the universal genetic code was used.

Based on the deduced nucleotide sequence, DNA molecules of about 30 base pairs were synthetically prepared. The method for synthetically preparing the DNA molecule is disclosed in Tetrahedron Letters, 1981, 22, p. 1859. Additionally, the DNA molecule may be synthetically prepared, using a synthesizer manufactured by Applied Biosystems Inc. The DNA molecule may be used as the probe for isolating the full-length DNA encoding the aldolase from the chromosomal gene libraries of the aldolase-generating microorganism. Otherwise, the DNA molecule may be used as the primer for amplifying the DNA encoding the aldolase of the invention by PCR. Because the DNA amplified by PCR does not include the full-length DNA encoding the aldolase, the DNA amplified by PCR is used to isolate the full-length DNA encoding the aldolase from the chromosomal gene libraries of the aldolase-generating microorganism.

The PCR procedure is described by White, T. J., et al., Trends Genet. 5, 1989, p. 185. The method for preparing chromosome DNA and the method for isolating an desired DNA molecule from a gene library using a DNA molecule as probe are described in Molecular Cloning, 2nd edition, Cold Spring Harbor press, 1989.

The method for determining the nucleotide sequence of the isolated DNA encoding the aldolase is described in A Practical Guide to Molecular Cloning, John Wiley & Sons, Inc., 1985. Further, the nucleotide sequence may also be determined, using a DNA sequencer manufactured by Applied Biosystems Inc. SEQ ID No.1 in the sequence listing shows the DNA encoding the aldolase derived from the *Pseudomonas taetrolens* strain ATCC4683.

It is to be understood that the DNA of SEQ ID No.1 is not the only DNA encoding an aldolase catalyzing the reaction for the synthesis of IHOG from indole-3-pyruvic acid and pyruvic acid (or oxaloacetic acid) for use in the present invention. Each species and each strain of the genus *Pseudomonas* generating the aldolase catalyzing the reaction for the synthesis of IHOG from indole-3-pyruvic acid and pyruvic acid (or oxaloacetic acid) should have difference in their nucleotide sequences, but nonetheless provide an aldolase that is embraced by the present invention.

Reasonably, even a DNA resulting from artificial mutation of the aldolase-encoding DNA isolated from the chromosome DNA of an aldolase-generating bacterium may also be used for reaction 2, in case that the artificial DNA encodes the aldolase. Site-specific mutation process described in Method in Enzymol., 1987, p. 154 is frequently used as a process of adding such artificial mutation.

Additionally, a DNA hybridizing with a DNA of a nucleotide sequence complementary to the nucleotide sequence SEQ ID No.1 in the sequence listing under stringent conditions and encoding a protein with the aldolase activity may also be used for reaction 2. Herein, the term "stringent conditions" means conditions for forming so-called specific hybrid but excludes the formation of non-specific hybrids. Although it is difficult to clearly show the conditions in numerical figure, one example thereof is as follows: under the conditions, DNAs with high homology of for example 50% or more, preferably 80% or more, more preferably 90% or more and particularly preferably 95% or more may hybridize to each other, but DNAs with lower homology cannot hybridize together. The term homology is preferably expressed as a value calculated while sequences for comparison are aligned so that the number of the same bases may be the largest. Otherwise, the conditions are conditions for enabling hybridization at a salt concentration corresponding to the general rinse condition for Southern hybridization, namely 0.1×SSC, 0.1%×SDS at 37° C., preferably 0.1×SSC, 0.1%×SDS at 60° C., more preferably 0.1×SSC, 0.1%×SDS at 65° C.

Further, the term "aldolase activity" means any activity for synthetically preparing IHOG from indole-3-pyruvic acid and pyruvic acid (or oxaloacetic acid). In case of a nucleotide sequence hybridizing with a nucleotide sequence complementary to the nucleotide sequence SEQ ID No.1 in the sequence listing under stringent conditions, the activity is at 10% or more, preferably 30% or more, more preferably 50% or more, still more preferably 70% or more of the aldolase activity of the protein of the amino acid sequence SEQ ID No.2 or 3 in the sequence listing under conditions at 33° C. and pH 9.

Further, DNA encoding essentially the same protein as the aldolase encoded by the DNA described as SEQ ID No.1 may also be used for reaction 2. In other words, the following DNAs are also included in the DNA of the invention.
(a) DNA encoding the protein of the amino acid sequence SEQ ID No.2 in the sequence listing.
(b) DNA encoding the protein of an amino acid sequence prepared after substitution, deletion, insertion, addition or inversion of one or several amino acid residues in the amino acid sequence SEQ ID No.2 in the sequence listing and with the aldolase activity.
(c) DNA encoding the protein of the amino acid sequence SEQ ID No.3 in the sequence listing.
(d) DNA encoding the protein of an amino acid sequence prepared after substitution, deletion, insertion, addition or inversion of one or several amino acid residues in the amino acid sequence SEQ ID No.3 in the sequence listing and with the aldolase activity.

Herein, the term "one or several" means a range of amino acid residues involving no severe deterioration of the steric configuration of the resulting protein or the aldolase activity, specifically including one to 50, preferably one to 30, more preferably one to 10. As described above, additionally, the term "aldolase activity" means the activity for the synthesis of IHOG from indole-3-pyruvic acid and pyruvic acid (or oxaloacetic acid). In case of an amino acid sequence prepared after substitution, deletion, insertion, addition or inversion of one or several amino acid residues in the amino acid sequence SEQ ID No.2 in the sequence listing, the resulting aldolase activity under conditions at 33° C. and pH 9 is at 10% or more, preferably 30% or more, more preferably 50% or more, still more preferably 70% or more of the aldolase activity of the protein of the amino acid sequence SEQ ID No.2 or 3 in the sequence listing, under conditions at 33° C. and pH 9.

(2) Aldolase Properties

Then, the properties of the aldolase purified from the *Pseudomonas taetrolens* strain ATCC4683 is now described.

The aldolase derived from the *Pseudomonas taetrolens* strain ATCC4683 has the amino acid sequence SEQ ID No.2 or 3 as clearly shown by the isolation and analysis of the gene described above. Reasonably, however, a protein of an amino acid sequence prepared after substitution, deletion, insertion, addition or inversion of one or several amino acid residues in the amino acid sequence SEQ ID No.2 or 3 in the sequence listing and with the aldolase activity may also be used for reaction 2.

In other words, the following proteins (a) to (d) may also be used as the enzyme catalyzing reaction 2.
- (a) Protein of an amino acid sequence SEQ ID No.2 in the sequence listing.
- (b) Protein of an amino acid sequence prepared after substitution, deletion, insertion, addition or inversion of one or several amino acid residues in the amino acid sequence SEQ ID No.2 in the sequence listing and with the aldolase activity.
- (c) Protein of the amino acid sequence SEQ ID No.3 in the sequence listing.
- (d) Protein of an amino acid sequence prepared after substitution, deletion, insertion, addition or inversion of one or several amino acid residues in the amino acid sequence SEQ ID No.3 in the sequence listing and with the aldolase activity.

Herein, the definitions of "several" and "aldolase activity" are the same as described in the description in the item DNA encoding aldolase (1).

Such aldolase may catalyze the reaction for synthetically preparing 4-(indol-3-ylmethyl)-4-hydroxy-2-oxoglutaric acid (IHOG) via the aldol condensation from indole-3-pyruvic acid and pyruvic acid (or oxaloacetic acid).

The aldolase activity of the aldolase may be assayed by measuring the amount of IHOG generated from indole-3-pyruvic acid and pyruvic acid (or oxaloacetic acid) by high performance liquid chromatography (HPLC).

Specifically, the aldolase activity may be estimated by adding aldolase to a reaction solution of 100 mM buffer, 50 mM indole-3-pyruvic acid, 250 mM pyruvic acid, 1 mM $MgCl_2$, and 1 v/v % toluene, for reaction under shaking at 33° C. for 4 hours and measuring the amount of IHOG generated by HPLC.

IHOG may be determined by HPLC using "Inertsil ODS-2" (5 µm, 4.6×250 mm) manufactured by GL Sciences, Inc. One example of the analytical conditions is shown below.

Mobile phase: 40 v/v % acetonitrile/5 mM phosphate dihydrogen tetrabutylammonium solution
Flow rate: 1 ml/min
Column temperature: 40° C.
Detection: UV 210 nm.

The enzymatic and chemical properties of the aldolase from *Pseudomonas taetrolens* as measured by the aforementioned analytical method, which is further described below.

The aldolase derived from *Pseudomonas taetrolens* may catalyze the reaction for synthetically preparing IHOG via the aldol condensation of indole-3-pyruvic acid and pyruvic acid (or oxaloacetic acid). As microbial enzymes catalyzing the aldol condensation from two molecules of α-keto acid (or substituted α-keto acid) as the substrate, so far, two such enzymes are reported, which are 4-hydroxy-4-methyl-2-oxoglutarate aldolase from genus *Pseudomonas* and 4-hydroxy-2-oxoglutarate aldolase existing in *E. coli* and *B. subtilis*. However, absolutely no finding or report exists about the former concerning the interaction thereof with PHOG or IHOG. Therefore, to date, it has been unknown whether or not PHOG (and IHOG) may be synthetically prepared, using the enzyme. Additionally, no PHOG-decomposing activity was observed in the latter, and therefore, the PHOG (and IHOG) synthesis using the enzyme was impossible. In other words, the aldolase derived from *Pseudomonas taetrolens* characteristically catalyzes the reaction for the synthesis of IHOG via the aldol condensation of indole-3-pyruvic acid and pyruvic acid (or oxaloacetic acid), unlike the aldolase reported so far.

The optimum pH of the aldolase derived from *Pseudomonas taetrolens* is around 9 at 33° C.

The molecular weight of the aldolase derived from *Pseudomonas taetrolens* as measured by gel filtration was about 146 kDa and was about 25 kDa measured by SDS-PAGE. Therefore, the aldolase of the invention will possibly form a homohexamer composed of a subunit with a molecular weight of about 25 kDa.

(3) Process of Preparing Aldolase

The process of preparing the aldolase is now described below. The process of preparing the aldolase for use in reaction 2 in accordance with the invention includes two processes, namely (i) a process of generating and accumulating the aldolase by microbiologically culturing an aldolase-generating bacterium and (ii) a process of generating and accumulating the aldolase by forming a transformant generating the aldolase by recombinant DNA technology and culturing the transformant.

(i) The Process of Generating and Accumulating the Aldolase by Microbial Culturing For the process of generating and accumulating the aldolase by microbiologically culturing an aldolase-generating bacterium, the microorganism as a source for recovering the aldolase includes for example microorganisms belong to the genera *Pseudomonas, Erwinia, Flavobacterium*, and *Xanthomonas*.

Among the genera *Pseudomonas, Erwinia, Flavobacterium*, and *Xanthomonas*, any microorganism generating aldolase catalyzing the reaction for the synthesis of the precursor keto acid (IHOG) from indole-3-pyruvic acid and pyruvic acid (or oxaloacetic acid) may be used in accordance with the invention. Preferably, the microorganism is selected from *Pseudomonas taetrolens* ATCC4683, *Pseudomonas coronafaciens* AJ2791, *Pseudomonas desmolytica* AJ1582, *Erwinia* sp. AJ2917, *Xanthomonas citri* AJ2797, and *Flavobacterium rhenanum* AJ2468. Particularly among them, *Pseudomonas taetrolens* ATCC4683 and *Pseudomonas coronafaciens* AJ2791 are preferable. The depositary organizations of these microorganisms are shown below.

(1) *Pseudomonas coronafaciens* strain AJ2791
- (a) Accession No. FERM BP-8246 (transferred from FERM P-18881 to the International Depositary, Nov. 22, 2002)
- (b) Deposition Date: Jun. 10, 2002
- (c) Depositary: International Patent Organism Depositary, The Institute of Advanced Industrial Science and Technology (No. 6, Chuo, 1-1-1, Higashi, Tsukuba, Ibaraki, Japan)

(2) *Pseudomonas desmolytica* AJ 1582
- (a) Accession No. FERM BP-8247 (transferred from FERM P-18882 to the International Depositary, Nov. 22, 2002)
- (b) Deposition Date: Jun. 10, 2002
- (c) Depositary: International Patent Organism Depositary, The Institute of Advanced Industrial Science and Technology (No. 6, Chuo, 1-1-1, Higashi, Tsukuba, Ibaraki, Japan)

(3) *Erwinia* sp. AJ2917
- (a) Accession No. FERM BP-8245 (transferred from FERM P-18880 to the International Depositary, Nov. 22, 2002)
- (b) Deposition Date: Jun. 10, 2002
- (c) Depositary: International Patent Organism Depositary, The Institute of Advanced Industrial Science and Technology (No. 6, Chuo, 1-1-1, Higashi, Tsukuba, Ibaraki, Japan)

(4) *Flavobacterium rhenanum* AJ2468
- (a) Accession No. FERM BP-1862
- (b) Deposition Date: Sep. 30, 1985

(c) Depositary: International Patent Organism Depositary, The Institute of Advanced Industrial Science and Technology (No. 6, Chuo, 1-1-1, Higashi, Tsukuba, Ibaraki, Japan)

(5) *Xanthomonas citri* AJ2797
  (a) Accession No. FERM BP-8250 (transferred from FERM P-4347 to the International Depositary, Nov. 27, 2002)
  (b) Deposition Date: Sep. 30, 1985
  (c) Depositary: International Patent Organism Depositary, The Institute of Advanced Industrial Science and Technology (No. 6, Chuo, 1-1-1, Higashi, Tsukuba, Ibaraki, Japan)

The mode for culturing the microorganism as a source for recovering the aldolase may be any of liquid culture and solid culture. An industrially advantageous mode is submerged aeration culture. As the nutrient source in nutritious culture media, those generally used for microbial culture, such as carbon sources, nitrogen sources, inorganic salts and other trace nutrient sources may be used. Any nutrient sources compatible with the microbial strains may be used.

For the aeration condition, aerobic conditions are adopted. The culture temperature may be within a range for microbial growth to generate the aldolase. Thus, no strict conditions exist therefor. Generally, the temperature is 10 to 50° C., preferably 30 to 40° C. The culture time period varies, depending on other culture conditions. For example, the culture time is up to a period involving the maximum aldolase generation, which is for example 5 hours to 7 days, preferably about 10 hours to about 3 days.

After the culture, the microbial cells are harvested by centrifugation (for example, 10,000×g, 10 minutes). Because aldolase mostly exists in microbial cells, the microbial cells are preferably disrupted or lysed, for aldolase solubilization. For the microbial disruption, treatments such as ultrasonic disruption, French press disruption, and glass bead disruption may be used. In case of lysis, additionally, a treatment with egg white lysozyme or peptidase or an appropriate combination of such treatments may be used.

For purifying the aldolase derived from the aldolase-generating bacterium, the enzyme-solubilized solution is used as a starting material for the purification. When undisrupted or non-lysed residue may be left, the solubilized solution is again treated by centrifugation procedures to remove the precipitating residue, which is rather advantageous for the purification.

For purifying the aldolase, any routine process generally used for enzyme purification may be used, including for example ammonium sulfate salting-out process, gel filtration chromatography, ion exchange chromatography, hydrophobic chromatography and hydroxyapatite chromatography. Consequently, aldolase-containing fractions with a higher activity may be obtained.

(ii) Process by Recombinant DNA Technology

The process of preparing the aldolase by recombinant DNA technology is now described. Numerous examples of preparing useful proteins such as enzymes and physiologically active substances using recombinant DNA technology are known in the art. Using recombinant DNA technology, useful proteins naturally occurring at trace amounts may be prepared at a mass scale.

Any DNA to be conjugated to a vector DNA may be satisfactory if the DNA may express the aldolase.

As an example of the aldolase gene conjugated to a vector DNA, herein, (1) the DNA described in the item "DNA encoding aldolase" may be used.

In case of mass protein preparation using recombinant DNA technology, preferably, the protein is associated together in a transformant to form a protein inclusion body. The advantages of the expression and preparation process are as follows. The intended protein may be protected from digestion with protease in microbial cells and the intended protein may be purified in a simple manner by centrifugation procedures following microbial cells disruption.

The protein inclusion body obtained in such manner is solubilized with a protein-denaturing agent and is treated by a procedure for regenerating the activity by removing the denaturing agent, and restoring the protein to a physiologically active (correctly folded) state. For example, there are many examples such as regeneration of human interleukin-2 activity (JP-A-61-257931).

So as to obtain the active type protein from such protein inclusion body, a series of procedures such as solubilization and activity regeneration are needed and are more complicated than those for directly generating the active type protein. In case of mass preparation of a protein with influences on the growth of a microbial cell in the microbial cell, the influences may be suppressed by accumulating the protein in the form of an inactive protein inclusion body in the microbial cell.

The process of mass preparation of an intended protein in the form of an inclusion body includes single expression of the intended protein under controls of a strong promoter, and a process of expressing the intended protein in the form of a fusion protein with a protein known to be expressed at a large scale.

After the expression thereof as a fusion protein, so as to remove the fusion protein and obtain the intended protein effectively, recognition sequences of restriction proteases should be arranged at appropriate sites.

In case of mass protein preparation using recombinant DNA technology, for example, microbial cells, actinomycetes cells, yeast cells, fungus cells, plant cells and animal cells may be used as host cells for transformation. The microbial cells for which host-vector systems are now developed include for example microorganism of genus *Escherichia*, microorganism of genus *Pseudomonas*, microorganism of genus *Corynebacterium*, and microorganism of *Bacillus*. Preferably, *Escherichia coli* is used because significant knowledge exists regarding how to use *Escherichia coli* for protein generation at a large scale. A process of preparing aldolase using transformed *Escherichia coli* is now described.

As the promoter for expressing the DNA encoding the aldolase, generally, promoters for *Escherichia coli* for exogenous protein preparation may be used and include for example strong promoters such as T7 promoter, trp promoter, lac promoter, tac promoter and PL promoter.

For generation of the aldolase in an inclusion body of the fusion protein, a gene encoding another protein, preferably a hydrophilic peptide is conjugated to the upstream or downstream of the aldolase gene, to prepare a fusion protein gene. The gene encoding such another protein may satisfactorily be any gene capable of increasing the accumulation of the fusion protein and raising the solubility of the fusion protein after denaturation and regeneration steps. For example, T7 gene 10, β-galactosidase gene, the gene of the dehydrofolate-reducing enzyme, interferon γ gene, interleukin-2 gene and prochymosin gene are candidates thereof.

For conjugation of genes encoding the "other" protein to the gene encoding the aldolase, the other genes should have the same reading frame for their codons. These genes are conjugated at appropriate restriction sites or are conjugated, using synthetic DNA of an appropriate sequence.

For increasing the generated amount, further, a terminator as a transcription termination sequence is preferably conjugated to the downstream of the fusion protein gene. The terminator includes for example T7 terminator, fd phage terminator, T4 terminator, the terminator for tetracycline resistant gene, and the terminator for *Escherichia coli* trpA gene.

The vector for introducing the gene encoding the aldolase or a gene encoding a fusion protein of the aldolase with another protein is preferably a multi-copy type plamid and includes for example a plasmid with an origin of replication as derived from Col E1, such as pUC-base plasmid, pBR322-base plasmid or derivatives thereof. Herein, the term "derivative" in the context of plasmids means such plasmids denatured by nucleotide substitution, deletion, insertion, addition or inversion. Herein, the term denaturation means mutagenic treatment with mutagens and UV irradiation or spontaneous mutation.

For transformant screening, further, the vector preferably has markers such as ampicillin resistant gene. As such plasmid, expression vectors with strong promoters are commercially available (pUC series (manufactured by TAKARA BIO INC.), pPROK series (manufactured by Clontech Laboratories, Inc.), pKK233-2 (manufactured by Clontech Laboratories, Inc.), etc.).

A DNA fragment, in which a promoter, the gene encoding the aldolase or a gene encoding a fusion protein of the aldolase with another protein and a terminator are sequentially conjugated together in this order, is conjugated to a vector DNA to form a recombinant DNA.

Using the recombinant DNA, *Escherichia coli* is transformed. The resulting *Escherichia coli* is cultured to express and generate the aldolase or the fusion protein of the aldolase with another protein. As the host to be transformed, strains generally used for the expression of exogenous gene may be used. Particularly, the *Escherichia coli* stains JM109 (DE3) and JM109 are preferable. The process for such transformation and the method for screening the resulting transformant are described in Molecular Cloning, 2-nd edition, Cold Spring Harbor press, 1989 and the like.

In case of the expression in the form of fusion protein, the aldolase may satisfactorily be excised using restriction proteases such as blood coagulation Factor Xa and kallikrein those recognizing sequences never existing in aldolase as the recognition sequences.

As the generation culture medium, culture media for general use in culturing *Escherichia coli*, such as M9-casamino acid culture medium and LB culture medium may be used. Additionally, the culture conditions and the conditions for inducing the generation are appropriately selected, depending on the types of the marker, promoter, and host bacterium for the vector used.

For recovering the aldolase or the fusion protein of the aldolase with another protein, the following processes are used.

When the aldolase or the fusion protein is solubilized in microbial cells, the microbial cells are once recovered, which are then disrupted or lysed for use as a crude enzyme solution. If necessary, further, the aldolase and the fusion protein thereof may be purified by general methods such as precipitation, filtration and column chromatography, prior to use. In this case, purification methods using antibodies against the aldolase or the fusion protein may also be used.

A protein inclusion body, when formed, is solubilized with a denaturing agent. The protein inclusion body may be solubilized together with the microbial cell protein. In terms of the following purification procedure, however, the inclusion body is preferably taken out and then solubilized. The inclusion body may be recovered from the microbial cells by known methods in the related art. For example, the microbial cells are disrupted to recover the inclusion body by centrifugation procedures. The denaturing agent for solubilizing the protein inclusion body includes for example guanidine hydrochloride (for example, 6M, pH 5 to 8) and urea (for example, 8 M).

By removing these denaturing agents by incremental dialysis and the like, the resulting protein may be regenerated as a protein with the activity. As the dialysis solution for use in the dialysis, Tris-HCl buffer and phosphate buffer may be used. The concentration includes for example 20 mM to 0.5 M at pH 5 to 8.

The protein concentration at the regeneration step is preferably suppressed to about 500 μg/ml or less. So as to suppress the self-crosslinking of the regenerated aldolase, the temperature for the dialysis is preferably 5° C. or less. The process of removing the denaturing agents includes dilution process and ultrafiltration process other than the dialysis process. Using any of these processes, the regeneration of the activity may be expected.

In case that the aldolase gene is derived from microorganism of the genus *Pseudomonas*, additionally, the aldolase may be expressed and generated in a host microorganism of genus *Pseudomonas* as a preferable embodiment. For example, Shi-En Lu, et al. reported a transformation and expression method in *Pseudomonas syringae* as the host cell (FEMS Microbiology Letters, 2002, 210, pp. 115-121). Additionally, Olsen, R. H., et al. reported about the transformation and expression method in *Pseudomonas aeruginosa* (Journal of Bacteriology, 1982, 150, pp. 60-69). Further, Grapner, S., et al. report about the transformation and expression method in *Pseudomonas stutzeri* (Biomol. Eng., 2000, 17, pp. 11-16). However, microorganisms of genus *Pseudomonas* as host cells for the expression of the aldolase are not limited to those recited herein.

Concerning the vector for introducing the aldolase gene into microorganism of genus *Pseudomonas*, a plasmid with an replication ori functioning inside cells of microorganism of the genus *Pseudomonas* may be used. For example, Eza Kalyaeva, et al. report the plasmid pKLH4.05 with the replicon TFK functioning in *Pseudomonas aeruginosa*. Additionally, so-called vectors for wide host ranges may also be used, which is used for transformation of Gram-negative microorganism. It is known that among these vectors, for example, RK404 (Ditta, G., et al., Plasmid, 1985, 13, pp. 149-153) and RSF1010 (Frey, J., et al., Gene, 1982, 24, pp. 289-296) function in *Pseudomonas* microorganism.

When the DNA of SEQ ID No.1 in the sequence listing is used as the DNA encoding the aldolase, the aldolase of the amino acid sequence SEQ ID No.2 or 3 is generated.

(II) Reaction Conditions for Reaction 2

The reaction conditions for reaction 2 when using an enzymatic system are described below.

As the enzyme catalyzing reaction 2, any enzyme catalyzing the reaction for synthesizing the substituted α-keto acid represented by formula (4) via the aldol condensation of the substituted α-keto acid represented by formula (3) and oxaloacetic acid or pyruvic acid may be used, with no specific limitation. In other words, any enzyme derived from microorganisms or obtained by genetic engineering technology may be satisfactory, as long as the enzyme catalyzes the reaction.

As such enzyme, the aldolase described in the item (I) Enzyme for use in reaction 2 is preferable. In this case, the aldolase obtained by culturing microbial cells generating the aldolase catalyzing reaction 2 from genera *Pseudomonas, Erwinia, Flavobacterium* and *Xanthomonas* may be used. Alternatively, the aldolase obtained by preparing a transformant generating aldolase catalyzing the reaction by recombinant DNA technology and then culturing the transformant may be used.

The term "in the presence of an enzyme" in reaction 2 means that an enzyme is allowed to exist in the reaction system, while the enzyme is at its state to enable catalyzing the reaction for synthetically preparing the substituted α-keto acid represented by formula (4) from the substituted α-keto acid represented by formula (3) and oxaloacetic acid or pyruvic acid. For example, the enzyme may singly be added to the reaction system or a microorganism with the activity of the enzyme (e.g., aldolase-generating microorganism, cells transformed by recombinant DNA, etc.), a culture of the microorganism (e.g., liquid culture, solid culture, etc.), a culture media (e.g., the culture from which microbial cells are removed), and treated products of the culture may be added to the reaction system.

When the culture of the microorganism is used, reaction 2 is progressed while the microorganism is simultaneously cultured. Otherwise, reaction 2 is performed using the culture prepared by preliminary culturing so as to obtain the enzyme. Additionally, the term "treatment" means treatment for the purpose of recovering the enzyme from microbial cells and includes for example treatments with ultrasonication, glass bead, French press, and freeze-drying and treatments with lysed enzymes, organic solvents, detergents or the like. Additionally, any crude fractionated enzyme or purified enzyme as prepared by further processing the treated product after these treatment by routine methods (e.g., liquid chromatography, ammonium sulfate fractionation, etc.) may be satisfactory, as long as the crude or purified enzyme has the ability required.

When the substituted α-keto acid of formula (4) is produced using the aldolase-generating bacterium or a cell transformed by recombinant DNA, the substrates may be added to the liquid culture during the culture. Otherwise, any of the microbial cells separated from the liquid culture and the rinsed microbial cells may be used. Additionally, the microbial cell-treated product prepared by disrupting or lysing the microbial cells may be used as it is or the aldolase recovered from the microbial cell-treated product is used as a crude enzyme solution, from which the enzyme is purified and used as well.

When using the culture or the treated product, further, the culture or the treated product may be included in carrageenan and polyacrylamide or may be immobilized on a film of polyether sulfone and regenerated cellulose for use.

For progressing reaction 2 in the presence of an enzyme, a reaction solution containing at least one of the substituted α-keto acid represented by formula (3), oxaloacetic acid or pyruvic acid and the enzyme catalyzing reaction 2 is adjusted to an appropriate temperature of 20 to 50° C., which is then left to stand alone or is shaken or agitated while the pH is kept at 6 to 12 for 30 minutes to 5 days.

The reaction velocity may be increased by adding divalent cations such as $Mg^{2+}$, $Mn^{2+}$, $Ni^{2+}$, and $Co^{2+}$ to the reaction solution. From the standpoint of cost, preferably, $Mg^{2+}$ may sometimes be used.

For adding these divalent cations to the reaction solution, any salt thereof may be used as long as the salt never inhibits the reaction. Preferably, $MgCl_2$, $MgSO_4$, $MnSO_4$ or the like may be used. A person skilled in the art may determine the concentration of these divalent cations to be added, by simple preliminary experiments. The divalent cations may be added within a range of 0.01 mM to 10 mM, preferably 0.1 mM to 5 mM, more preferably 0.5 mM to 2 mM.

One example of the reaction conditions preferable for performing reaction 2 is described below. To the reaction solution consisting of 100 mM buffer, 50 mM indole-3-pyruvic acid, 250 mM pyruvic acid, 1 mM $MgCl_2$, and 1 v/v % toluene, rinsed *E. coli* microbial cells expressing the aldolase are added as the enzyme source to 10 w/v %, for reaction under shaking at 33° C. for 4 hours, to obtain 4-(indol-3-ylmethyl)-4-hydroxy-2-oxoglutaric acid (IHOG).

The resulting substituted α-keto acid of formula (4) may be separated and purified by known methods. For example, the known methods include a method of contacting the substituted α-keto acid with an ion exchange resin to adsorb basic amino acids, and eluting and subsequently crystallizing the resulting substituted α-keto acid; and a method of eluting the substituted α-keto acid, decoloring and filtering the substituted α-keto acid with active charcoal and then crystallizing the substituted α-keto acid.

Via reaction 2, the precursor keto-acid (IHOG) useful as an intermediate for monatin synthesis may be generated from indole-3-pyruvic acid and pyruvic acid (or oxaloacetic acid).

[C] Reaction 3

The reaction 3 of the invention is a reaction related to monatin production and is preferably used for the synthesis of monatin from the precursor keto acid (IHOG). However, the reaction 3 may be used not only for the synthesis of monatin but also may be used widely for the reaction of producing glutamate derivatives of formula (2) from the substituted α-keto acid of formula (1).

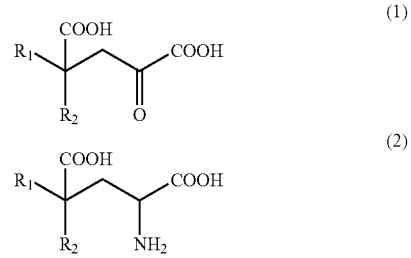

Herein, $R^1$ and $R^2$ independently represent a substituent selected from the group consisting of a hydrogen atom, a C1 to C8 alkyl group, a C1 to C8 alkoxyl group, a C2 to C9 carboxyalkyl group, an aryl group having up to 20 carbon atoms, an aralkyl group having up to 20 carbon atoms, a heterocyclic group-containing hydrocarbon group, and a hydroxyl group. When either of $R^1$ and $R^2$ represents a hydrogen atom, the other is not a hydrogen atom, a methyl group or an ethyl group. When either one of $R^1$ and $R^2$ represents a hydroxyl group, the other is not a hydrogen atom or a methyl group.

The aromatic ring or the heterocyclic ring contained in the substituent $R^1$ in the formula may contain at least one of halogen atoms, a hydroxyl group, alkyl groups with up to 3 carbon atoms, alkoxyl group with up to 3 carbon atoms, and an amino group.

Among the foregoing, preferably, $R^1$ is selected from the group consisting of a $C_2$ to $C_4$ alkyl group, a $C_2$ to $C_4$ carboxyalkyl group, a phenylmethyl group and a 3-indolylmethyl group (the benzene ring or the indole ring may additionally contain at least one of halogen atoms (iodine atom, bromine atom, chlorine atom, fluorine atom, etc.)), a hydroxyl group, an alkyl group having up to 3 carbon atoms, an alkoxyl group having up to 3 carbon atoms and an amino group) and $R^2$ is a hydroxyl group. More preferably, $R^1$ is a phenylmethyl group or a 3-indolylmethyl group and $R^2$ is a hydroxyl group.

In case that $R^1$ is a 3-indolylmethyl group and $R^2$ is a hydroxyl group, i.e. that IHOG (4-(indol-3-ylmethyl)-4-hydroxy-2-oxoglutaric acid) is used as the substituted α-keto acid of formula (1), monatin may be obtained as the glutamate derivative of formula (2).

In case that $R^1$ is a phenylmethyl group and $R^2$ is a hydroxyl group, i.e. that PHOG (4-phenylmethyl-4-hydroxy-2-oxoglutaric acid) is used as the substituted α-keto acid of ormula (1), a monatin analog 4-phenylmethyl-4-hydroxy-glutamic acid (PHG) may be obtained as the glutamate derivative of formula (2).

As the substituted α-keto acid represented by formula (1) as the substrate, the substituted α-keto acid of formula (4) as obtained by the process described in the item [B] of Reaction 2 is preferably used. More preferably, IHOG prepared by the process in the item [B] of Reaction 2, using indole-3-pyruvic acid prepared by the process described in the item [A] of Reaction 1 is used. However, reasonably, the process of preparing the substituted α-keto acid represented by formula (1) is not limited to these processes described above.

Reaction 3 utilizes the reaction of the enzyme catalyzing the reaction for generating an amino acid corresponding to the substituted α-keto acid as the substrate. Reaction 3 relates, for example, to a process of producing glutamate derivatives by reacting a protein catalyzing transamination or a microorganism generating the protein. Herein, the term "transamination" means a reaction for converting a precursor ketone compound to the corresponding amino compound by transferring the amino group of the donor substrate to the ketone group of the acceptor compound.

The mode for carrying out the reaction 3 of the invention is now described in detail in the following order.
(C-1) Enzyme for use in reaction 3
(C-2) Reaction conditions for reaction 3.
(C-1) Enzyme catalyzing the reaction for generating amino acid For reaction 3, the enzyme catalyzing the reaction for generating an amino acid corresponding to the substituted α-keto acid as the substrate individually includes for example a transaminase as an enzyme catalyzing transamination and additionally includes a dehydrogenase as the enzyme catalyzing the reductive amination of the keto acid. The transaminase for use in reaction 3 is satisfactorily an enzyme catalyzing the reaction for generating a glutamate derivative from a corresponding substituted α-keto acid and an amino donor as the starting materials. Via the action of such enzyme, the substituted α-keto acid represented by formula (1) may be converted to the corresponding glutamate derivative (represented by formula (2)).

As the amino donor, then, a compound containing an amino group is used. For example, the compound includes amino compounds such as L-amino acids and D-amino acids naturally occurring and non-naturally occurring. Specifically, the amino acids include for example glutamic acid, aspartic acid, alanine, tryptophan, phenylalanine, isoleucine, leucine, tyrosine, valine, arginine, asparagine, glutamine, methionine, ornithine, serine, cysteine, histidine and lysine. The amino donor to be added for the reaction may be a single one type or a mixture of plural types of such donors.

Generally, L-amino acid transaminase generates an intended L-amino acid by transferring the amino group of an L-amino acid donor to the precursor keto acid, while D-amino acid transaminase generates an intended D-amino acid by transferring the amino group of a D-amino acid donor to the precursor keto acid. Via the selection of such enzyme, an optical isomer of a glutamate derivative to be generated may also be selected. For example, the reaction with D-amino acid transaminase in the presence of D-amino acids such as D-alanine, D-glutamic acid, and D-aspartic acid may selectively generate D-glutamate derivatives from the precursor keto acid.

As described above, monatin as one of glutamate derivatives as the object of the invention includes three optical isomers in addition to the naturally occurring type (2S,4S). It has been confirmed that any of these isomers has a sweetness intensities several hundreds-fold to some thousands-fold that of sucrose. In one of the preferable embodiments of the present invention, the reaction of D-amino acid transaminase with the precursor keto acid for monatin may generate the 2R form of monatin stereo-selectively, while the reaction of L-amino acid transaminase with the precursor may generate the 2S form of monatin stereo-selectively. In one of more preferable embodiments, the use of D-amino acid transaminase may generate selectively the 2R form thereof as an isomer having higher sweetness level.

When it is intended to use D-amino acid as an amino donor, herein, the corresponding L-amino acid is added to the reaction solution, to allow the amino acid to exist concurrently with an enzyme catalyzing the racemization reaction of the amino acid, so that the donor may be supplied as a D-amino acid donor. As such racemization enzyme, preferable examples thereof include alanine racemase, glutamic acid racemase, aspartic acid racemase, and phenylalanine racemase. In this case, L-alanine, L-glutamic acid, L-phenylalanine, L-aspartic acid or racemic mixtures of these L-amino acids may be added to the reaction solution, while D-glutamate derivatives are under way of generation.

The enzyme catalyzing transamination may also be prepared by cultivating a microorganism generating such enzyme. Such microorganism includes for example microorganisms belonging to the genera *Aeromonas, Agrobacterium, Alcaligenes, Bacillus, Beijerinckia, Escherichia, Proteus, Morganella* and *Paenibacillus*.

Specifically, these microorganisms include for example those described below. In other words, the microorganism generating L-amino acid transaminase with an activity for generating glutamate derivatives described in formula (2) from the substituted α-keto acid described in formula (1) include the following examples.
*Aeromonas hydrophila* IFO3820
*Agrobacterium tumefaciens* IFO3058
*Alcaligenes faecalis* ATCC8750
*Beijerinckia indica* ATCC9037
*Escherichia coli* ATCC12814
*Proteus rettgeri* IFO13501
*Morganella morganii* IFO3848
Additionally, the microorganisms generating D-amino acid transaminase include the following examples.
*Bacillus sphaericus* ATCC 10208
*Bacillus pulvifaciens* AJ11327
*Paenibacillus larvae* subsp. *pulvifaciens* ATCC13537
*Bacillus macerans* AJ1617
*Paenibacillus macerans* ATCC8244
*Bacillus lentus* AJ12699
*Bacillus lentus* ATCC10840
Herein, *Bacillus macerans* AJ1617 has been deposited as follows. *Bacillus macerans* strain AJ1617
(a) Accession No. FERM BP-8243 (transferred from FERM P-18653 to the International Patent Organism Depositary, Nov. 22, 2002).

(b) Deposition date: Dec. 13, 2001

(c) Depositary Organization: International Patent Organism Depositary, The Institute of Advanced Industrial Science and Technology (No. 6, Chuo, 1-1-1, Higashi, Tsukuba, Ibaraki, Japan)

The microorganisms may satisfactorily be microbial strains newly separated from the natural resources, such as in soil and from plants or may satisfactorily be microbial strains artificially prepared by treatment with mutagenic chemicals and recombinant DNA technology.

In one of preferable embodiments of the present invention, an intended gene encoding an enzyme catalyzing the intended transamination from the substituted α-keto acid to glutamate derivatives may be integrated into microbial cells as well. Numerous examples for preparing useful proteins such as enzyme and physiologically active substances using recombinant DNA technology have been known. The use of recombinant DNA technology enables mass preparation of useful proteins from natural origins at a trace amount. The gene to be integrated includes L-amino acid transaminase genes and D-amino acid transaminase genes. One possible example is the introduction of D-amino acid transaminase genes from *Bacillus sphaericus* or *Bacillus macerans* into microorganisms.

European Patent Publication 0 736 604 and Taylor, et al., Journal of Bacteriol., 1998, Vol. 180, No. 16, p. 4319 report about the D-amino acid transaminase gene derived from *Bacillus sphaericus*.

As the D-amino acid transaminase gene derived from *Bacillus macerans*, additionally, the DNA of the D-amino acid transaminase gene derived from *Bacillus macerans* may be used, which is described as SEQ ID No.17 in the sequence listing. When the DNA of the D-amino acid transaminase gene derived from *Bacillus macerans* as described as SEQ ID No.17 in the sequence listing is used, the D-amino acid transaminase described as SEQ ID No.18 in the sequence listing may be obtained. Herein, the gene encoding the D-amino acid transaminase from *Bacillus macerans* and the amino acid sequence thereof are first elucidated by the inventors.

The origin of the D-amino acid transaminase gene is not limited to it. Any gene encoding D-amino acid transaminase generating an intended D-glutamate derivative may be satisfactory.

In case of mass production of a protein using recombinant DNA technology, microbial cells, actinomycetes cells, yeast cells, fungal cells, plant cells, animal cells or the like may be used as the host cells to be transformed. Among them, microorganisms, for which the knowledge with recombinant DNA technology exists, include for example *Bacillus, Pseudomonas, Brevibacterium, Corynebacterium, Streptomyces* and *Escherichia coli*. Owing to numerous findings about the technique for mass production of protein using bacteria of *Escherichia*, bacteria of *Escherichia* are generally used. Preferably, *Escherichia coli* is used.

Using vectors such as plasmid or phage carrying the intended gene of a transaminase, the gene may satisfactorily be introduced into these microorganisms. Otherwise, the intended gene may be integrated into the chromosome of the cell by homologous recombination. So-called multi-copy plasmid vectors are preferable and include for example plasmids with an origin of replication as derived from Col E1 as the vector for *Escherichia coli*, which are for example pUC-base plasmids, pBR322-base plasmids or derivatives thereof. For these vectors, promoters for general use in protein production in *Escherichia coli* may be used as the promoter for expressing the intended transaminase gene and include strong promoters for example T7 promoter, trp promoter, lac promoter, tac promoter and PL promoter. To increase the productivity, a terminator as a transcription termination sequence is preferably conjugated to the downstream of the protein gene. Such terminator includes for example T7 terminator, fd phage terminator, T4 terminator, terminators for tetracycline resistant gene, and terminators for *Escherichia coli* trp A gene. Additionally for screening transformants, preferably, the vector has a marker such as ampicillin resistant gene. As such plasmids, expression vectors with strong promoters are commercially available, such as pUC series (manufactured by TAKARA BIO INC.), pPROK series (manufactured by Clontech Laboratories, Inc.), and pKK233-2 (manufactured by Clontech Laboratories, Inc.).

For a method for culturing a microorganism generating an enzyme for use in reaction 3, culture media for general use in the field, namely culture media containing carbon sources, nitrogen sources, inorganic salts, trace metal salts, and vitamins may be used. Depending on the type of a microorganism or the culture conditions, about 0.1 to 1.0 g/dl of amino compounds such as amino acid is added to such culture medium, to promote the transamination activity.

When culturing genetic recombinant cells, chemicals such as ampicillin, kanamycin, neomycin and chloramphenicol may be appropriately added in a manner depending on the selected marker for the vector. Depending on the promoter carried on the vector, the expression level of the recombinant gene may be raised by adding an appropriate amount of an induction agent. In case of conjugating an intended gene to the downstream of the lac promoter to construct a vector, in one example, isopropyl 1-thio-β-D-galactopyranoside (IPTG) is possibly added at an amount to a final concentration range of 0.1 mM to 5 mM. Instead, galactose may be added appropriately to a final concentration of 0.1 to 5 g/dl, preferably 0.5 g/dl to 2 g/dl.

As substances for use as the culture medium components, for example, any carbon source that is compatible with the microorganism to be used may be satisfactory with no specific limitation. For example, glucose, sucrose, fructose, glycerol and acetic acid or mixtures of them may be used. As the nitrogen source, ammonium sulfate, ammonium chloride, urea, yeast extract, meat extract, corn steep liquor, and casein hydrolyzed products or mixtures of them may be used. As a culture medium composition, for example, a culture medium containing 0.5 g/dl fumaric acid, 1 g/dl yeast extract, 1 g/dl peptone, 0.3 g/dl ammonium sulfate, 0.3 g/dl $K_2HPO_4$, 0.1 g/dl $KH_2PO_4$, 1 mg/dl $FeSO_4.7H_2O$, and 1 mg/dl $MnSO_4.4H_2O$, pH 7.0 is listed.

The culture temperature is generally within a range where microorganisms used may grow, namely a range of 10 to 45° C. The temperature is preferably within a range of 20 to 40° C., more preferably within a range of 25 to 37° C. The pH of the culture medium is adjusted to a range of preferably 2 to 12, more preferably 3 to 10, still more preferably 4 to 8. The aeration conditions are set to conditions suitable for the growth of microorganisms used. Aerobic conditions are preferable. The culture period is generally about 12 to 120 hours, preferably about 24 to 96 hours.

(C-2) Reaction Conditions for Reaction 3

The reaction 3 characteristically produces glutamate derivatives of the general formula (2) from the substituted α-keto acid represented by formula (1).

The term "in the presence of an enzyme" for reaction 3 means that the enzyme should exist at its state to enable the generation of glutamate derivatives of formula (2) from the substituted α-keto acid represented by formula (1) in the reaction system. In other words, the enzyme may exist at any state in the reaction system as long as the enzyme may convert the substituted α-keto acid represented by formula (1) to the glutamate derivative general formula (2). For example, the enzyme may singly be added to the reaction system.

Otherwise, a microorganism with the enzyme activity (e.g. microorganism generating the enzyme, cells transformed with recombinant DNA, etc.), a culture of the microorganism (e.g., liquid culture, solid culture, etc.), a culture medium (e.g., cultures from which microbial cells are preliminarily eliminated), and treated products of the culture may also be added to the reaction system. When using cultures of microorganisms, reaction 3 may be progressed concurrently with culturing the microorganisms, or reaction 3 may be performed using cultures preliminarily prepared for obtaining the enzyme.

Herein, the term "treatment" means treatment for the purpose of recovering the enzyme in microbial cells and includes for example treatments with ultrasonication, glass bead, French press, and freeze-drying and treatments with lysed enzyme, organic solvents, detergents and the like. The treated products after these treatments may be further treated by routine processes (liquid chromatography, ammonium sulfate and the like), to recover crude fractionated enzymes or purified enzymes. When these enzymes have the required ability, they also may be used.

Furthermore, the culture or treated product when used may be included in carrageenan gel or polyacrylamide or may be immobilized on films of polyether sulfone, regenerated cellulose and the like.

In reaction 3, the substituted α-keto acid as the substrate includes for example the substituted α-keto acid represented by formula (1).

The reaction system may satisfactorily contain coenzymes, detergents, organic solvents and the like to accelerate the reaction. So as to increase the permeability of the substituted α-keto acid as the substrate into microbial cells, for example, detergents such as Triton X and Tween and organic solvents such as toluene and xylene may also be used. Further, coenzymes such as pyridoxal-5-phosphate may also be added to the culture medium.

When dividing the culture for the generation of the enzyme and the reaction 3 and then sequentially carrying out these steps, the latter reaction 3 step is not necessarily done in an aerobic atmosphere. In an anaerobic atmosphere, rather, reaction 3 may be performed in a reaction system from which dissolved oxygen in the reaction solution is removed with nitrogen gas substitution, argon gas substitution and sodium sulfite addition.

The reaction temperature is generally within a temperature range where the enzyme used may be active, preferably within a range of 10 to 50° C., more preferably within a range of 20 to 40° C., and still more preferably within a range of 25 to 37° C. The pH of the reaction solution is adjusted to a range of generally 2 to 12, preferably 6 to 11 and more preferably 7 to 9. The reaction time is generally about 1 to 120 hours, preferably about 1 to 72 hours and more preferably about 1 to 24 hours.

When determining the glutamate derivative or the substituted α-keto acid quantities in the liquid culture or the reaction solution, further, the glutamate derivative or the substituted α-keto acid may be assayed immediately using well-known methods. For simple procedure, thin layer chromatography using "Silica gel 60F254" manufactured by Merck Ltd. may be used. For enhancing the analytical precision, high performance liquid chromatography (HPLC) utilizing optical resolution columns such as "Inertsil ODS-80A" manufactured by GL Sciences, Inc. and "CROWNPAK CR (+)" manufactured by Daicel Chemical Industries, Ltd. may be used. In such manner, the glutamate derivative accumulated in the liquid culture or the reaction solution may be collected from the liquid culture or the reaction solution by routine methods, prior to use. For the collection from the liquid culture or the reaction solution, an appropriate combination of well-known measures for general use in this field, for example procedures such as filtration, centrifugation, vacuum concentration, ion exchange chromatography, adsorption chromatography and crystallization may be used.

The intended glutamate derivative may be obtained in the free form. If necessary, the glutamate derivative may also be recovered in a salt form thereof. The salt form includes salts thereof with bases. For example, inorganic bases such as sodium hydroxide, potassium hydroxide and calcium hydroxide and organic bases such as ammonia and various amines are listed.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding may be obtained by reference to certain specific examples, which are provided herein for purposes of illustration only, and are not intended to be limiting unless otherwise specified.

EXAMPLES

The invention is now described in detail in the following examples, but the invention is not limited to only these examples.

Example 1

Example 1 relates to reaction 1 of the invention. In Example 1, L-tryptophan, indole-3-pyruvic acid and indoleacetic acid are measured by high performance liquid chromatography (column: Inertsil ODS-2 (4.6×250 mm); column temperature: 40° C.; eluate: 0.1 M $KH_2PO_4$—$H_3PO_4$ (pH=2.80)/$CH_3CN$=1/9 to 5/5; flow rate of 1.0 ml/min; detection: UV 210 nm).

(1-1) Generation of indole-3-pyruvic acid from L-Trp Via the Reaction of Microbial Cells with Amino Acid Oxidase (Deaminase) Activity 50 ml of a culture medium, pH 7.0 containing 1 g/dl yeast extract, 1 g/dl polypeptone, 0.3 g/dl $(NH_4)_2SO_4$, 0.3 g/dl $K_2HPO_4$, 0.1 g/dl $KH_2PO_4$, 0.05 g/dl $MgSO_4.7H_2O$, 1 mg/dl $FeSO_4 \cdot 7H_2O$, and 1 mg/dl $MnSO_4 \cdot 4H_2O$ are placed in a 500-ml Sakaguchi flask for sterilization at 110° C. for 10 minutes.

Innocluate a culture medium with one loop of *Achromobacter* sp. AJ2425, *Proteus rettgeri* or *Morganella morganii* preliminarily cultured in a bouillon agar culture medium at 30° C. for 24 hours. Culture with agitation at 30° C. for 24 hours. After culturing, harvest microbial cells from the culture by centrifugation, individually rinse in 50 ml of 20 mM Tris-HCl buffer, pH 7.6, and prepare as rinsed microbial cells, again by centrifugation.

Add the wet microbial cells to a reaction solution of 1 g/dl L-tryptophan and 20 mM Tris-HCl buffer, pH 8.0 to a wet microbial cell weight of 1 w/v %. Transfer 1 ml of the reaction solution into a 5-ml test tube, shake at 30° C. for one hour to facilitate the product conversion. After the completion of the reaction, measure the amount of generated indole-3-pyruvic acid, the amount of residual L-tryptophan (L-Trp) and the amount of the by-product indoleacetic acid (IAA) (see Table 1).

TABLE 1

Amount of indole pyruvic acid generated from L-tryptophan

| Strains | L-Trp (g/dl) | IPA (g/dl) | IAA (g/dl) |
| --- | --- | --- | --- |
| *Achromobacter* sp. AJ2425 | 0.02 | 0.97 | 0.03 |
| *Proteus rettgeri* IFO13501 | 0 | 0.98 | 0.03 |
| *Morganella morganii* IFO3168 | 0 | 0.99 | 0.02 |

Consequently, indole-3-pyruvic acid is accumulated in any of the experimental lots where the reaction with the rinsed microbial cells is performed. Thus, indole-3-pyruvic acid is almost quantitatively generated from 1 g/dl L-tryptophan.

(1-2) Recovery of Indole-3-Pyruvic Acid by Nitrogen Gas Substitution Treatment of the Reaction Solution with the Rinsed Microbial Cells of *Morganella Morganii IFO*3168 and Crystallization in Hydrochloric Acid (a) Preparation of the Reaction Solution with the Rinsed Microbial Cells of *Morganella morganii*

By the same method as in (1-1), the rinsed microbial cells of *Morganella morganii* were prepared. Six Sakaguchi's flasks containing 50 ml of the reaction solution of 1 g/dl L-tryptophan and 20 mM Tris-HCl buffer, pH 8.0 were prepared. The wet microbial cells prepared were added to the individual flasks to a wet microbial cell weight of 1 w/v %, for reaction under shaking at 30° C. for one hour. After the completion of the reaction, the microbial cells were removed by centrifugation, to obtain the reaction solution of about 290 ml.

(b) Recovery of Indole-3-Pyruvic Acid by Nitrogen Gas Substitution of the Reaction Solution and Acid Crystallization 74 ml of the reaction solution obtained in (a) were transferred into a round-bottom flask for nitrogen gas substitution. Hydrochloric acid was added so as to adjust the reaction solution to pH 2 or less. 15 ml of 6N hydrochloric acid were added to 74 ml of the reaction solution (to a final hydrochloric acid concentration of about 1 N), and the mixture is stirred at 20° C. Through the procedure, the crystal was deposited. 24 hours later, the mixture was filtered. The resulting crystal was rinsed in 15 ml of water. The wet crystal thus obtained was dried under reduced pressure at 40° C., and obtained indole-3-pyruvic acid was 684 mg (yield of 79.5% from the starting tryptophan). The resulting indole-3-pyruvic acid was a yellowish white crystal, and the content was 97.2 wt % by high performance liquid chromatography (HPLC).

(c) Recovery of Indole-3-Pyruvic Acid by Acid Crystallization of Reaction Solution 66 ml of the reaction solution obtained in (a) were transferred into a round-bottom flask. 6N Hydrochloric acid of 13 ml was added so as to adjust the reaction solution to pH 2 or less and stirred at 20° C. Through the procedure, the crystal was deposited. 24 hours later, the mixture was filtered. The resulting crystal was rinsed in 13 ml of water. The wet crystal thus obtained was dried under reduced pressure at 40° C., to obtain indole-3-pyruvic acid at 538 mg (yield of 58.2% from the starting tryptophan). The resulting indole-3-pyruvic acid was a dark brown crystal, and the content was 80.5 wt % measured by high performance liquid chromatography (HPLC).

(d) Comparison of the Obtained Indole-3-Pyruvic Acid

The indole-3-pyruvic acid (IPA) thus obtained in (b) was compared with that obtained in (c) in terms of crystal quality (see Table 2).

As apparently shown from these results, the lot (b) having involved nitrogen gas substitution included a higher IPA content and a reduced content of the by-product indoleacetic acid (IAA) as an impurity in the crystal. Further, the coloring of the resulting crystal was suppressed in the lot having involved nitrogen gas substitution. The crystals in the individual lots was diluted to 10 mg/dl, of which the transmittance at 450 nm and 400 nm was then measured. It was confirmed that the transmittance in the nitrogen gas substitution lot was reduced, i.e. the coloring via decomposition was suppressed.

TABLE 2

| | IPA crystal quality | |
| --- | --- | --- |
| | With nitrogen substitution (b) | Without nitrogen substitution (c) |
| IPA content in crystal | 97.30% | 80.50% |
| IAA content in crystal | 0.18% | 1.54% |
| Crystal color | yellowish white | dark brown |
| Transmittance (450 nm) | 96.9% T | 82.9% T |
| Transmittance (400 nm) | 94.1% T | 75.9% T |

As apparently shown in the results, indole-3-pyruvic acid may efficiently be produced from tryptophan in a simple manner.

Example 2

In Example 2, the reaction 2 is performed using a chemical synthetic system.

(2-1) Synthesis of 4-(indol-3-ylmethyl)-4-hydroxy-2-oxoglutaric acid (IHOG)

7.50 g of indole-3-pyruvic acid (35.8 mmol; content of 97.0% by weight) and 14.18 g of oxaloacetic acid (107.4 mmol) are added to and dissolved in 64.45 ml of water preliminarily dissolving 18.91 g of potassium hydroxide (286.5 mmol; content of 85% by weight) therein. The mixture solution is agitated at 35° C. for 24 hours.

Further, 40.0 ml of 3N hydrochloric acid is added for neutralization (pH 7.0), to obtain a neutralized reaction solution of 153.5 g. The neutralized reaction solution contained 5.55 g of IHOG, so the yield is 53.3% (vs. indole-3-pyruvic acid).

Water is added to the neutralized reaction solution to 168 ml and is passed through a resin column (diameter of 4.8 cm) packed with 840 ml of a synthetic adsorbent (DIAION-SP207 manufactured by Mitsubishi Chemical Corporation). Further, pure water is passed through the column at a flow rate of 23.5 ml/minute, to collect 1.73 to 2.55 (L/L-R) to obtain an aqueous solution containing 3.04 g of IHOG at high purity at a yield of 54.7% (vs. the charged amount to the resin).
(NMR Measurement)
$^1$H-NMR (400 MHz, D$_2$O): 3.03 (d, 1H, J=14.6 Hz), 3.11 (d, 1H, J=14.6 Hz), 3.21 (d, 1H, J=18.1 Hz), 3.40 (d, 1H, J=18.1 Hz), 7.06-7.15 (m, 3H), 7.39 (d, 1H, J=7.8 Hz), 7.66 (d, 1H, J=7.8 Hz).
$^{13}$C-NMR (100 MHz, D$_2$O): 35.43, 47.91, 77.28, 109.49, 112.05, 119.44, 119.67, 121.91, 125.42, 128.41, 136.21, 169.78, 181.43, 203.58

(2-2) Synthesis of 4-phenylmethyl-4-hydroxy-2-oxoglutaric acid (PHOG)

5.0 g (30.5 mmol) of phenylpyruvic acid and 12.1 g (91.4 mmol) of oxaloacetic acid are added to 25 ml of water preliminarily dissolving 13.8 g of potassium hydroxide (purity of 85%) therein, for reaction at ambient temperature for 72 hours. Using the conc. hydrochloric acid, the reaction solution is adjusted to pH 2.2, for extraction into ethyl acetate. The organic layer is rinsed with saturated aqueous sodium chloride, dried over anhydrous magnesium sulfate and concentrated to obtain the residue. The residue is recrystallized in ethyl acetate and toluene to obtain PHOG of 2.8 g (11.3 mmol.) in crystal.
(NMR Measurement)
$^1$H NMR (D$_2$O) δ: 2.48 (d, J=14.4 Hz, 0.18H), 2.60 (d, J=14.4 Hz, 0.18H), 2.85-3.30 (m, 3.64H), 7.17-7.36 (m, 5H)
(Measurement of Molecular Weight)
Theoretical value by ESI-MS: C$_{12}$H$_{12}$O$_6$=252.23
Experimental value: 251.22 (MH$^-$)

Example 3

In example 3, reaction 2 is performed using an enzymatic system. In Example 3, herein, IHOG and PHOG used as substrates are synthetically prepared by the method described in Example 2.
(3-1) Screening of Microorganism with the Activity of Aldolase for PHOG (Referred to as PHOG Activity Hereinafter)
Screening of microbial strains having the aldolase activity is performed, wherein 4-phenylmethyl-4-hydroxy-2-oxoglutaric acid (PHOG) is used as a substrate.
Test microorganisms (bacteria and yeast) are inoculated on a bouillon plate culture medium (Eiken Chemical Co., Ltd.), for culturing at 30° C. for 24 hours. The resulting culture is inoculated on a plate containing 0.5 g/dl glycerol, 0.5 g/dl fumaric acid, 0.3 g/dl yeast extract, 0.2 g/dl peptone, 0.3 g/dl ammonium sulfate, 0.3 g/dl K$_2$HPO$_4$, 0.1 g/dl KH$_2$PO$_4$, 0.05 g/dl MgSO$_4$.7H$_2$O, 0.25 g/dl sodium phthalate, and 2 g/dl agar powder (pH 6.5), for culturing at 30° C. for 24 hours. The resulting microbial cells are then inoculated in a reaction solution of 100 mM Tris-HCl, pH 8.0, 50 mM PHOG, 1 mM MgCl$_2$, 5 mM potassium phosphate solution (KPi) and 1 v/v % toluene to a wet microbial cell weight of about 1 w/v %, for reaction at 30° C. for 24 hours.
The concentration of the free pyruvic acid in the reaction solution is measured by an enzymatic method using lactate dehydrogenase (LDH). 10 μL of sample is added to 200 μL of a reaction solution of 100 mM Tris-HCl, pH 8.0, 1.5 mM NADH, 5 mM MgCl$_2$, and 25 U/ml LDH, for incubation at 30° C. for 10 minutes. The absorbance at 340 mM is measured after the reaction, to determine the amount of pyruvic acid in the sample, based on a reduction in the amount of NADH.

Additionally, the amount of the phenylpyruvic acid generated is assayed by HPLC analysis using "Inertsil ODS-2" (5 μM, 4.6×250 mm) manufactured by GL Sciences, Inc. The analytical conditions are as follows.
Mobile phase: 20 v/v % acetonitrile/aqueous 0.05 v/v % trifluoroacetic acid solution
Flow rate: 1 ml/min
Column temperature: 40° C.
Detection: UV 210 nm.
Under these conditions, PHOG is eluted at a retention time of about 9.8 minutes, while phenylpyruvic acid is eluted at a retention time of about 12 minutes. These are individually fractionated and assayed.
The value of the amount of pyruvic acid or phenylpyruvic acid generated from PHOG in the test microbial cell-added lot minus the amount thereof in the control lot (no microbial cell-added lot) is defined as the amount thereof generated with aldolase. Consequently, the aldolase activity for the substrate PHOG in the microbial strains is shown in Table 3.

TABLE 3

Screening results of microbial strains with PHOG aldolase activity

| Strains | Pyruvic acid (mM) | Phenylpyruvic acid (mM) |
|---|---|---|
| *Pseudomonas taetrolens* ATCC4683 | 34.9 | 35.0 |
| *Pseudomonas coronafaciens* AJ2791 | 33.6 | 33.9 |
| *Pseudomonas desmolytica* AJ1582 | 1.1 | 2.9 |
| *Erwinia* sp. AJ2917 | 0.8 | 3.0 |
| *Flavobacterium rhenanum* AJ2468 | 3.0 | 6.1 |
| *Xanthomonas citri* AJ2797 | 1.0 | 3.2 |

*Pseudomonas taetrolens* ATCC4683 is selected, and the PHOG synthetic reaction from phenylpyruvic acid and oxaloacetic acid or pyruvic acid is examined. The microbial cells of *P. taetrolens* ATCC4683 (AJ2212) are inoculated in a reaction solution of 100 mM Tris-HCl, pH 8.0, 50 mM phenylpyruvic acid, 1 mM MgCl$_2$, 5 mM KPi, 100 mM oxaloacetic acid or pyruvic acid and 1 w/w % toluene to a final concentration of about 1 w/v %, for reaction at 30° C. for 16 hours. After the completion of the reaction, the amount of PHOG generated is assayed by HPLC. The amount of PHOG generated from phenylpyruvic acid and oxaloacetic acid or pyruvic acid is shown in Table 4.

TABLE 4

Amount of PHOG generated from phenylpyruvic acid and oxaloacetic acid or pyruvic acid

| | Oxaloacetic acid lot | Pyruvic acid lot |
|---|---|---|
| Microbial cell-added lot | 14.3 mM | 9.3 mM |
| Control lot (Mg added) | 8.6 | 1.7 |
| Control lot (no Mg added) | Trace | N.D. |

Table 4 shows that the amount of PHOG generated in the microbial cell-added lot increased and that the activity of aldolase may generate PHOG from any combinations of phenylpyruvic acid+oxaloacetic acid and of phenylpyruvic acid+pyruvic acid.
(3-2) Purification of aldolase derived from *Pseudomonas taetrolens* ATCC4683 for IHOG
Aldolase for IHOG (sometimes referred to as IHOG aldolase hereinafter) is purified as follows from a soluble fraction of the *P. taetrolens* strain ATCC4683. As to the assaying of the aldolase activity, the aldol decomposition (retroaldol) activity using PHOG as the substrate is measured under the following conditions.

Reaction conditions: 50 mM Tris-HCl, pH 8.0, 2 mM PHOG, 0.2 mM NADH, 0.2 mM KPi, 1 mM $MgCl_2$, 16 U/ml lactate dehydrogenase, and 3 μl enzyme/600 μl reaction solution, for the measurement of absorbance at 30° C. and 340 nm.

1. Preparation of Soluble Fraction

One loop of the microbial cells of *P. taetrolens* ATCC4683 preliminarily cultured in a bouillon plate culture medium at 30° C. for 24 hours is inoculated in a 500-ml flask containing 50 ml of an enzyme-generating culture medium (0.5 g/dl glycerol, 0.5 g/dl fumaric acid, 0.5 g/dl ammonium sulfate, 0.3 g/dl $K_2PO_4$, 0.1 g/dl $KF_2PO_4$, 0.05 g/dl $MgSO_4.7H_2O$, 0.3 g/dl yeast extract, 0.2 g/dl peptone, 0.25 g/dl sodium phthalate, and 0.005% Antifoam A (manufactured by Sigma). After adjustment to pH 6.5 with KOH), the culture is incubated with agitation at 30° C. for 24 hours.

0.5 ml of the liquid culture is inoculated in 40 flasks of a 500-ml volume, each of the flasks containing 50 ml of the enzyme-generating culture medium, for culturing under shaking at 30° C. for 24 hours. The microbial cells are harvested from the resulting liquid culture by centrifugation, and suspended and washed in buffer A (20 mM Tris-HCl, pH 7.6), followed by centrifugation again for harvesting the microbial cells. The resulting washed microbial cells are suspended in 200 ml of buffer A, for ultrasonic disruption at 4° C. for 30 minutes. The solution after the disruption is centrifuged (×8,000 rpm, 10 minutes×two times) to remove the residual microbial cells, followed by additional ultra-centrifugation (×50,000 rpm, 30 minutes) to recover the resulting supernatant, which is defined as soluble fraction.

2. Anion Exchange Chromatography: Q-Sepharose FF 80 ml of the soluble fraction is treated in an anion exchange chromatography column Q-Sepharose FF 26/10 (manufactured by Pharmacia, CV=20 ml), for adsorption onto the carrier. Proteins that did not adsorb onto the carrier (non-adsorbed proteins) are washed out, using Buffer A. Subsequently, the adsorbed protein is eluted while the KCl concentration is changed linearly from 0 M to 0.7 M (in total of 140 ml). By detecting the activity of aldolase for PHOG (sometimes referred to as PHOG aldolase hereinafter) in each of the eluted fractions, the PHOG aldolase activity peak is detected in the fraction corresponding to about 0.5 M. The same chromatographic procedures are repeatedly carried out for two times.

3. Hydrophobic Chromatography: Phenyl Sepharose HP HR 16/10

The solution with the detected aldolase activity is collected and dialyzed with Buffer B (50 mM Tris-HCl, pH 7.6, 1M ammonium sulfate, pH 7.6) at 4° C. overnight and then filtered through a 0.45-1 μm filter. The resulting filtrate is treated with a hydrophobic chromatography column Phenyl Sepharose HP HR 16/10 (manufactured by Pharmacia) equilibrated with Buffer B. Through the procedures, the aldolase is adsorbed on the carrier.

The non-adsorbed proteins that had not been adsorbed on the carrier are washed out, using Buffer B. Subsequently, the aldolase is eluted while linearly changing the ammonium sulfate concentration from 1M to 0 M. By measuring the aldolase activity in each of the eluted fractions, the aldolase activity peak is detected in the fraction corresponding to about 0.2 M of the ammonium sulfate concentration.

4. Gel Filtration Chromatography: Sephadex 200 HP 16/60

Individual fractions containing aldolase are combined and dialyzed with Buffer A, and filtered through a 0.45-μm filter. The resulting filtrate is concentrated with an ultrafiltration membrane centriprep 10 and, subsequently is treated with a gel filtration Sephadex 200 HP 16/60 (manufactured by Pharmacia) equilibrated with Buffer C (20 mM Tris-HCl, pH 7.6, 0.1 M KCl) for elution at a flow rate of 1 ml/min. Through the procedures, the aldolase is eluted in fractions from 66 to 71 ml. Based on the position of the activity peak eluted, it is estimated that the molecular weight of the aldolase would be about 146 kDa.

5. Anion Exchange Chromatography: Mono Q HR5/5

The resulting fractions are filtered through a 0.45-μm filter. The resulting filtrate is treated with an anion chromatography column Mono-Q HR 5/5 (manufactured by Pharmacia) equilibrated with Buffer A. Through the procedures, the aldolase is adsorbed on the carrier. The non-adsorbed proteins are washed out, using Buffer A. Subsequently, the protein is eluted while the KCl concentration is linearly changed from 0 mM to 700 mM (in total of 24 ml). By measuring the aldolase activity in each eluted fractions, the aldolase activity peak is detected in the fraction corresponding to about 0.4 M of the KCl concentration.

6. Hydroxyapatite Chromatography: CHT-II

The resulting fraction is dialyzed with Buffer D (10 mM potassium phosphate buffer, pH 7.0) at 4° C. overnight, and filtered through a 0.45-μm filter. The resulting filtrate is treated with a hydroxyapatite chromatography column CHT-II 5 ml (manufactured by Bio-Rad Laboratories Inc.) equilibrated with Buffer D. Through the procedures, the aldolase can be separated from the adsorbed proteins because the aldolase is not adsorbed on the carrier.

The fraction purified by the aforementioned column chromatographic procedures is treated with SDS-PAGE. An almost single band at a position corresponding to about 25 kDa is detected. Because it is estimated by gel filtration chromatography that the molecular weight is about 146 kDa, it is speculated that the aldolase would be forming a hexamer. Table 5 shows purification tables.

TABLE 5

Purification table of *Pseudomonas taetrolens* strain ATCC4683-derived IHOG aldolase

| | protein (mg) | specific activity (U/mg) | purification fold | total activity (U) | yield (%) |
|---|---|---|---|---|---|
| soluble fraction | 3750 | 0.014 | 1 | 51 | 100 |
| Q-sepharose HP 26/10 | 510 | 0.060 | 4.4 | 30.5 | 59.8 |
| Phenyl sepharose HP 16/10 | 21.2 | 0.893 | 66 | 19.0 | 37.2 |
| Sephadex200 HP 16/60 | 1.9 | 4.643 | 341 | 8.65 | 17.0 |
| monoQ HR5/5 | 0.49 | 10.89 | 800 | 5.33 | 10.4 |
| Hydroxyapatite CHT-II | 0.025 | 28.70 | 2110 | 0.71 | 1.4 |

(3-3) Determination of Internal Amino Acid Sequence of IHOG Aldolase

About 2 μg portion of the purified aldolase is treated for SDS-PAGE and separated thereby. Subsequently, the sample in the SDS-PAGE gel is treated with trypsin (pH 8.5, 35° C., 20 hours) and treated by reverse-phase HPLC to separate fragmental peptides. The amino acid sequences of two of the separated fractions are determined as follows, which are composed of 20 residues and 12 residues as SEQ ID Nos. 4 and 5, respectively.

TABLE 6

Internal amino acid sequence determined

| | |
|---|---|
| SQ ID No. 4 | SLLDA FQNVV TPHIS DNLGR |
| SQ ID No. 5 | AEIAT GALDQ SW |

(3-4) Cloning of the Gene of *P. taetrolens* Strain ATCC4683-Derived IHOG Aldolase 1. Preparation of Chromosomal DNA The *P. taetrolens* strain ATCC4683 is cultured in 50 ml of a bouillon culture medium at 30° C. overnight (pre-culture). 5 ml of the liquid culture is used as a seed bacterium, for culturing in 50 ml of a bouillon culture medium. After culturing up to the latter logarithmic growth stage, 50 ml of the liquid culture is treated by centrifugation (12,000×g, 4° C., 15 minutes) to harvest the microbial cells. Using the microbial cells, the chromosomal DNA is prepared by the routine method.

2. Identification of Internal Sequence by PCR

Based on the internal amino acid sequence of the determined IHOG aldolase, the following mix primer (SEQ ID Nos. 6 and 7) is prepared.

TABLE 7

Mix primer designed and synthesized on the basis of the internal amino acid sequence

| | |
|---|---|
| SQ ID No. 6 | TTY CAR AAY GTS GTS ACS CCS C |
| SQ ID No. 7 | TGR TCR ATN GCN CCS GTN GCR ATY TCN GC |

Using the prepared primer mix, PCR amplification is performed using the chromosomal DNA of *P. taetrolens* strain ATCC4683 as a template. The PCR is performed using PCR Thermal PERSONEL (manufactured by TAKARA BIO INC.) for 30 cycles under the following conditions:

94° C. for 30 seconds
55° C. for 30 seconds
72° C. for 1 minute.

PCR products are treated by agarose gel electrophoresis, so that a fragment of about 500 bp is amplified. The DNA fragment is cloned in pUC18, for the determination of the nucleotide sequence. The amino acid sequence speculated on the basis of the recovered DNA fragment is identical to the internal amino acid sequence of the IHOG aldolase, so that the recovery of the intended aldolase gene is confirmed.

3. Cloning of the Full-Length Gene by Colony Hybridization

It is attempted to recover the full-length gene using the PCR-amplified DNA fragment by Southern analysis and colony hybridization. The DNA probe is prepared using DIG High Prime (manufactured by Roche Diagnostics) according to the instruction manual, and then, the probe is labeled by overnight (O/N) incubation at 37° C.

Southern analysis is done by completely digesting 1 μg of the chromosomal DNA with various restriction enzymes, electrophoresis on 0.8% agarose gel, blotting on nylon membrane and other procedures following the manual. Hybridization is performed using DIG Easy Hyb (manufactured by Roche Diagnostics), for pre-hybridization at 50° C. for one hour. Then, the probe is added for overnight hybridization. The bands are detected, using DIG Nucleotide Detection Kit. Consequently, a PstI fragment of about 4 kbp is detected that strongly hybridized with the PCR fragment as a probe.

Then, the PstI fragment is recovered by colony hybridization. 20 μg of the chromosomal DNA is treated with PstI and treated with agarose gel electrophoresis, to recover a fragment of about 4 kbp. The fragment is conjugated into pUC118, to prepare a library in *E. coli* JM109. The colony is transferred onto a nylon membrane filter (Hybond-N, manufactured by Amersham), followed by alkali denaturation, neutralization and immobilization. Hybridization is performed, using DIG Easy Hyb. The filter is immersed in a buffer, for one-hour prehybridization at 42° C. Then, the prepared labeled probe is added, for hybridization at 42° C. for 16 hours. After rinsing in SSC, a colony hybridizing with the probe is detected, using DIG Nucleotide Detection Kit (manufactured by Roche Diagnostics). Consequently, a clone strongly hybridizing with the probe is obtained.

The nucleotide sequence of the plasmid DNA recovered from the resulting clone is determined. It is shown that the DNA had the nucleotide sequence described as SEQ ID No.1. The 678-bp orf containing the nucleotide sequence (the 507-th to 566-th positions and the 1046-th to 1082-th positions in SEQ ID No.1) is determined, which corresponds to the internal, determined amino acid sequence, and the intended full-length aldolase is obtained.

4. Expression of IHOG Aldolase in *E. coli* (NO.1)

Using the primers (SEQ ID Nos.8 and 9) shown in Table 8, the fragment amplified from the chromosomal DNA of the *P. taetrolens* strain ATCC4683 is treated with BamHI/HindIII and then inserted in the BamHI/HindIII site of pUC18, to construct a plasmid pUCALD. The constructed expression plasmid is introduced in *E. coli* JM109. The resulting transformant is agitated in an LB culture medium containing 50 μg/ml ampicillin at 37° C. day and night (pre-culture). Then, the liquid pre-culture is seeded at 1% in 50 ml of the LB culture medium, for culturing at 37° C. About 2 hours after the start of culture, IPTG is added to a final concentration of 1 mM, for additional 3-hour culture.

After the completion of culturing and expression of the gene under control of an inducible promoter, the microbial cells are harvested and rinsed, and those are suspended in 1 ml of 20 mM Tris-HCl, pH 7.6. The microbial cells are then disrupted using Multi-Bead Shocker (manufactured by Yasui Kikai Corporation). The solution after the disruption is centrifuged at 15,000 rpm for 10 minutes, so that the resulting supernatant is defined as crude enzyme solution.

TABLE 8

Primers

| | |
|---|---|
| SQ ID No. 8 ALD-5' | Bam(5'-GCC GGA TCC ACA AGG GTT CAG TCA TTC ATG G-3') |
| SQ ID No. 9 ALD-3' | Hind(5'-CCG AAG CTT TCA GTT CGC CAG GCC AGC C-3') |

Using the crude enzyme solution, the aldolase activity is measured using the substrate PHOG. While no PHOG aldolase activity is detected in *E. coli* harboring pUC18 (control), the PHOG aldolase activity of 0.81 U/mg·protein is observed in the strain harboring pUCADL. This indicates that the gene encodes the intended aldolase.

(3-5) Synthesis of 4-(indol-3-ylmethyl)-4-hydroxy-2-oxoglutaric acid (IHOG) from indole-3-pyruvic Acid and Pyruvic Acid, Using the Strain Expressing Aldolase The rinsed microbial cells of *E. coli* expressing aldolase as prepared in (3-4) are used as the enzyme source, for carrying out the synthesis of 4-(indol-3-ylmethyl)-4-hydroxy-2-oxoglutaric acid (IHOG) from indole-3-pyruvic acid and pyruvic acid. IHOG is quantitatively measured by HPLC using "Inertsil ODS-2" (5 μm, 4.6×250 mm) manufactured by GL Sciences, Inc. The analytical conditions are as follows.

Mobile phase: 40 v/v % acetonitrile/5 mM phosphate dihydrogen tetrabutylammonium solution
Flow rate: 1 ml/min
Column temperature: 40° C.
Detection: UV 210 nm The rinsed microbial cells of the aldolase-expressing *E. coli* are added to a reaction solution of 100 mM buffer (Tris-HCl, pH 8.0 or pH 9.0 and glycine-NaOH pH 10.0), 50 mM indole-3-pyruvic acid, 250 mM pyruvic acid, 1 mM MgCl2, and 1 v/v % toluene to 10 w/v %, for reaction under shaking at 33° C. for 4 hours. The enzyme reaction solution is appropriately diluted, for measuring the resulting IHOG.

TABLE 9

| Amount of IHOG generated with aldolase | | |
|---|---|---|
| pH | aldolase | IHOG (mM) |
| 8 | + | 9.2 |
| 8 | − | 0.42 |
| 9 | + | 12.1 |
| 9 | − | 1.6 |
| 10 | + | 10.7 |
| 10 | − | 5.4 |

Consequently, the amount of generated IHOG is increased in the aldolase-expressing *E. coli* addition lot. Generation of IHOG by aldolase is achieved.

(3-6) Mass Expression of IHOG Aldolase in *E. coli* (NO.2)

1. Construction of pTrp4 Plasmid Harboring Trp Promoter and Rrnb Terminator

Using the oligonucleotides in Table 10 as primers (a combination of SEQ ID Nos. 10 and 11), the promoter region in the trp operon on the chromosomal DNA of *E. coli* W3110 as the intended gene region is amplified by PCR. The resulting DNA fragment is ligated to the pGEM-Teasy vector (manufactured by Promega Ltd.). In the ligation solution, *E. coli* JM109 is transformed, to facilitate selection of a strain having the intended plasmid where the trp promoter is inserted along a direction inverse to the direction of the lac promoter among the resulting ampicillin resistant strains. Then, the plasmid is treated with Eco0109I/EcoRI, to obtain a DNA fragment containing the trp promoter, which is then ligated into the Eco0109I/EcoRI digestion product of pUC19 (manufactured by TAKARA BIO INC.). In the ligation solution, *E. coli* JM109 is transformed, to facilitate selection of a strain having the intended plasmid among the resulting ampicillin resistant strains. Then, the plasmid is designated as pTrp 1.

Then, pKK223-3 (manufactured by Amersham Pharmacia) is treated with HindIII/HincII, to obtain a DNA fragment containing the rrnB terminator, which is then ligated to a HindIII/PvuII digestion product of pTrp1. In this ligation solution, *E. coli* JM109 is transformed to obtain a strain with the intended plasmid among the resulting ampicillin resistant strains. The plasmid is designated as pTrp2.

Subsequently, the oligonucleotides in Table 10 as primers (a combination of SEQ ID Nos. 10 and 12) and pTrp2 as template are used for PCR to amplify the trp promoter region. The resulting DNA fragment is treated with Eco0109I/NdeI and ligated to the Eco0109I/NdeI digestion product of pTrp2. In the ligation solution, *E. coli* JM109 is transformed, to select a strain with the intended plasmid among the resulting ampicillin resistant strains. Then, the plasmid is designated as pTrp4.

TABLE 10

```
SQ ID No. 10  5'-side  GTATCACGAGGCCCTAGCTGTGGTGTCATGGTCGGTGATC
                               Eco0109 I SQ ID No. 11  3'-side  TTCGGGGATTCCATATGATACCCTTTTTACGTGAACTTGC
                               Nde I SQ ID No. 12  3'-side  GGGGGGGGCATATGCGACCTCCTTATTACGTGAACTTG
                               Nde I
```

2. Construction of Aldolase Gene-Expressing Plasmids ptrpALD1 and ptrpALD2 and Expression in *E. coli*

Using the primers shown in Table 11 (SEQ ID Nos. 9 and 13), a fragment amplified from the chromosomal DNA of *P. taetrolens* strain ATCC4683 is treated with NdeI/HindIII and inserted into the NdeI/HindIII site of pTrp4 to construct a plasmid ptrpALD1. The plasmid expresses the aldolase gene of the amino acid sequence SEQ ID No.3 from the 444-th ATG as the translation initiation codon in the nucleotide sequence SEQ ID No.1. Additionally using the primers (SEQ ID Nos. 9 and 14), a fragment amplified from the chromosomal DNA of *P. taetrolens* strain ATCC4683 is treated with NdeI/HindIII and inserted into the NdeI/HindIII site of pTrp4, to construct a plasmid ptrpALD2. The resulting plasmid expresses the aldolase gene of the amino acid sequence SEQ ID No.2 from the 456-th ATG as the translation initiation codon in the nucleotide sequence SEQ ID No. 1.

The individually constructed expression plasmids are introduced in *E. coli* JM109. The resulting transformant is shaken in an LB culture medium containing 50 μg/ml ampicillin at 37° C. day and night (pre-culture). 50 ml of the liquid pre-culture is seeded at 1% in 50 ml of the LB culture medium, for culturing at 37° C. About 2 hours after the start of the culture, IPTG is added to a final concentration of 1 mM, for additional 3-hour culture. After the completion of the culture, the microbial cells are harvested and rinsed, suspended in 1 ml of 20 mM Tris-HCl, pH 7.6, and disrupted with Multi-bead Shocker (manufactured by Yasui Kikai Corporation). The solution, after disruption, is centrifuged at 15,000 rpm for 10 minutes, and the resulting supernatant is defined as crude enzyme solution.

TABLE 11

| Primers |
|---|
| SQ ID No. 9   ALD-3' Hind (5'-CCG AAG CTT TCA GTT CGC CAG GCC AGC C-3') |
| SQ ID No. 13  ALD-5' Nde-1 (5'-GGT TCA GTC ACA TAT GGA GGT CGC TAT GTC-3') |

TABLE 11-continued

Primers

SQ ID No. 14 ALD-5' Nde-2 (5'-ATG GAG GTC CAT TAG TCA TTG CCC GGT TCA CGC-3')

Using the crude enzyme solution, the aldolase activity is measured using PHOG as the substrate. While no PHOG aldolase activity is detected in *E. coli* harboring pTrp4 (control), the PHOG aldolase activity of 16.1 U/mg·protein is observed in the strain harboring ptrpADL1, while the PHOG aldolase activity of 36.0 U/mg·protein is observed in the strain harboring ptrpADL2. This indicates that the aldolase of SEQ ID No.2 and 3 have aldolase activity.

Example 4

Example 4 relates to reaction 3 of the invention. In Example 4, herein, monatin and 4-phenylmethyl-4-hydroxyglutamic acid (PHG) are assayed by high performance liquid chromatography using "Inertsil ODS-80A" (5 μm, 6×150 mm) manufactured by GL Sciences, Inc. The analytical conditions are as follows.

Mobile phase: 12 v/v % acetonitrile/aqueous 0.05 v/v % trifluoroacetic acid solution
Flow rate: 1.5 ml/min
Column temperature: 30° C. and
Detection: UV 210 nm Under the analytical conditions, (2S,4S)-monatin and (2R,4R)-monatin with a retention time of 12.1 minutes, (2S,4R)-monatin and (2R,4S)-monatin with a retention time of 9.7 minutes, (2S,4S)-PHG and (2R,4R)-PHG with a retention time of 7.2 minutes, and (2S,4R)-PHG and (2R,4S)-PHG with a retention time of 6.0 minutes are fractionated and assayed.

If necessary, additionally, analysis by HPLC using an optical resolution column "CROWNPAK CR (+)" (4.6×150 mm) manufactured by Daicel Chemical Industries, Ltd. is done. The analytical conditions are as follows.

(In case of monatin)
Mobile phase: aqueous perchloric acid solution, pH 1.5/10 v/v % methanol
Flow rate: 0.5 ml/min
Column temperature: 30° C. and
Detection: UV 210 nm Under the analytical conditions, optical monatin isomers (2R,4S), (2R,4R), (2S,4R) and (2S,4S) are fractionated and assayed at retention times of 42, 57, 64, and 125 minutes in this order.

(In case of PHG)
Mobile phase: aqueous perchloric acid solution, pH 1.5
Flow rate: 1 ml/min
Column temperature: 30° C. and
Detection: UV 210 nm Under the analytical conditions, optical PHG isomers (2R,4S), (2R,4R), (2S,4R) and (2S,4S) at retention times of 20 minutes, 28 minutes, 31 minutes and 46 minutes in this order may be fractionated and assayed.

(4-1) (2S,4S)-Monatin Production with L-Amino Acid Transaminase

Microorganisms shown below in Table 12 are inoculated on a bouillon plate culture medium (Eiken Chemical Co., Ltd.), and cultured at 30° C. for 24 hours. The microbial cells are inoculated in 1 ml of a reaction solution of 100 mM Tris-HCl, pH 7.6, 30 mM IHOG, 100 mM L-glutamate monosodium, 1 mM pyridoxal-5'-phosphate, and 0.5 (v/v) toluene to a wet microbial cell weight of 5% by weight, for incubation at 30° C. for 16 hours. After the completion of the reaction, the monatin generated thereby is assayed. This is shown in Table 12. (2S,4S)-Monatin could be generated from IHOG.

TABLE 12

| Strains | Monatin generated (mM) |
|---|---|
| *Aeromonas hydrophila* IFO3820 | 1.2 |
| *Agrobacterium tumefaciens* IFO3058 | 1.9 |
| *Alcaligenes faecalis* ATCC8750 | 1.6 |
| *Beijerinckia indica* ATCC9037 | 0.2 |
| *Escherichia coli* ATCC12814 | 0.6 |
| *Proteus rettgeri* IFO13501 | 0.7 |
| *Morganella morganii* IFO3848 | 1.2 |

(4-2) (2S,4S)-PHG Production with L-Amino Acid Transaminase

Microorganisms shown below in Table 13 are inoculated on a bouillon plate culture medium (Eiken Chemical Co., Ltd.), for culturing at 30° C. for 24 hours. The microbial cells are inoculated in 1 ml of a reaction solution of 100 mM Tris-HCl, pH 7.6, 30 mM PHOG, 100 mM L-glutamate monosodium or L-aspartate monosodium, 1 mM pyridoxal-5'-phosphate, and 0.5 (v/v) toluene to wet microbial cells weight of 5% by weight, for incubation at 30° C. for 16 hours. After the completion of the reaction, the generated PHG is assayed. This is shown in Table 13. (2S,4S)-PHG could be generated from PHOG.

TABLE 13

| | PHG generated (mM) | |
|---|---|---|
| Strains | L-Glu | L-Asp |
| *Aeromonas hydrophila* IFO3820 | 8.9 | 8.9 |
| *Agrobacterium tumefaciens* IFO3058 | 8.2 | 8.0 |
| *Alcaligenes faecalis* ATCC8750 | 4.9 | 10.7 |
| *Beijerinckia indica* ATCC9037 | 7.4 | 2.7 |
| *Escherichia coli* ATCC12814 | 9.0 | 3.3 |
| *Proteus rettgeri* IFO13501 | 10.2 | 9.0 |
| *Morganella morganii* IFO3848 | 10.4 | 5.2 |

(4-3) (2S,4S)-PHG Production with L-Amino Acid Transaminase

Microorganisms shown below in Table 14 are inoculated on a bouillon plate culture medium (Eiken Chemical Co., Ltd.), and cultured at 30° C. for 24 hours. The culture medium containing 0.5 g/dl fumaric acid, 1 g/dl yeast extract, 1 g/dl peptone, 0.3 g/dl ammonium sulfate, 0.3 g/dl $K_2HPO_4$, 0.1 g/dl $KH_2PO_4$, 1 mg/dl $FeSO_4.7H_2O$, and 0.1 g/dl $MnSO_4.4H_2O$, pH 7.0 is divided in 50-ml portions in 500-ml Sakaguchi's flasks and sterilized at 110° C. for 10 minutes. Onto the resulting liquid culture medium is inoculated one loop and is cultured with agitation at 30° C. for 16 hours.

1 ml of the liquid culture was centrifuged, to obtain microbial cells, which are then rinsed and harvested with 20 mM Tris-HCl, pH 7.6 and are subsequently suspended in 1 ml of a reaction solution of 100 mM Tris-HCl, pH 7.6, 50 mM PHOG, 100 mM monosodium L-glutamate, 1 mM pyridoxal-5'-phosphate and 0.5 v/v toluene. The resulting suspension is transferred in a 10-ml test tube, for reaction under shaking at 30° C. for 18 hours. The generated PHG is assayed after the completion of the reaction. This is shown in Table 14. (2S,4S)-PHG could be generated from PHOG.

TABLE 14

| Strains | PHG generated (mM) |
| --- | --- |
| *Aeromonas hydrophila* IFO3820 | 16.4 |
| *Alcaligenes faecalis* ATCC8750 | 12.3 |
| *Proteus rettgeri* IFO13501 | 17.5 |
| *Morganella morganii* IFO3848 | 17.2 |

(4-4) 2R-PHG Production with D-Amino Acid Transaminase

Microorganisms shown below in Table 15 are inoculated on a bouillon plate culture medium (Eiken Chemical Co., Ltd.), and cultured at 30° C. for 24 hours. This is inoculated in 1 ml of a reaction solution containing 100 mM Tris-HCl, pH 7.6, 50 mM PHOG, 100 mM D-glutamic acid, 100 mM D-alanine, 1 mM pyridoxal-5'-phosphate and 0.5 v/v toluene to final wet microbial cells weight of 5% by weight, for incubation at 30° C. for 16 hours. After the completion of the reaction, the generated PHG is assayed. This is shown in Table 15. (2R,4S)-PHG and (2R,4R)-PHG could be generated from PHOG.

TABLE 15

| | PHG generated (mM) | |
| --- | --- | --- |
| Strains | (2R,4R) | (2R,4S) |
| *Bacillus sphaericus* ATCC10208 | 16.6 | 16.5 |
| *Bacillus pulvifaciens* AJ1327 | 2.8 | 2.6 |
| *Paenibacillus larvae* subsp. *pulvifaciens* ATCC13537 | 3.0 | 2.8 |
| *Bacillus macerans* AJ1617* | 7.1 | 7.0 |
| *Paenibacillus macerans* ATCC8244 | 6.5 | 6.5 |
| *Bacillus lentus* AJ12699 | 4.6 | 4.6 |
| *Bacillus lentus* ATCC10840 | 4.2 | 4.3 |

*FERM P-18653

(4-5) Preparation of *E. coli* Expressing DAT Derived from *Bacillus sphaericus* (Referred to as BSDAT Hereinafter) and 2R-PHG production by reaction with rinsed microbial cells
1. Construction of Expression Plasmid So as to express the D-amino acid transaminase gene (abbreviated as "bsdat" hereinafter) derived from *Bacillus sphaericus* in *E. coli*, a plasmid pUCBSDAT is constructed as follows, where the bsdat gene is conjugated to the downstream of the lac promoter of pUC18. Using the chromosomal DNA of the *Bacillus sphaericus* strain ATCC 10208 as template and oligonucleotides shown below in Table 16 as primers, first, the gene is amplified by PCR. In such manner, a DNA fragment corresponding to the 8-th to 1278-th positions in the bsdat nucleotide sequence described as SEQ ID No.2 in the text of European Patent publication 0 736 604 may be amplified. The fragment is treated with BamHI and PstI, conjugated to the BamHI/PstI digestion product of pUC18, and introduced in *E. coli* JM109. From the resulting ampicillin resistant strains, a strain with the intended plasmid is selected, to construct an expression plasmid pUCBSDAT.

TABLE 16

| SQ ID No. 15 | 5'-CCG GGA TTC GTT AAT CCA AAC GTT AGC TG |
| --- | --- |
| SQ ID No. 16 | 5'-GGC CTG CAG TTA GGC ATT AAT TGA AAT TGG |

2. Preparation of *E. coli* Expressing BSDAT

An *E. coli* transformant with pUCBSDAT is seed-cultured in an LB culture medium (1 g/dl bacto-tryptone, 0.5 g/dl yeast extract, and 1 g/dl NaCl) containing 0.1 mg/ml ampicillin at 37° C. for 16 hours. 1 ml of the seed liquid culture is added to a 500-ml Sakaguchi's flask charged with 50 ml of the LB culture medium, and cultured at 37° C. 2.5 hours after the start of the culture, isopropyl 1-thio-β-D-galactopyranoside (IPTG) is added to a final 1 mM concentration, for additional 4-hours of culturing. From the resulting liquid culture, the microbial cells are harvested and rinsed, to prepare *E. coli* expressing BSDAT.

3. Reaction with Rinsed Microbial Cells, Using *E. coli* Expressing BSDAT

The microbial cells prepared in above 2 are suspended in 1 ml of a reaction solution containing 100 mM Tris-HCl, pH 7.6, 50 mM PHOG, 100 mM amino acid donors (D-Glu, D-Ala, L-Glu, L-Ala), 1 mM pyridoxal-5'-phosphate and 0.5 v/v % toluene to a final wet microbial cell weight of 5%, and the resulting suspension is transferred in a 10-ml test tube, for reaction under shaking at 30° C. for 18 hours. The PHG generated is assayed after the completion of the reaction. This is shown in Table 17. (2R,4R), (2R,4S) and (2S,4S)-PHG could be generated from PHOG.

TABLE 17

PHG (mM) generated via reaction with rinsed microbial cells, using *E. coli* expressing BSDAT

| | Added amino acid donors | | | |
| --- | --- | --- | --- | --- |
| Generated PHG | D-Glu | D-Ala | L-Glu | L-Ala |
| (2R,4R) | 20.7 | 25.1 | N.D. | 15.4 |
| (2R,4S) | 17.5 | 17.0 | 22.7 | 7.0 |
| (2S,4S) | trace | trace | 22.7 | trace |

(4-6) Preparation of *E. coli* Expressing DAT Derived from *Bacillus macerans* AJ1617 (Referred to as BMDAT Hereinafter) and 2R-Monatin Production by Reaction with Rinsed Microbial Cells
1. Preparation of Chromosomal DNA The *Bacillus macerans* strain AJ1617 is cultured overnight in a 50-ml bouillon culture medium at 30° C. (pre-culture). 5 ml of the liquid culture as a seed bacterium is cultured in a 50-ml bouillon culture medium. After the microbial strain was cultured up to the latter logarithmic growth stage, 50 ml of the liquid culture is treated by a centrifugation procedure (12,000×, 4° C., 15 minutes) for harvesting the microbial cells. Using the microbial cells, the chromosomal DNA is prepared by the routine method.

2. Isolation of the *Bacillus macerans*-Derived D-Amino Acid Transaminase Gene (Referred to as bmdat Hereinafter) from Gene Libraries First, one unit of a restriction enzyme EcoRI is added to 30 μg of the chromosomal DNA of the *Bacillus macerans* strain AJ1617, for 3-hour reaction at 37° C. for partial digestion. Then, fragments of 3- to 6 kbp are recovered from the DNA by agarose gel electrophoresis. These fragments are ligated to 1 μg of the EcoRI cleavage product of the plasmid pUC118 (after BAP treatment; manufactured by TaKaRa Brewery, Co., Ltd.), to transform *E. coli* JM109 to prepare gene libraries, which are then plated on an LB culture medium (1% tryptone, 0.5% yeast extract, 1% sodium chloride, 2% agar, pH 7.0) containing ampicillin to form colonies. The developed colonies are cultured overnight in an LB liquid culture medium containing ampicillin and isobutyl-1-thio-β-D-galactopyranoside (IPTG) of 0.1 mM at 37° C., for centrifugation to harvest the resulting microbial cells.

The resulting microbial cells are inoculated in a reaction solution of 100 mM Tris-HCl, pH 8.0, 50 mM sodium pyruvate, 100 mM D-glutamic acid, 1 mM pyridoxal-5'-phosphate and 1 v/v % toluene, for reaction at 30° C. for 30 minutes. After the completion of the reaction, the reaction solution is centrifuged. 5 µl of the resulting separated supernatant is added to a 96-well plate containing 200 µl of a reaction solution for pyruvic acid assay (100 mM Tris-HCl, pH 7.6, 1.5 mM NADH, 5 mM MgCl$_2$, 16 U/ml lactate dehydrogenase (manufactured by Oriental Yeast Co., Ltd.)), for reaction at 30° C. for 10 minutes.

Subsequently, the absorbance at 340 nm is read with a plate reader (SPECTRA MAX190, manufactured by Molecular Device). The same assay is conducted by adding sodium pyruvate to a final concentration of 0.2 mM to 1 mM. Using this as the standard, the amount of pyruvic acid reduced is assayed, to detect the D-amino acid transaminase activity.

Via the screening of clones with DAT activity, the clones with the DAT activity are collected. From these transformants, plasmids containing bmdat are prepared and defined as pUCBMDAT. The plasmid pUCBMDAT is treated with EcoRI and treated by agarose gel electrophoresis, so that the inserted fragment is estimated to be of a length of about 3.3 kbp.

3. Nucleotide Sequence of Inserted Fragment

The nucleotide sequence of the inserted fragment in the plasmid pUCBMDAT is determined by dideoxy method. The ORF of about 850 bp corresponding to the 630-th to 1481-th positions in the sequence SEQ ID No.17 in the sequence listing is found. The homology of the ORF to known sequences is examined. The ORF is 91% homologus to the D-amino acid transaminase gene derived from *Bacillus sphaericus* ATCC 10208 in terms of amino acid sequence and is 66% homologus to the D-amino acid transaminase gene derived from *Bacillus* sp. YM-1 in terms of amino acid sequence and is 42% homologus to the D-amino acid transaminase gene derived from *Bacillus lichenifonnis* ATCC10716 in terms of amino acid sequence.

This clearly show that the ORF encoded the D-amino acid transaminase genes. Herein, the homology is calculated using a gene analysis software "genetyx ver. 6" (GENETYX) while various parameters are used as they were initially set.

4. Preparation BMDAT-Expressing *E. coli*

*E. coli* transformant with pUCBMDAT is seed-cultured in an LB culture medium (1 g/dl bacto-tryptone, 0.5 g/dl yeast extract and 1 g/dl NaCl) containing 0.1 mg/ml ampicillin at 37° C. for 16 hours. 1 ml of the seed liquid culture is added to a 500-ml Sakaguchi's flask charged with 50 ml of the LB culture medium and cultured at 37° C. 2.5 hours after the start of the culture, isopropyl 1-thio-β-D-galactopyranoside (IPTG) is added to a final 1 mM concentration and cultured for additional 4-hour. From the resulting liquid culture, the microbial cells are harvested and rinsed, to prepare *E. coli* expressing BMDAT.

5. Reaction with Rinsed Microbial Cells, Using *E. Coli* Expressing BMDAT

The microbial cells prepared above in 4 are suspended in 1 ml of a reaction solution containing 100 mM Tris-HCl, pH 8.0, 50 mM IHOG, 200 mM D-alanine, 1 mM pyridoxal-5'-phosphate and 0.5 v/v % toluene to a final wet microbial cell weight of 5%, and the resulting suspension is transferred in a 10-ml test tube, for reaction under shaking at 33° C. for 20 hours. The 2R-monatin generated is assayed after the completion of the reaction. Consequently, 22 mM 2R-monatin could be generated.

Numerous modifications and variations on the present invention are possible in light of the above teachings. It is, therefore, to be understood that within the scope of the accompanying claims, the invention may be practiced otherwise than as specifically described herein.

INDUSTRIAL APPLICABILITY

The process of producing monatin in accordance with the invention utilizes a process of producing glutamate derivatives and may produce monatin very efficiently using tryptophan as a starting material in an enzymatic reaction. This process is very useful industrially, particularly in the field of food.

We claim:

1. A process for producing monatin or salt thereof comprising:
   (A) converting typtophan to 3-indolepyruvic acid by contacting tryptophan with a transaminase or an oxidase that catalyzes a reaction of converting tryptophan to 3-indolepyruvic acid, and
   (B) converting 3-indolepyruvic acid to 4-(indol-3-ylmethyl)-4-hydroxy-2-oxoglutaric acid by contacting said 3-indolepyruvic acid to an aldolase and an acid selected from the group consisting of oxaloacetic acid and pyruvic acid, wherein said aldolase catalyzes a reaction of converting 3-indolepyruvic acid to 4-(indol-3-ylmethyl)-4-hydroxy-2-oxoglutaric acid; and
   (C) contacting said 4-(indol-3-ylmethyl)-4-hydroxy-2-oxoglutaric acid to a dehydrogenase or a transaminase, wherein said dehydrogenase or said transaminase catalyzes a reaction of converting said 4-(indol-3-ylmethyl)-4-hydroxy-2-oxoglutaric acid to said monatin;
   thereby producing monatin or a salt thereof.

2. The process of claim 1, wherein contacting in (A) is in a reaction vessel under deaeration or deoxygen conditions.

3. The process of claim 2, wherein said conditions comprise substituting at least a part of the gas contained in the reaction vessel with an inactive gas.

4. The process of claim 3, wherein said inactive gas is selected from the group consisting of nitrogen, argon, and helium.

5. The process of claim 1, further comprising:
   in (A) adjusting the pH of the reaction to 2 after said tryptophan is contacted with said enzyme.

6. The process of claim 5, wherein adjusting the pH comprises adding an acid to the reaction.

7. The process of claim 6, wherein said acid is selected from the group consisting of sulfuric acid, hydrochloric acid, nitric acid, and phosphoric acid.

8. The process of claim 5, wherein said crystals of said 3-indolepyruvic acid form as a result of adjusting the pH.

9. The process of claim 8, further comprising collecting said crystals.

10. The process of claim 1, wherein said oxidase in step (A) is isolated from a microorganism having amino acid oxidase activity and catalase activity.

11. The process of claim 1, wherein said transaminase or oxidase in (A) is isolated from a microorganism selected from the group consisting of *Achromobacter, Proteus, Morganella, Pseudomonas*, and *Neurospora*.

12. The process of claim 1, wherein said aldolase in (B) is isolated from a microorganism selected from the group consisting of *Pseudomonas, Erwinia, Flavobacterium*, and *Xanthomonas*.

13. The process of claim 1, wherein said aldolase in (B) is isolated from a microorganism selected from the group consisting of *Pseudomonas taetrolens, Pseudomonas coronafaciens, Pseudomonas desmolytica, Erwinia* sp., *Flavobacterium rhenanum*, and *Xanthomonas citri*.

14. The process of claim 1, wherein said aldolase in (B) is a protein selected from the group consisting of (a) a protein having an amino acid sequence comprising SEQ ID NO: 2;
(b) a protein having an amino acid sequence comprising substitution, deletion, insertion, and/or addition of one to ten amino acid residues of SEQ ID NO: 2 and having aldolase activity;
(c) a protein having an amino acid sequence comprising SEQ ID NO: 3;
(d) a protein having an amino acid sequence comprising substitution, deletion, insertion, and/or addition of one to ten amino acid residues of SEQ ID NO: 3 and having aldolase activity;
(e) a protein encoded by a polynucleotide that hybridizes with a polynucleotide comprising a nucleotide sequence complementary to the nucleotide sequence of SEQ ID NO: 1 under stringent conditions, wherein said stringent conditions comprising 0.1×SSC and 0.1% SDS at 65° C., wherein said protein has aldolase activity.

15. The process of claim 14, wherein said aldolase is isolated from a recombinant cell, wherein a gene encoding said enzyme is amplified and expressed.

16. The process of claim 1, wherein in (C) said contacting is with a transaminase, and said reaction is additionally exposed to one or more types of amino acids.

17. The process of claim 16, wherein said amino acids are selected from the group consisting of glutamic acid, aspartic acid, alanine, tryptophan, phenylalanine, isoleucine, leucine, tyrosine, valine, arginine, asparagine, glutamine, methionine, ornithine, serine, cysteine, histidine and lysine.

18. The process of claim 1, wherein in (C) said contacting is with a L-amino acid transaminase.

19. The process of claim 18, wherein said L-amino acid transaminase is isolated from a microorganism genera selected from the group consisting of *Aeromonas, Agrobacterium, Alcaligenes, Beijerinckia, Escherichia, Proteus* and *Morganella*.

20. The process of claim 19, wherein said microorganism is selected from the group consisting of *Aeromonas hydrophila, Agrobacterium tumefaciens, Alcaligenes faecalis, Beijerinckia indica, Escherichia coli, Proteus rettgeri* and *Morganella morganii*.

21. The process of claim 1, wherein in (C) said contacting is with a D-amino acid transaminase.

22. The process of claim 21, wherein said enzyme has an activity of catalyzing a reaction for converting L-amino acid to D-amino acid.

23. The process of claim 21, wherein said D-amino acid transaminase is isolated from a microorganism genera selected from the group consisting of *Bacillus* and *Paenibacillus*.

24. The process of claim 23, wherein said microorganism is selected from the group consisting of *Bacillus sphaericus, Bacillus pulvifaciens, Bacillus macerans, Bacillus lentus, Paenibacillus larvae* subsp. *pulvifaciens* and *Paenibacillus macerans*.

25. The process of claim 1, wherein in (C) said contacting is with a transaminase and said transaminase is isolated from a microorganism having the D-amino acid transaminase gene introduced therein.

26. The process of claim 25, wherein said microorganism is *Escherichia coli*.

27. The process of claim 25, wherein said D-amino acid transaminase gene is isolated from *Bacillus sphaericus* or *Bacillus macerans*.

* * * * *